(12) United States Patent
Brahmbhatt et al.

(10) Patent No.: US 12,357,687 B2
(45) Date of Patent: Jul. 15, 2025

(54) COMPOSITIONS AND VACCINES FOR TREATING AND/OR PREVENTING VIRAL INFECTIONS, AND METHODS OF USING THE SAME

(71) Applicant: EnGeneIC Molecular Delivery Pty Ltd, Sydney (AU)

(72) Inventors: Himanshu Brahmbhatt, Sydney (AU); Jennifer MacDiarmid, Sydney (AU)

(73) Assignee: EnGeneIC Molecular Delivery Pty Ltd, Sydney (AU)

( * ) Notice: Subject to any disclaimer, the term of this patent is extended or adjusted under 35 U.S.C. 154(b) by 878 days.

(21) Appl. No.: 17/480,073

(22) Filed: Sep. 20, 2021

(65) Prior Publication Data

US 2022/0111038 A1 Apr. 14, 2022

Related U.S. Application Data

(63) Continuation-in-part of application No. PCT/IB2021/052402, filed on Mar. 23, 2021.

(60) Provisional application No. 63/224,838, filed on Jul. 22, 2021, provisional application No. 62/994,057, filed on Mar. 24, 2020.

(51) Int. Cl.
| | |
|---|---|
| *A61K 39/215* | (2006.01) |
| *A61K 9/00* | (2006.01) |
| *A61K 31/427* | (2006.01) |
| *A61K 31/4706* | (2006.01) |
| *A61K 31/513* | (2006.01) |
| *A61K 31/519* | (2006.01) |
| *A61K 31/53* | (2006.01) |
| *A61K 31/635* | (2006.01) |
| *A61K 31/675* | (2006.01) |
| *A61K 38/21* | (2006.01) |
| *A61K 39/39* | (2006.01) |
| *A61P 31/14* | (2006.01) |
| *A61K 39/00* | (2006.01) |

(52) U.S. Cl.
CPC ......... *A61K 39/215* (2013.01); *A61K 9/0019* (2013.01); *A61K 31/427* (2013.01); *A61K 31/4706* (2013.01); *A61K 31/513* (2013.01); *A61K 31/519* (2013.01); *A61K 31/53* (2013.01); *A61K 31/635* (2013.01); *A61K 31/675* (2013.01); *A61K 38/215* (2013.01); *A61K 39/39* (2013.01); *A61P 31/14* (2018.01); *A61K 2039/521* (2013.01); *A61K 2039/523* (2013.01); *A61K 2039/55* (2013.01); *A61K 2039/55511* (2013.01)

(58) Field of Classification Search
None
See application file for complete search history.

(56) References Cited

U.S. PATENT DOCUMENTS

| | | | |
|---|---|---|---|
| 8,524,484 B2 * | 9/2013 | Sabbadini | C12N 15/00 435/320.1 |
| 10,973,908 B1 | 4/2021 | Bermudes | |
| 2006/0002956 A1 | 1/2006 | Surber et al. | |
| 2008/0038296 A1 * | 2/2008 | Brahmbhatt | C07K 16/1203 424/234.1 |
| 2008/0051469 A1 | 2/2008 | Brahmbhatt et al. | |
| 2012/0252099 A1 | 10/2012 | Sabbadini et al. | |
| 2017/0165345 A1 * | 6/2017 | Leadbetter | A61K 9/5153 |
| 2017/0326235 A1 | 11/2017 | Brahmbhatt et al. | |
| 2020/0054689 A1 | 2/2020 | Brahmbhatt et al. | |
| 2021/0283244 A1 | 9/2021 | Chen et al. | |

FOREIGN PATENT DOCUMENTS

| | | | |
|---|---|---|---|
| JP | 2009-530264 A | 8/2009 | |
| JP | 2012-505174 A1 | 3/2012 | |
| WO | WO 2000/67776 | 11/2000 | |
| WO | WO 2003/033519 A2 | 4/2003 | |
| WO | WO 2004/113507 A1 | 12/2004 | |
| WO | WO-2006/107097 A1 | 10/2006 | |
| WO | WO 2020/021437 A1 | 1/2020 | |
| WO | WO2021/91796 * | 9/2021 | ......... C07K 16/1203 |
| WO | WO 2021/243974 A1 | 12/2021 | |

OTHER PUBLICATIONS

King et al (Frontiers in Immunol. 9 (1519): 1-7. Jul. 2, 2018).*
Kemp et al. (BioRxiv, Mar. 8, 2020).*
Written Opinion PCT/IB2021/052402, 2021.*
International Preliminary Report on Patentability issued in International Patent Application No. PCT/IB2021/052402, dated Oct. 6, 2022.
International Search Report that issued in International Patent Application No. PCT/IB2021/052402, dated Jun. 23, 2021.
Fotouhi, et al., "Adjuvant use of the NKT cell agonist alpha-galactosylceramide leads to enhancement of M2-based DNA vaccine immunogenicity and protective immunity against influenza A virus," *Archives of Virology*, vol. 162, pp. 1251-1260 (2017).
Gao, et al., "Nanocell COVID-19 Vaccine elicits INKT-licensed dendritic cells to produce high affinity antibodies neutralizing variants of concern," Research Square, (Apr. 2022), pp. 1-36.
International Search Report and Written Opinion issued in International Patent Application No. PCT/IB2022/056759, dated Nov. 1, 2022.
Agnihothram et al., "Evaluation of serologic and antigenic relationships between Middle Eastern respiratory syndrome coronavirus and other coronaviruses to develop vaccine platforms for the rapid response to emerging coronaviruses," J Infect Dis. 2014;209(7):995-1006.
Bolles et al., "A double-inactivated severe acute respiratory syndrome coronavirus vaccine provides incomplete protection in mice and induces increased eosinophilic proinflammatory pulmonary response upon challenge," J. Virol. 2011;85(23):12201-12215.

(Continued)

*Primary Examiner* — Agnieszka Boesen
(74) *Attorney, Agent, or Firm* — Foley & Lardner LLP

(57) ABSTRACT

The present disclosure is directed to compositions and methods useful for treating, as well as vaccinating against, viral infections, including coronavirus infections.

25 Claims, 29 Drawing Sheets
(14 of 29 Drawing Sheet(s) Filed in Color)

Specification includes a Sequence Listing.

(56) References Cited

OTHER PUBLICATIONS

Bungener et al., "Delivery of protein antigens to the immune system by fusion-active virosomes: a comparison with liposomes and ISCOMs," Biosci. Rep., 22(2):323-38 (2002).
Chan, et al., "Genomic characterization of the 2019 novel human-pathogenic coronavirus isolated from a patient with atypical pneumonia after visiting Wuhan," Emerg. Microbes Infect. 9, 221-236 (2020).
Chen et al., "Antigen Delivery to Macrophages Using Liposomal Nanoparticles Targeting Sialoadhesin/CD169," PLoS ONE 7(6): e39039 (2012), 9 pages.
Daemen et al., "Virosomes for antigen and DNA delivery," Adv Drug Deliv Rev., Jan. 10, 2005;57(3):451-463.
Drosten, et al., "Identification of a novel coronavirus in patients with severe acute respiratory syndrome," N Engl J Med. 2003; 348(20):1967-1976.
Duan, et al., "Pre- and post-treatment chest CT findings: 2019 novel coronavirus (2019-nCOV) pneumonia," Radiology 2020, 1 page.
Grohskopf, et al., "Prevention and control of seasonal influenza with vaccines: Recommendations of the Advisory Committee on Immunization Practices-United States, 2018-19 influenza season. MMWR," Recomm. Rep. 67, 1-20 (2018).
Guan, et al., "Clinical characteristics of 2019 novel coronavirus infection in China," medRxiv. (2020), 30 pages.
Huang, et al., "Clinical features of patients infected with 2019 novel coronavirus in Wuhan, China," Lancet. 395, 497-506 (2020).
Jiang, et al., "SARS vaccine development," Emerg. Infect. Dis. 11, 1016-1020 (2005).
Kersten, et al., "Liposomes and ISCOMs," Vaccine, 21(9-10):915-920 (2003).
Ksiazek, et al., "A novel coronavirus associated with severe acute respiratory syndrome," *N Engl J Med*. 2003; 348(20):1953-1966.
Lew, et al., "Acute respiratory distress syndrome in critically Ill patients with severe acute respiratory syndrome," *JAMA*. 2003; 290(3):374-380.
Menachery et al., "A SARS-like cluster of circulating bat coronaviruses shows potential for human emergence," Nat Med. 2015; 21:1508-1513.
Regla-Nava, et al., "Severe acute respiratory syndrome coronaviruses with mutations in the E protein are attenuated and promising vaccine candidates," J. Virol. 89, 3870-3887 (2015).
Schoggins, et al., "A diverse range of gene products are effectors of the type I interferon antiviral response," Nature. 2011;472(7344):481-485.
Shang, et al., "The outbreak of SARS-CoV-2 pneumonia calls for viral Vaccines," Vaccines (2020) 5:18, 3 pages.
Sheahan et al., "Successful vaccination strategies that protect aged mice from lethal challenge from influenza virus and heterologous severe acute respiratory syndrome coronavirus," J Virol. 2011;85(1):217-230.
Su, et al., "Construction of Stable LamB-Shiga Toxin B Sununit Hybrids: Analysis of Expression in Salmonella typhimurium aroA Strains and Stimulation of B Subunit-Specific Mucosal and Serum Antibody Responses," *Infection and Immunity*, 60(8):3345-3359 (1992).
Wu, F. et al., "A new coronavirus associated with human respiratory disease in China," Nature, 20 pages, (2020).
Yue, et al., "Progress and perspectives in developing polymeric vectors for in vitro gene delivery," Biomater. Sci., 1:152-170 (2013).
Zaki, et al., "Isolation of a novel coronavirus from a man with pneumonia in Saudi Arabia," N Engl J Med. 2012;367(19):1814-1820.
European Search Report for EP Appl. Ser. No. 21774470 dated Feb. 26, 2024 (7 pages).
Search Report issued in European Patent Application No. 22845545. 7, dated May 13, 2025 (9 pages).
GenBank "Severe acute respiratory syndrome coronavirus 2 isolate Wuhan-Hu-1, complete genome," GenBank, URL: https://www.ncbi.nlm.nih.gov/nuccore/MN908947.3, 2020, Accession No. MN908947, Version MN908947.3 (10 pages).
Giacalone et al, "Immunization with non-replicating *E. coli* minicells delivering both protein antigen and DNA protects mice from lethal challenge with lymphocytic choriomeningitis virus," Vaccine, Mar. 8, 2007, vol. 25, No. 12 (16 pages).
Giacalone et al., "Immune responses elicited by bacterial minicells capable of simultaneous DNA and protein antigen delivery,", Vaccine, 2006, vol. 24 (pp. 6009-6017).
Hosseini et al., "Potential SARS-CoV-2 vaccines: Concept, progress, and challenges", International Immunopharmacology, 2021, vol. 97 (15 pages).
Notice of Reasons for Refusal on Japanese Appl. No. 2022-557099, dated Mar. 11, 2025 (14 pages with English language translation).

\* cited by examiner

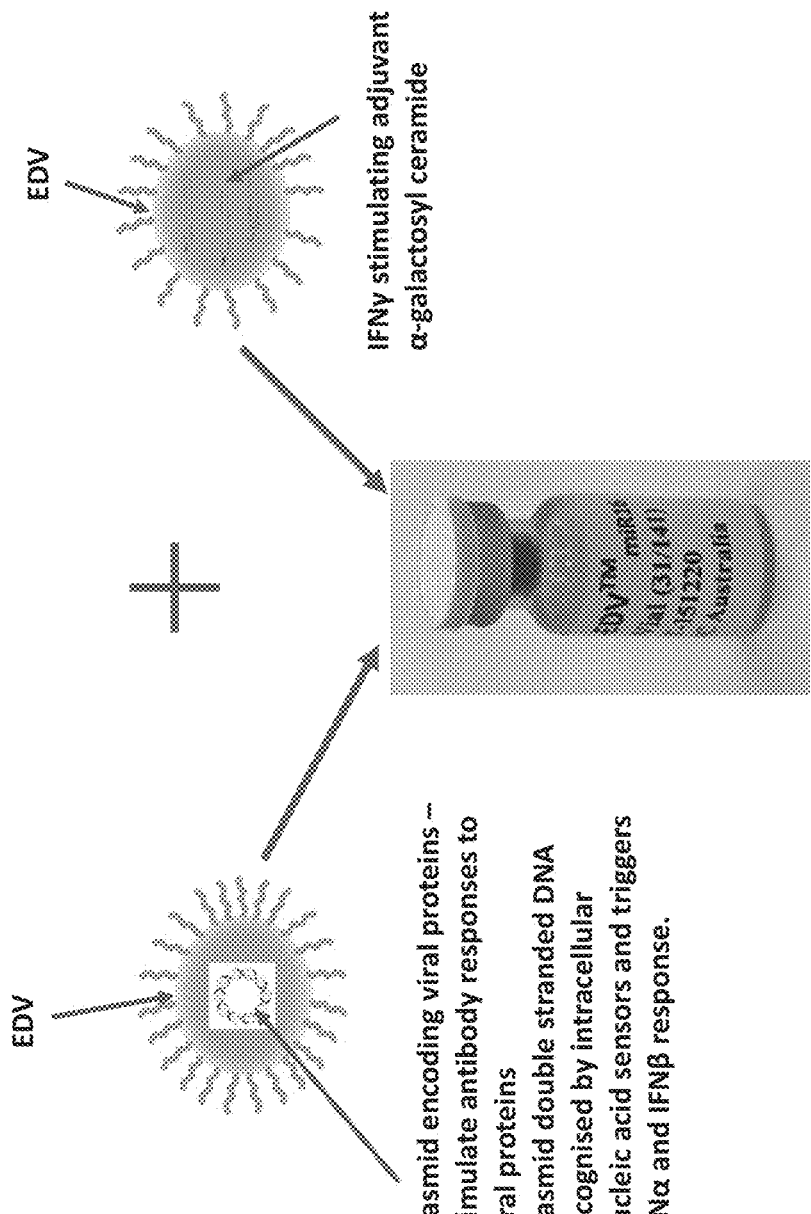

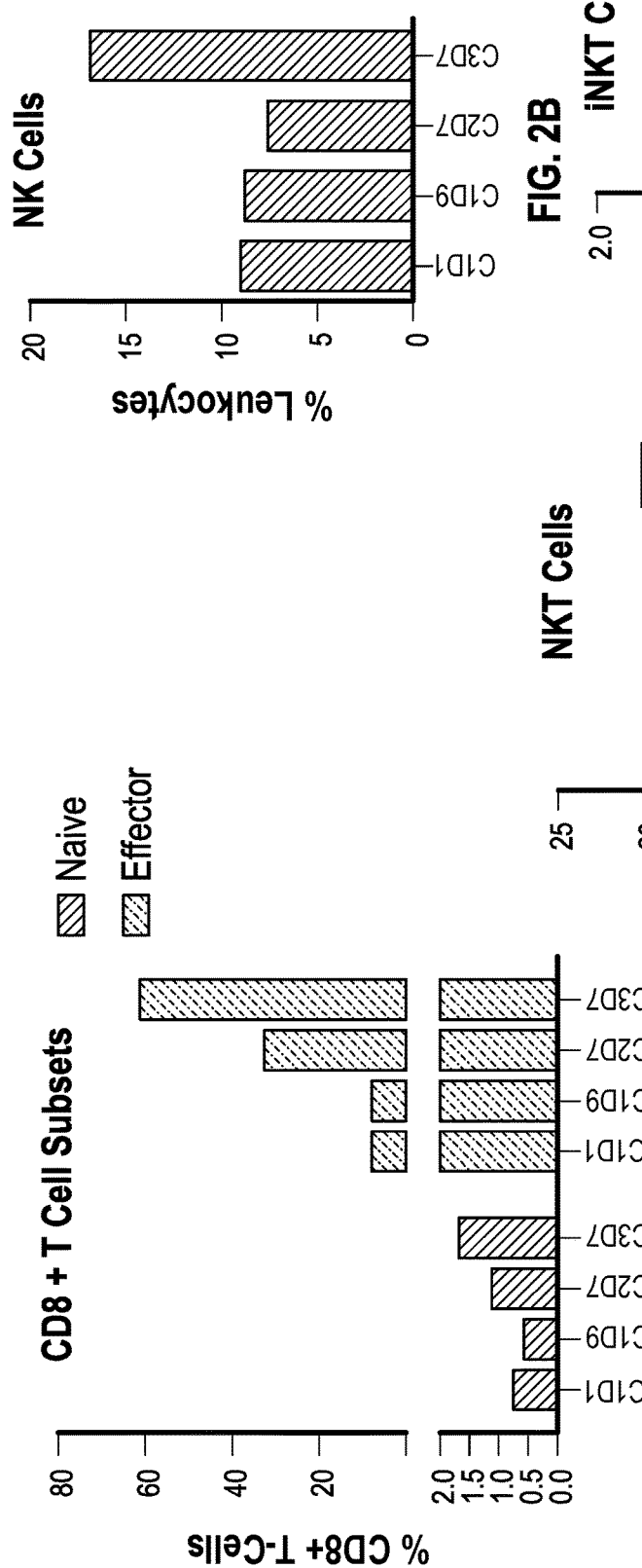
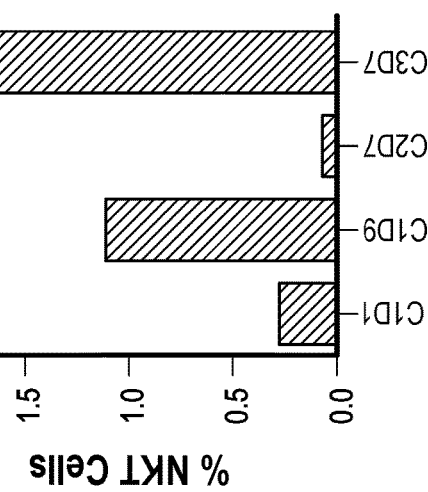
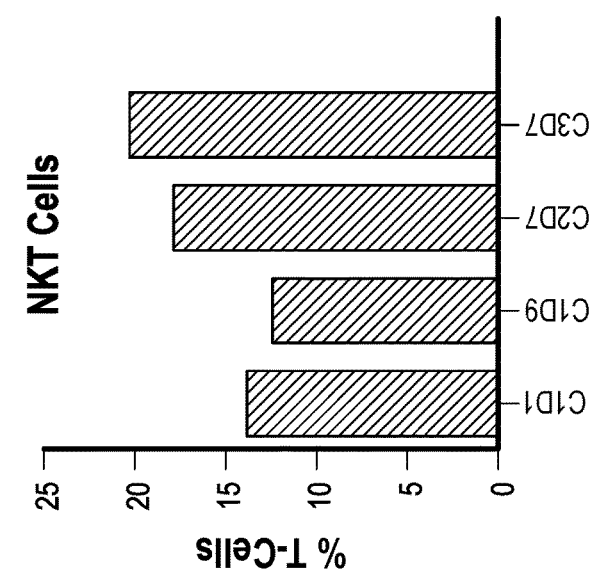
FIG. 2A, FIG. 2B, FIG. 2C, FIG. 2D

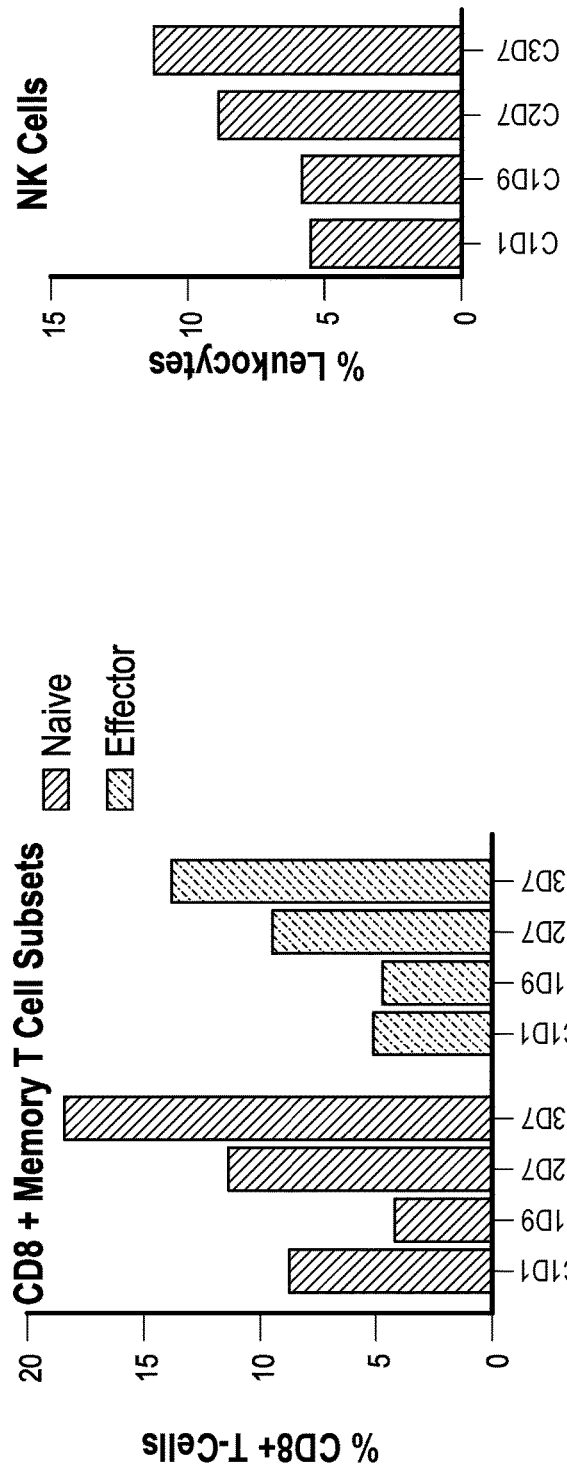
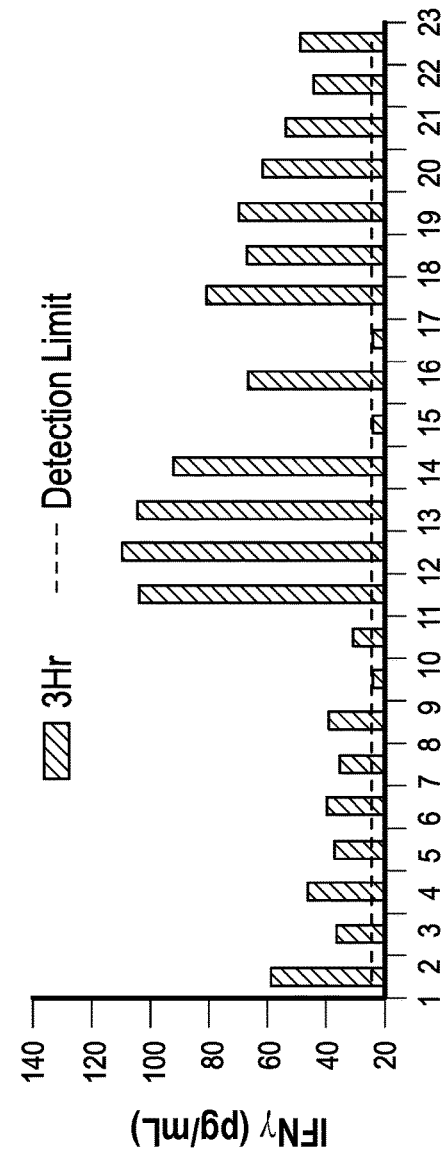
FIG. 3A
FIG. 3B
FIG. 3C

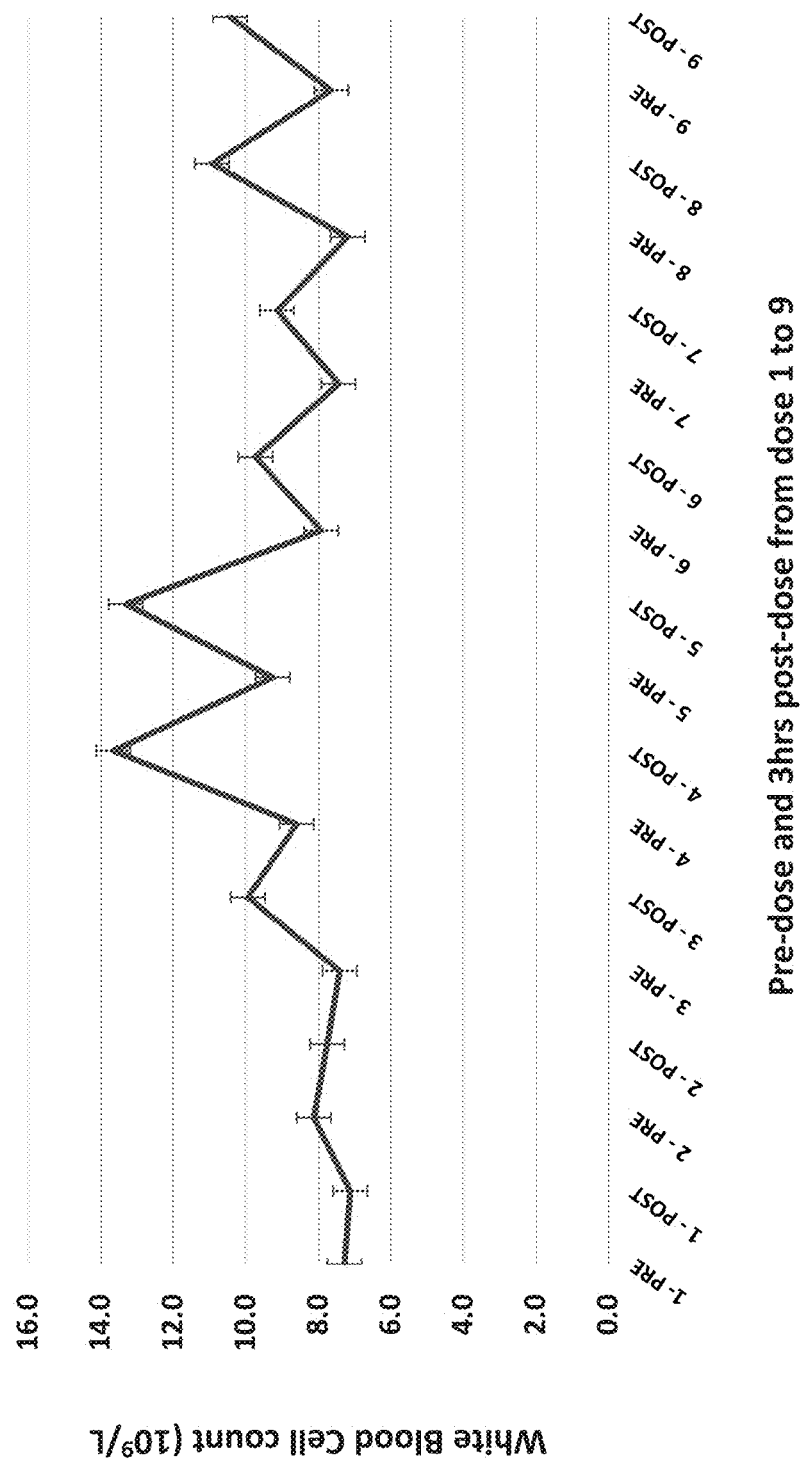

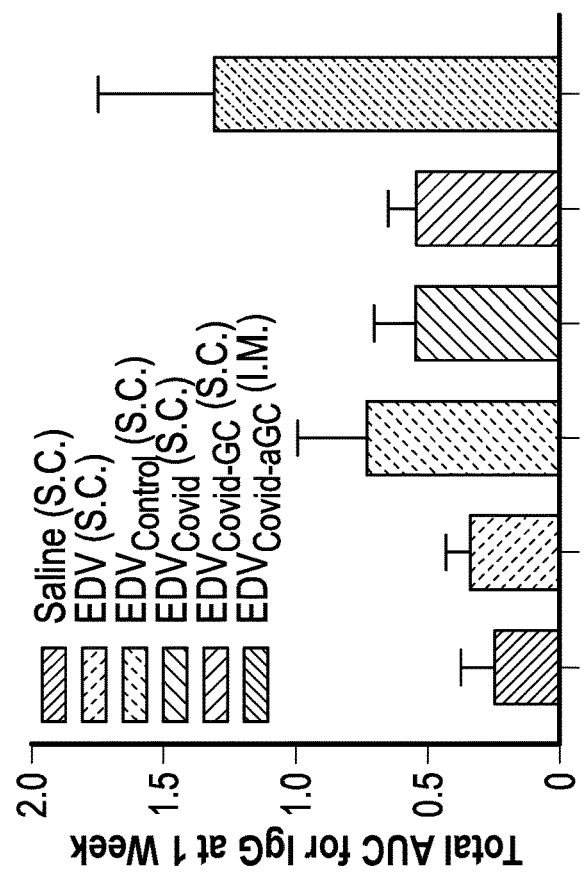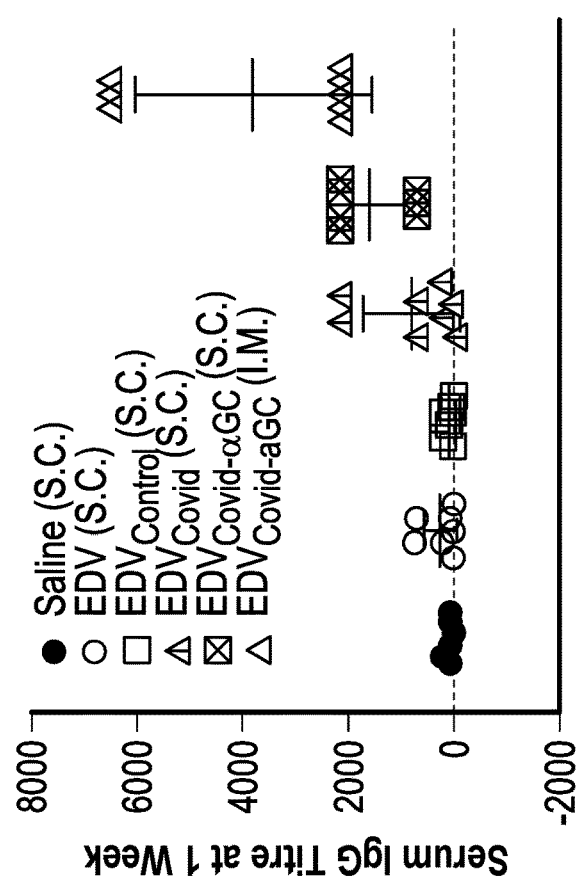
FIG. 6A
FIG. 6B

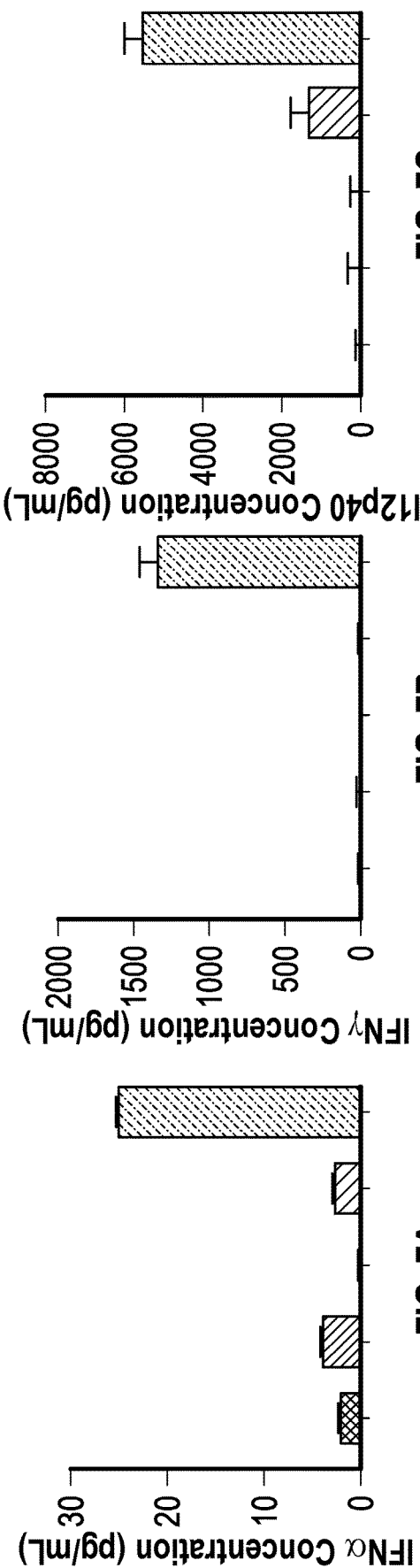

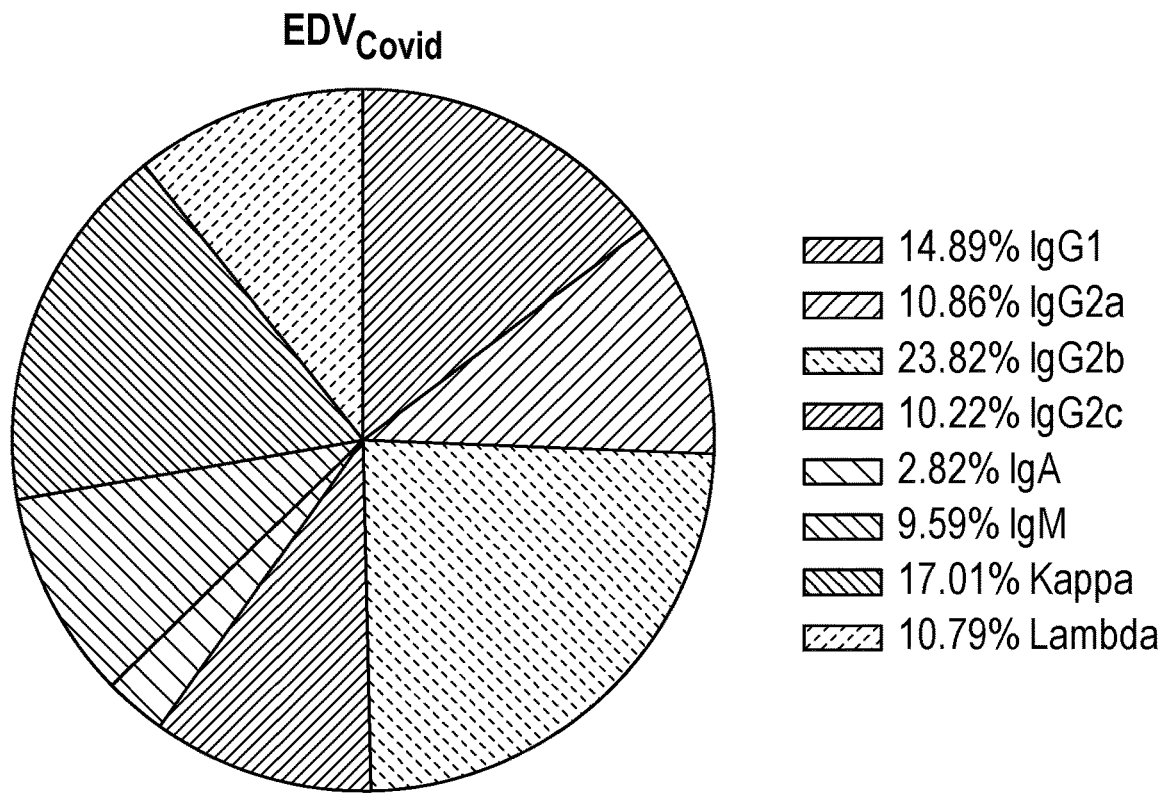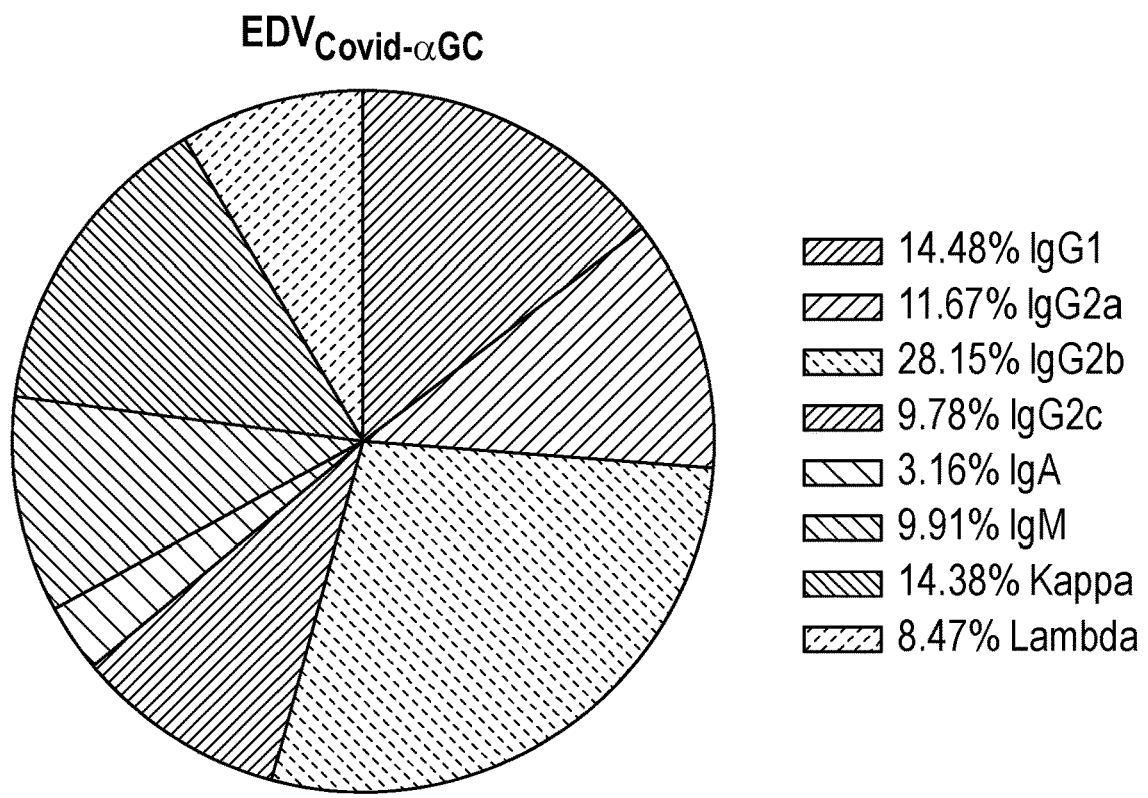
FIG. 8E

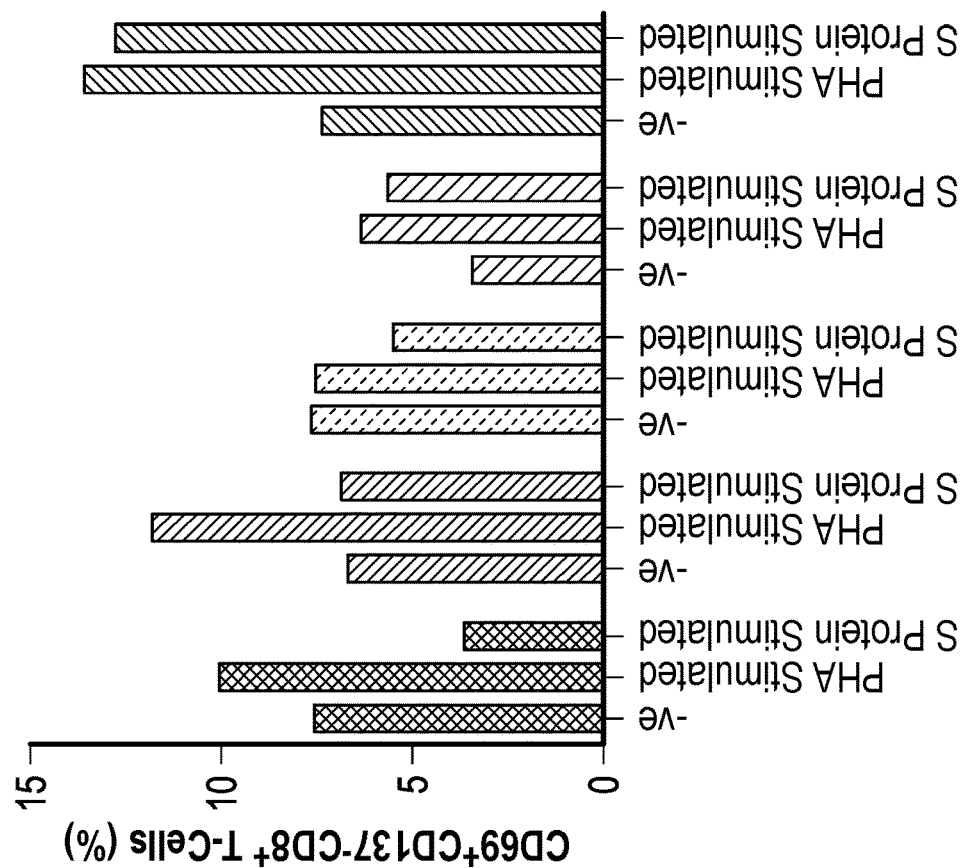
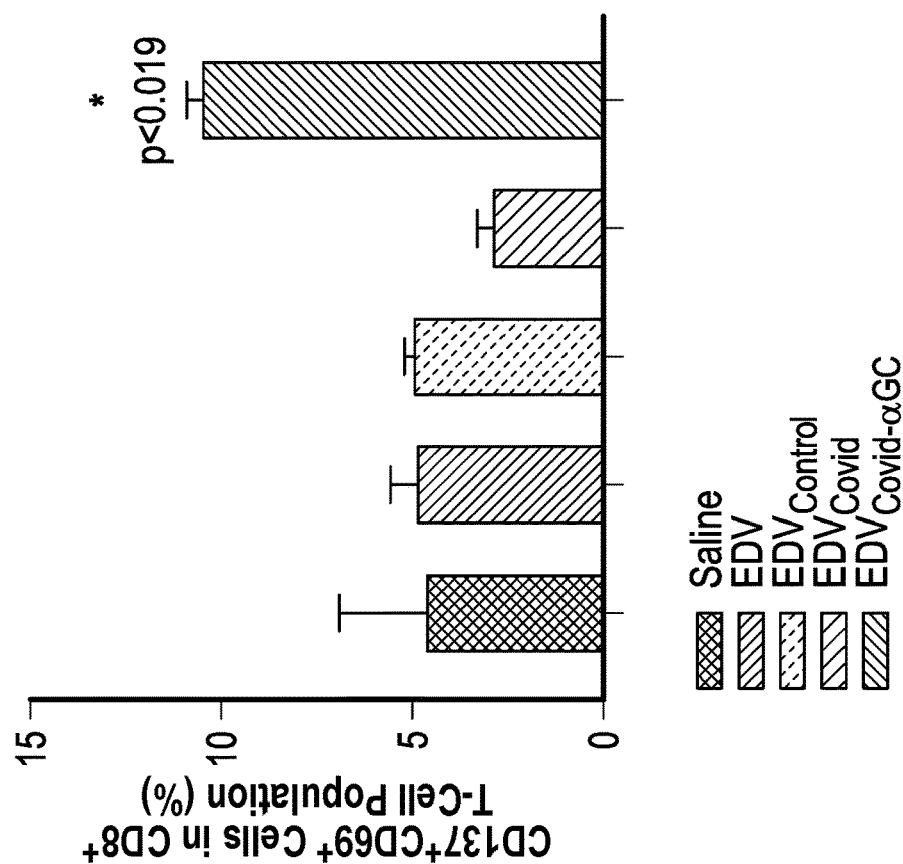
FIG. 9A
FIG. 9B

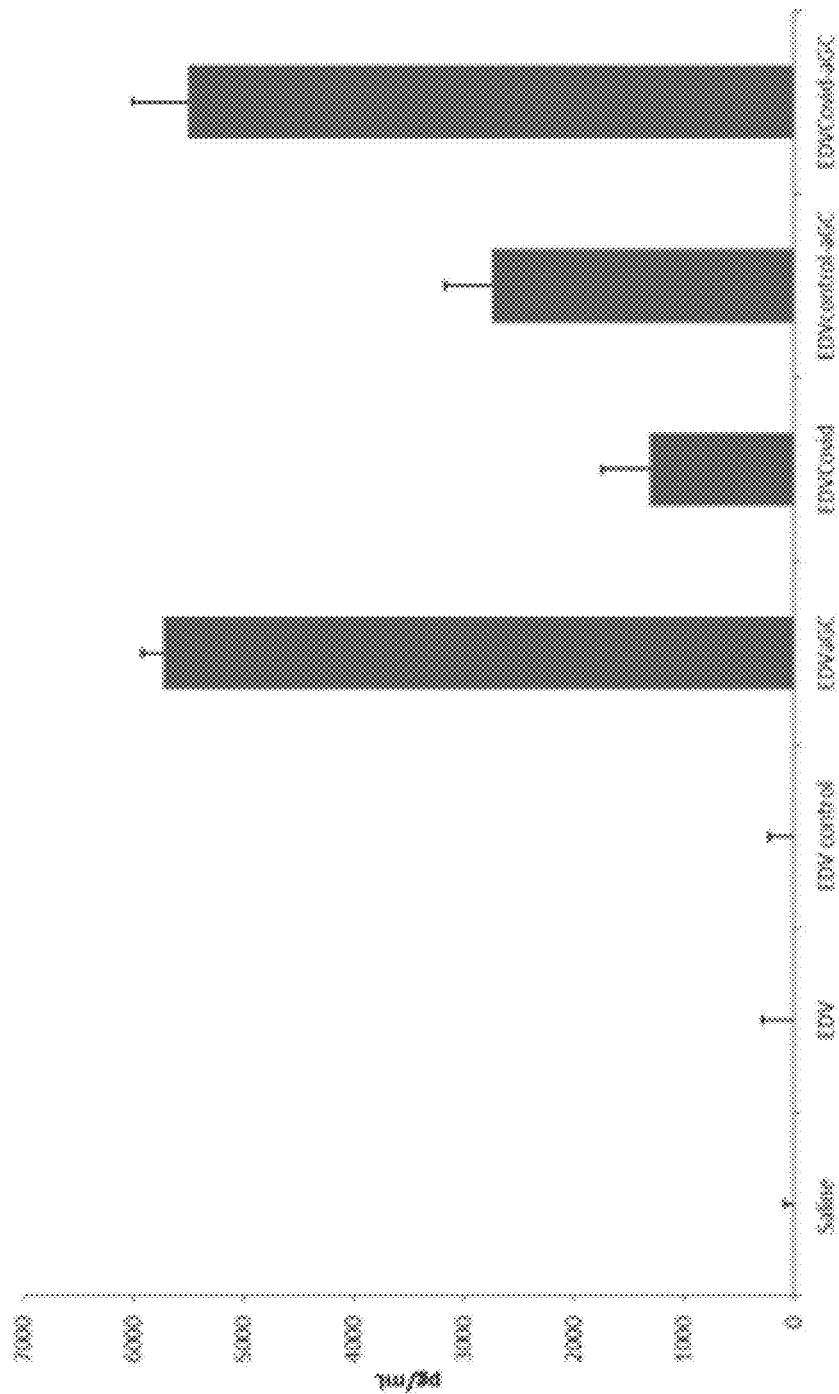

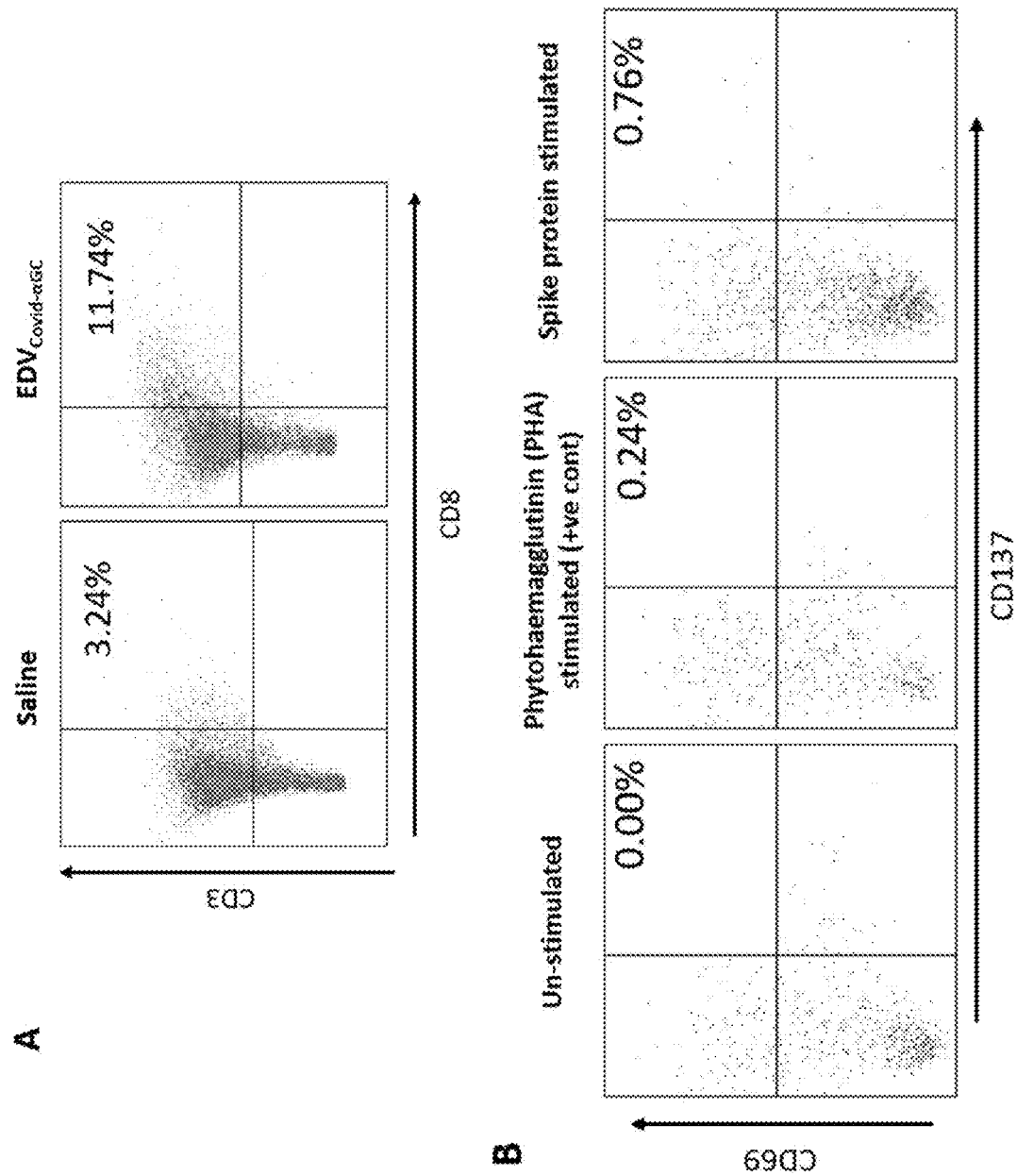

- Mutant Spike protein e.g. delta variant
- Mutant Spike protein e.g. Brazil variant
- Spike protein produced by SARS-CoV-2
- Gene expression promoter expresses all proteins as a single mRNA and separate proteins
- EDV
- plasmid expressing cloned Spike proteins from original SARS-CoV-2 and multiple genetic variants
- Glycolipid α-galactosyl ceramide IFN-γ stimulating adjuvant

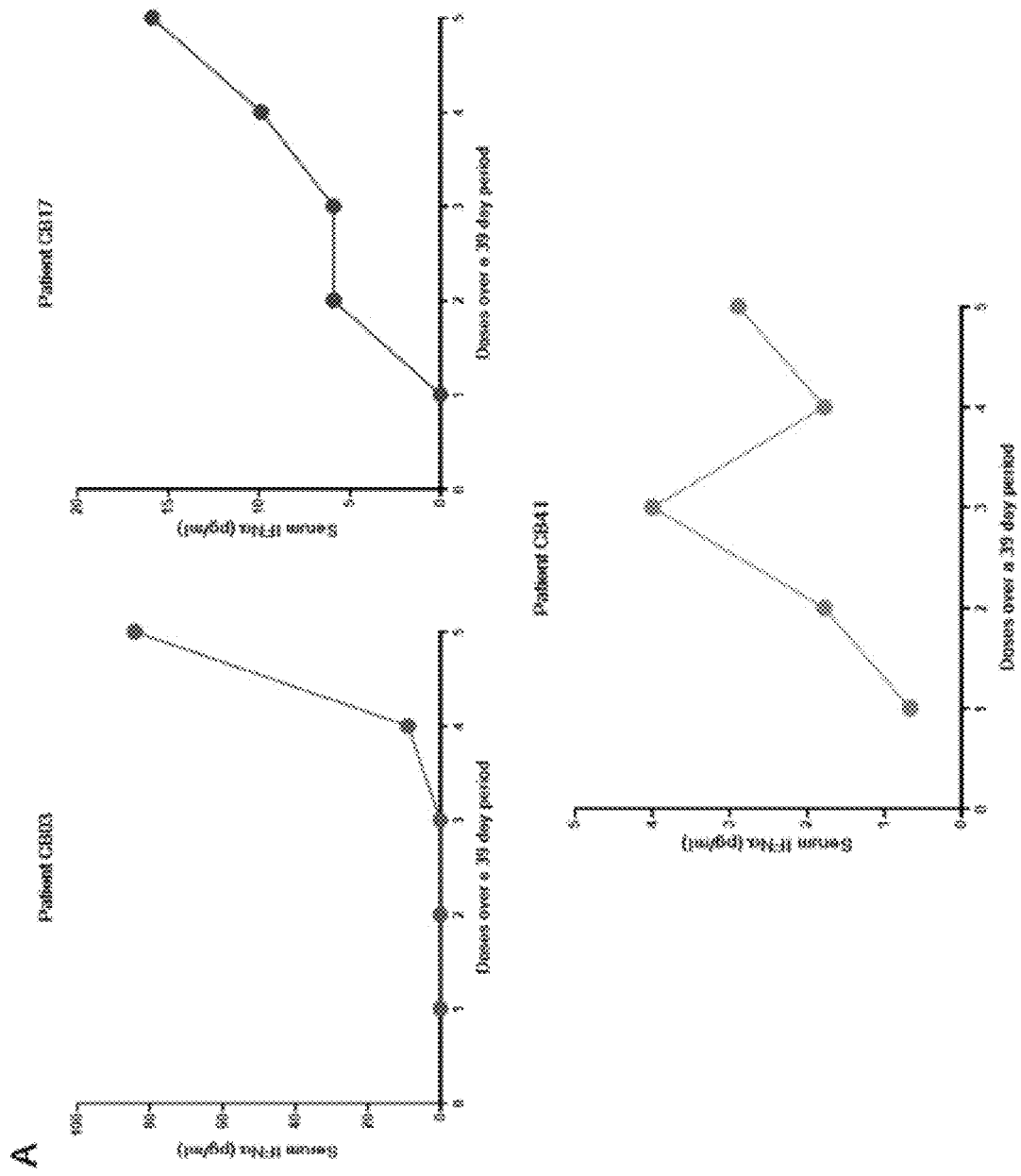

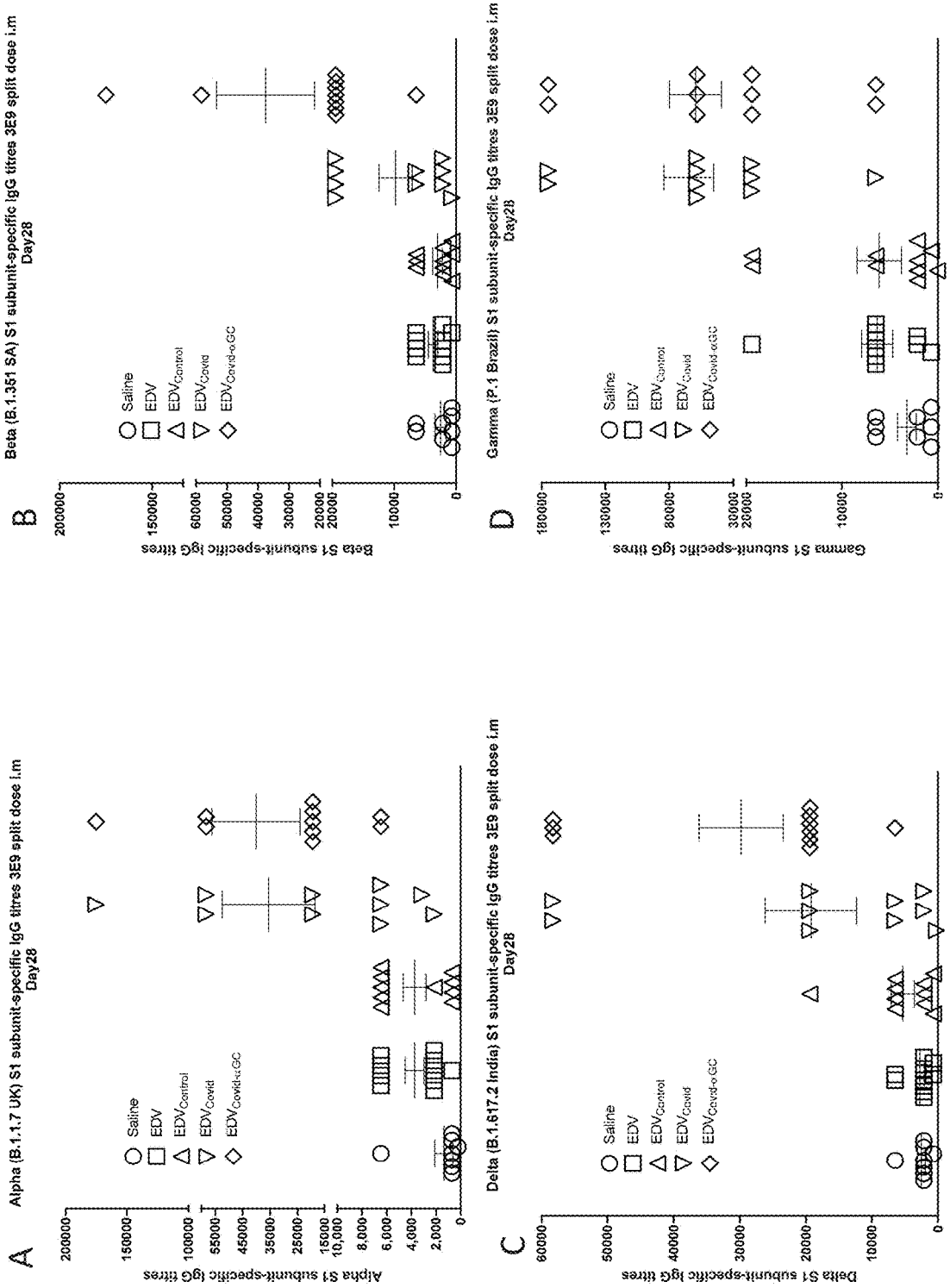

SEQUENCE LISTING

```
<160> NUMBER OF SEQ ID NOS: 6

<210> SEQ ID NO 1
<211> LENGTH: 148
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
cgccagggtt tcccagtca cgacgttgta aaacgacggc cagagaattc gagctcggta      60
cctcgcgaat acatctagat atcggatccc gggcccgtcg actgcagagg cctgcatgca     120
agcttggtgt aatcatggtc atagctgt                                        148

<210> SEQ ID NO 2
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Thr Met Ile Thr Pro Ser Leu His Ala Gly Leu Cys Ser Arg Arg
1               5                   10                  15

Ala Arg Asp Pro Ile Ser Arg Cys Ile Arg Glu Val Pro Ser Ser Asn
            20                  25                  30

Ser Leu Ala Val Val Leu Gln Arg Arg Asp Trp Glu Asn
        35                  40                  45

<210> SEQ ID NO 3
<211> LENGTH: 83
<212> TYPE: DNA
<213> ORGANISM: Unknown
<220> FEATURE:
<223> OTHER INFORMATION: Description of Unknown:
      P-lactamase promoter sequence

<400> SEQUENCE: 3
tctaaataca ttcaaatatg tatccgctca tgagacaata accctgataa atgcttcaat     60
aatattgaaa aaggaagagt atg                                             83

<210> SEQ ID NO 4
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 4
aattcataca ttcaaatatg tatccgctca tgagacaata accctgctcg agtattgaaa      60
aaggaagcat atgaag                                                      76

<210> SEQ ID NO 5
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gatccttcat atgcttcctt tttcaatact cgagcagggt tattgtctca tgagcggata      60
catatttgaa tgtatg                                                      76

<210> SEQ ID NO 6
<211> LENGTH: 12
<212> TYPE: RNA
<213> ORGANISM: Severe acute respiratory syndrome coronavirus 2

<400> SEQUENCE: 6
aaaaaaaaaa aa                                                          12
```

COMPOSITIONS AND VACCINES FOR TREATING AND/OR PREVENTING VIRAL INFECTIONS, AND METHODS OF USING THE SAME

CROSS-REFERENCE TO RELATED APPLICATIONS

This application claims the benefit of priority under 35 USC § 119 from U.S. Provisional Patent Application No. 63/224,838, filed Jul. 22, 2021; this application is also a continuation-in-part of International Patent Application No. PCT/IB2021/052402, filed Mar. 23, 2021, which claims the benefit of priority under 35 USC § 119 from U.S. Provisional Patent Application No. 62/994,057, filed Mar. 24, 2020; the entire contents of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Dec. 30, 2021, is named 060348-0773 SL.txt and is 2,457 kilobytes in size.

BACKGROUND

Outbreaks of severe acute respiratory syndrome (SARS, 2002-2004 [Ksiazek et al., 2003; Drosten et al., 2003]) and Middle East respiratory syndrome (MERS, 2012-current [Zaki et al., 2012]) in the last two decades are a significant threat to global public health. Respiratory syndromes caused by coronaviruses (CoVs) that are transmitted from person-to-person via close contact, result in high morbidity and mortality in infected individuals. Both SARS-CoV and MERS-CoV are capable of causing acute respiratory distress syndrome (ARDS), the most severe form of acute lung injury where alveolar inflammation, pneumonia, and hypoxic lung conditions lead to respiratory failure, multiple organ disease, and death in 50% of ARDS patients [Lew et al., 2003].

Over the decades, research effort has gone into developing antiviral drugs and these are directed largely at nonstructural proteins involved in viral replication and assembly since many of these proteins are highly conserved and can have broad spectrum antiviral activity. Structural and accessory proteins tend to be less conserved and are susceptible to a high mutation rate allowing escape of mutant viruses from the effect of the antiviral drugs. Examples of successful antiviral drugs include oseltamivir phosphate (Tamiflu®) and Zanamivir (Relenza*), both neuraminidase inhibitors used to treat and prevent influenza A and influenza B (flu), and ribavirin, which is a guanosine analog with in vitro activity against a large number of highly lethal emerging viruses.

Monoclonal antibodies (mAbs) have potential utility in combating highly pathogenic viral diseases, by prophylactic and therapeutic neutralization of structural proteins on virions. Unfortunately, these mAbs have to be directed at the surface exposed structural proteins and these tend to mutate at a high frequency. Hence, it was found that mAbs that were effective against CoV infection in animal models targeted the highly variable Spike glycoprotein, but these mAbs lack cross-protection against other related CoVs [Agnihothram et al., 2014]. Pre-clinical and clinical mAb formulations may include a cocktail of multiple mAbs that target different epitopes to ensure that viruses cannot:escape neutralization.

Vaccines have long been considered the gold standard for infectious disease prevention and eradication targeted at human populations as well as conferring the benefits of long-lived immune protection for the individual. Unfortunately, in human infections of highly pathogenic coronaviruses SARS-CoV and MERS-CoV, the most vulnerable populations are patients over the age of 65 and patients with comorbidities, and design of efficacious vaccines for patients in these groups is difficult. Vaccine formulations that have been developed against SARS-CoV not only fail to protect animal models of aged populations, but also result in immunopathology in younger populations, where SARS disease is enhanced in vaccinated groups that are subsequently challenged with SARS-CoV [Bolles et al., 2011; Sheahan et al., 2011].

Due to the diversity of Bat-CoVs, it seems unlikely that current therapeutic strategies targeting specific SARS-CoV or MERS-CoV antigens will be efficacious against future coronaviruses that emerge into the human population. Vaccines formulated against the SARS-CoV epidemic antigens do not offer effective protection against SARS-like Bat-CoVs that are currently circulating in bat populations [Menachery et al., 2015].

Accordingly, new compositions and methods are needed for effective stimulation of antiviral immunity, including but not limited to coronavirus antiviral immunity. The present invention satisfies these needs.

SUMMARY OF THE INVENTION

The present disclosure is directed to compositions comprising: (a) at least one vector comprising a plasmid that encodes at least one viral antigen; and (b) at least one vector comprising a CD1d-recognized antigen; and (c) at least one pharmaceutically acceptable carrier, wherein at least one of vector (a) and vector (b) is an intact, bacterially-derived minicell or killed bacterial cell.

In one aspect for the compositions described herein, vector (a) is a first intact, bacterially derived minicell or killed bacterial cell, and vector (b) is a second intact, bacterially derived minicell or killed bacterial cell. In another aspect, vector (a) and vector (b) are the same intact, bacterially derived minicell or killed bacterial cell, comprising the CD1d-recognized antigen and the plasmid that encodes at least one viral antigen. In a further aspect, one of vector (a) and vector (b) is not an intact, bacterially derived minicell or killed bacterial cell and the other of vector (a) and vector (b) is an intact, bacterially derived minicell or killed bacterial cell.

In all of the compositions described herein, the viral antigen can comprise or characterizes a virus or an immunogenic fragment thereof, wherein the virus is selected from the group consisting of an Alphacoronavirus; a Colacovirus such as Bat coronavirus CDPHE15; a Decacovirus such as Bat coronavirus HKU10 or Rhinolophus ferrumequinum alphacoronavirus HuB-2013; a Duvinacovirus such as Human coronavirus 229E; a Luchacovirus such as Lucheng Rn rat coronavirus; a Minacovirus such as a Ferret coronavirus or Mink coronavirus 1; a Minunacovirus such as Miniopterus bat coronavirus 1 or Miniopterus bat coronavirus HKU8; a Myotacovirus such as Myotis ricketti alphacoronavirus Sax-2011; a nyctacovirus such as Nyctalus velutinus alphacoronavirus SC-2013; a Pedacovirus such as Porcine epidemic diarrhea virus or Scotophilus bat coronavirus 512; a Rhinacovirus such as Rhinolophus bat coronavirus HKU2; a Setracovirus such as Human coronavirus NL63 or NL63-related bat coronavirus strain BtKYNL63-9b; a Tegacovirus such as Alphacoronavirus 1; a Betacoronavirus; a Embecovirus such as Betacoronavirus 1, Human coronavirus OC43, China Rattus coronavirus HKU24, Human coronavirus HKU1 or Murine coronavirus; a Hibecovirus such as Bat Hp-betacoronavirus Zhejiang2013; a Merbecovirus such as Hedgehog coronavirus 1, Middle East respiratory syndrome-related coronavirus (MERS-CoV), Pipistrellus bat coronavirus HKU5 or Tylonycteris bat coronavirus HKU4; a Nobecovirus such as Rousettus bat coronavirus GCCDC1 or Rousettus bat coronavirus HKU9, a Sarbecovirus such as a Severe acute respiratory syndrome-related coronavirus, Severe acute respiratory syndrome coronavirus (SARS-CoV) or Severe acute respiratory syndrome coronavirus 2 (SARS-CoV-2, COVID-19); a Delta coronavirus; an Andecovirus such as Wigeon coronavirus HKU20; a Buldecovirus such as Bulbul coronavirus HKU11, Porcine coronavirus HKU15, Munia coronavirus HKU13 or White-eye coronavirus HKU16; a Herdecoronavirus such as Night heron coronavirus HKU19; a Moordecovirus such as Common moorhen coronavirus HKU21; a Gammacoronavirus; a Cegacovirus such as Beluga whale coronavirus SW1; and an Igacovirus such as Avian coronavirus.

In another aspect, the viral antigen can be encoded by a polynucleotide comprising the sequence of SARS-CoV-2 or a variant thereof, or an antigenic fragment of SARS-CoV-2 or a variant thereof, or a polynucleotide having at least 80% sequence identity to the polynucleotide comprising the sequence of SARS-CoV-2 or a variant thereof. In yet another aspect, the viral antigen can comprise or is characteristic of human coronavirus 229E, human coronavirus OC43, SARS-CoV, HCoV NL63, HKU1, MERS-CoV, or SARS-CoV-2. Further, the viral antigen can comprise or is characteristic of SARS-CoV-2 or a variant thereof.

In one aspect, described herein is a composition comprising: (a) a vector comprising a plasmid that encodes at least one viral antigen, wherein the viral antigen is from a SARS-CoV-2 variant; (b) a vector comprising a CD1d-recognized antigen; and (c) at least one pharmaceutically acceptable carrier, wherein at least one of vector (a) and vector (b) is an intact, bacterially-derived minicell or killed bacterial cell.

In another aspect, the SARS-CoV-2 variant is selected from the group consisting of: (a) UK SARS-CoV-2 variant (B.1.1.7/VOC-202012/01); (b) B.1.1.7 with E484K variant; (c) B.1.617.2 (Delta) variant; (d) B.1.617 variant; (e) B.1.617.1 (Kappa) variant; (f) B.1.617.3 variant; (g) South Africa B.1.351 (Beta) variant; (h) P.1 (Gamma) variant; (i) B.1.525 (Eta) variant; (j) B.1.526 (Iota) variant; (k) Lambda (lineage C.37) variant; (l) Epsilon (lineage B.1.429) variant; (m) Epsilon (lineage B.1.427) variant; (n) Epsilon (lineage CAL.20C) variant; (o) Zeta (lineage P.2) variant; (p) Theta (lineage P.3) variant; (q) R.1 variant; (r) Lineage B.1.1.207 variant; and (s) Lineage B.1.620 variant.

In another aspect, the SARS-CoV-2 variant is selected from the group consisting of a SARS-CoV-2 variant comprising: (a) a L452R Spike Protein Substitution; (b) an E484K Spike Protein Substitution; (c) K417N Spike Protein Substitution; (d) E484K Spike Protein Substitution; (e) N501Y Spike Protein Substitution; (f) K417T Spike Protein Substitution; (g) E484K Spike Protein Substitution; (h) N501Y Spike Protein Substitution; and (h) SARs-CoV-2 variants having one or more of the following missense mutations: N440, L452R, S477G/N, E484Q, E484K, N501Y, D614G, P681H, P681R, and A701V.

In one aspect, the vaccine compositions can comprise a vector comprising at least one viral antigen from a SARS-CoV-2 variant, and further at least one viral antigen from a SARS-CoV-2 strain (e.g., a non-variant). For example, the SARS-CoV-2 strain can be selected from the group consisting of the L strain, the S strain, the V strain, the G strain, the GR strain, and the GH strain. In another aspect, the SARS-CoV-2 viral antigen can be encoded by a polynucleotide comprising the sequence of SARS-CoV-2, or a polynucleotide having at least 80% sequence identity to the polynucleotide comprising the sequence of SARS-CoV-2.

In one aspect of the compositions described herein, the plasmid encodes at least one of spike (S) protein, nucleocapsid (N) protein, membrane (M) protein, and envelope (E) protein of SARS-CoV-2 or a SARS-CoV-2 variant. In addition, the plasmid can encode all of the spike (S) protein, nucleocapsid (N) protein, membrane (M) protein, and the envelope (E) protein of a SARS-CoV-2 strain or variant, or any combination thereof (e.g., a Spike protein from a variant and an envelope protein from a non-variant strain).

In another aspect, the plasmid can encode the receptor binding domain (RBD) of a Spike protein of SARS-CoV-2 or a SARS-CoV-2 variant.

In another aspect, encompassed is a vaccine composition comprising at least one intact, bacterially-derived minicell or killed bacterial cell, and comprised within the minicell or cell: (a) a plasmid encoding a Spike protein from one or more of SARS-CoV-2 variant Alpha (B.1.1.7.UK), SARS-CoV-2 variant Beta (B.1.351. SA), SARS-CoV-2 variant Delta (B.1.617.2 India), and/or SARS-CoV-2 variant Gamma (P.1 Brazil); and (b) α-galactosylceramide. In addition, the vaccine composition can comprise (a) and (b) within a single minicell. Further, plasmid of the vaccine composition can encode the Spike protein from each of SARS-CoV-2 variant Alpha (B.1.1.7.UK), SARS-CoV-2 variant Beta (B.1.351. SA), SARS-CoV-2 variant Delta (B.1.617.2 India), and SARS-CoV-2 variant Gamma (P.1 Brazil).

In one embodiment, the CD1d-recognized antigen comprises a glycosphingolipid. For example, the CD1d-recognized antigen can be selected from the group consisting of α-galactosylceramide (α-GalCer), C-glycosidific form of α-galactosylceramide (α-C-GalCer), 12 carbon acyl form of galactosylceramide (β-GalCer), β-D-glucopyranosylceramide (β-GlcCer), 1,2-Diacyl-3-O-galactosyl-sn-glycerol (BbGL-II), diacylglycerol containing glycolipids (Glc-DAG-s2), ganglioside (GD3), gangliotriaosylceramide (Gg3Cer), glycosylphosphatidylinositol (GPI), α-glucuronosylceramide (GSL-1 or GSL-4), isoglobotrihexosylceramide (iGb3), lipophosphoglycan(LPG), lyosphosphatidylcholine (LPC), α-galactosylceramide analog (OCH), threitolceramide, and a derivative of any thereof.

In another aspect, the CD1d-recognized antigen comprises α-GalCer. In addition, the CD1d-recognized antigen can comprise a synthetic α-GalCer analog. For example, the CD1d-recognized antigen can comprise a synthetic α-GalCer analog selected from 6'-deoxy-6'-acetamide α-GalCer (PBS57), napthylurea α-GalCer (NU-α-GC), NC-α-GalCer, 4ClPhC-α-GalCer, PyrC-α-GalCer, α-carba-GalCer, carba-α-D-galactose α-GalCer analog (RCAI-56), 1-deoxy-neo-inositol α-GalCer analog (RCAI-59), 1-O-methylated α-GalCer analog (RCAI-92), and HS44 aminocyclitol ceramide.

In one aspect, the CD1d-recognized antigen is an IFNγ agonist.

The compositions described herein can be formulated for any pharmaceutically acceptable use. Examples of pharmaceutically acceptable formulations include but are not limited to oral administration, injection, nasal administration, pulmonary administration, or topical administration.

The disclosure also encompasses methods of treating and/or vaccinating against a viral infection, comprising administering to a subject in need a composition described herein.

In one aspect, the subject is suffering from or at risk of developing lymphopenia. In another aspect, the subject is deemed at risk for severe illness and/or serious complications from the viral infection. For example, an "elderly" subject at higher risk for severe illness and/or serious complications from the viral infection is about age 50 or older, about age 55 or older, about age 60 or older, or about age 65 or older.

In another aspect of the methods described herein, the subject suffers from one or more pre-existing conditions selected from the group consisting of diabetes, asthma, a respiratory disorder, high blood pressure, and heart disease. In yet another aspect, the subject is immunocompromised. For example, the subject can be immunocompromised due to AIDS, cancer, a cancer treatment, hepatitis, an autoimmune disease, steroid receiving, immunosenescence, or any combination thereof.

In one embodiment, administration of a composition described herein increases the chance of survival following exposure to a coronavirus. For example, the chance of survival can be increased by about 10%, about 20%, about 30%, about 40%, about 50%, about 60%, about 70%, about 80%, about 90%, or about 100%, as measured using any clinically recognized technique.

In yet another aspect, administration of a composition described herein reduces the risk of transmission of coronavirus. For example, the reduction in risk of transmission can be by about 10%, about 20%, about 30%, about 40%, about 50%, about 60%, about 70%, about 80%, about 90%, or about 100%, as measured using any clinically recognized technique.

In all of the methods described herein, the administration step can be via any pharmaceutically acceptable method.

In another aspect, the subject can be exposed to or is anticipated to be exposed to an individual who is contagious for a coronavirus. In addition, the individual who is contagious for a coronavirus can have one or more symptoms selected from the group consisting of fever, cough, shortness of breath, diarrhea, sneezing, runny nose, and sore throat.

In one embodiment, the subject of the methods described herein is a healthcare worker, aged 60 years or older, frequent traveler, military personnel, caregiver, or a subject with a preexisting condition that results in increased risk of mortality with infection.

In another aspect, the method further comprises administering one or more antiviral drugs. For example, the one or more antiviral drugs can be selected from the group consisting of chloroquine, darunavir, galidesivir, interferon beta, lopinavir, ritonavir, remdesivir, and triazavirin.

In the methods of the disclosure, the CD1d-recognized antigen induces a Th1 cytokine response in the subject. For example, the cytokine can comprise IFNγ.

In another aspect, a first minicell comprising the CD1d-recognized antigen and a second minicell comprising the plasmid encoding at least one viral antigen are administered to the subject simultaneously. In yet another aspect, a first minicell comprising the CD1d-recognized antigen and a second minicell comprising the plasmid encoding at least one viral antigen are administered to the subject sequentially. Alternatively, the disclosure encompasses a method wherein first minicells comprising the CD1d-recognized antigen and second minicells comprising the plasmid encoding at least one viral antigen are administered to the subject repeatedly.

In the methods described herein, first minicells comprising the CD1d-recognized antigen and second minicells comprising the plasmid encoding at least one viral antigen can be administered to the subject at least once a week, twice a week, three times per week, or four times per week.

Both the foregoing summary and the following description of the drawings and detailed description are exemplary and explanatory. They are intended to provide further details of the invention, but are not to be construed as limiting. Other objects, advantages, and novel features will be readily apparent to those skilled in the art from the following detailed description of the invention.

BRIEF DESCRIPTION OF THE DRAWINGS

The patent or application file contains drawings executed in color. Copies of this patent or patent application publication with color drawing(s) will be provided by the Office upon request and payment of necessary fee.

FIG. 1 is a graphical depiction of composition comprising a combination of an EnGeneIC Dream Vehicle (EDV™), i.e., an intact, bacterially derived minicell, loaded with the CD1d-restricted iNKT cell antigen α-galactosylceramide (α-GalCer), which stimulates IFNγ, and a bacterial minicell loaded with a plasmid encoding viral antigens.

FIGS. 2A-2D shows peripheral blood mononuclear cells (PBMCs) from patient 1-CB04-1 (72 year-old male) with end-stage hepatocellular carcinoma, showed an elevation in CD8+ cytotoxic T cells (FIG. 2A), NK cells (FIG. 2B), NKT cells (FIG. 2C) and iNKT cells (FIG. 2D) by cycle 2 and 3 following treatment with EGFR-targeted, PNU-packaged intact, bacterially derived minicells+α-galactosyl ceramide packaged intact, bacterially derived minicells. It is to be noted that the patient is elderly and severely immune-compromised. PNU is PNU-159682, which is a morpholinyl anthracycline derivative.

FIGS. 3A-3C shows PBMCs from a 45 year-old female with end-stage colorectal cancer, showing activation of key immune cells. The patient's CD8+ effector cytotoxic T cells (CD45RA+CCR7−) increased significantly by cycles 2 and 3 (FIG. 3A). Similarly, the subject's PBMCs showed an increase in NK cells (FIG. 3B) by cycles 2 and 3. Interestingly, ELISA analysis of the patient's serum, 3 hrs post each intact, bacterially derived minicell dose, showed a spike in IFNγ (FIG. 3C) which would occur if the α-galactosyl ceramide were effectively presented by antigen presenting cells (APCs) to the iNKT cells which would then trigger off the release of IFNγ, a critical mediator in fighting viral infections.

FIG. 4 shows the white blood cell counts (average of 9 patients) at pre-dose and 3 hrs post dose. 8 out of the 9 patients were elderly and all were severely immune-compromised with Stage IV pancreatic cancer and all having failed all lines of conventional therapy. Yet, interestingly, 3 hrs post dose there was a significant increase in white blood cells (WBC) and this occurred at every dose after dose 2, suggesting that the early doses of intact, bacterially derived minicells recruit fresh monocytes from the bone marrow following activation signals from the macrophages, dendritic cells and NK cells and by dose 3 they are sufficiently activated and matured to result in proliferation.

FIG. 6A shows the results of measuring serum IgG titer at 1 week following administration of various bacterial minicell (EDV) formulations to mice, where it was found that intramuscular (IM) injection of bacterial minicells loaded with Covid-αGC (EDV$_{Covid\text{-}αGC}$), produced the highest S-protein specific IgG titer as compared to subcutaneous (SC) injection. FIG. 6B shows a bar graph of total AUC for IgG at 1 week following administration of various bacterial minicell (EDV) formulations to mice, where AUC analysis showed the highest IgG in IM injected mice.

FIGS. 7A-7E shows that mice injected with EDV$_{covid\text{-}αGC}$ through IM had the highest levels of serum IFNα (FIG. 7A), IFNγ (FIG. 7B), IL12 (FIG. 7C), IL6 (FIG. 7D) and TNFα (FIG. 7E) 8 h post-injection.

FIG. 8E shows an IgG subtype analysis of the EDV$_{covid}$ and EDV$_{covid\text{-}αGC}$.

FIG. 9A. shows a FACS analysis of mouse splenocytes demonstrating that EDV$_{Covid\text{-}αGC}$ injected mice had the highest amount of antigen-specific memory CD137+ CD69+ cytotoxic T-cell at 4 weeks (1 boost at day 21) post-initial injection, e.g., there were significantly high number of CD137+ CD69+ population within the cytotoxic T-cell population in the EDV$_{Covid\text{-}αGC}$ treated mice as compared to all other treatment groups. FIG. 9B shows an AIMS assay demonstrating that bacterial minicells loaded with Covid-αGC (EDV$_{covid\text{-}αGC}$) treated cytotoxic T-cells from the spleen expressed viral antigen-specific CD69 single positive cytotoxic T-cells following stimulation of the spike protein in a similar fashion to that of stimulated using PHA (e.g., when exposed to the spike protein ex vivo). Splenocytes from EDV$_{covid}$ treated mice exhibited a similar characteristic but to a less degree. This was not found in other treatment groups.

FIGS. 12A-12E shows a detailed ELISA analysis of initial interferon response in mouse serum following I.M. injections of EDV, EDV$_{aGC}$, EDV$_{Control}$, EDV$_{Control\text{-}αGC}$, EDV$_{Covid}$, and EDV$_{Covid\text{-}αGC}$. The results demonstrated that the early interferon response in mice was predominantly induced by the administration of αGC carried by EDVs with or without an accompanying antigen-specific plasmid (e.g., administration of EDV$_{aGC}$ with or without the combination of an EDV$_{Plasmid}$), as IM injections resulted in a dramatic increase in IFNα, IFNγ, TNFα, IL12, IL6 8 h post initial treatment. See FIG. 12A (serum IFNα concentration); FIG. 12B (serum IFNγ concentration); FIG. 12C (IL6 serum concentration); FIG. 12D (serum TNFα, concentration); and FIG. 12E (IL12p40 serum concentration).

FIGS. 13A and 13B show a FACS analysis of extracted mouse spleen showed that there is a high percentage of CD3+ CD8+ cytotoxic T-cells in the EDV$_{Covid\text{-}αGC}$ treated mice (FIG. 13A). The stimulation of the splenocytes with Covid-19 spike protein induced the number of CD69+ CD137+ cells within the cytotoxic T-cell population at a greater extend compared to that of stimulated using PHA (+ve control) (FIG. 13B).

FIG. 17A is a graphical depiction of an EDV-COVID-19 vaccine composition, comprising a bacterial expression plasmid ("EDV"), such as that shown in FIG. 16B, wherein the EDV first expresses Spike protein of SARS-CoV-2 in the EDV cytoplasm and additionally carrys or is loaded with the CD1 d-restricted iNKT cell antigen glycolipid α-galactosylceramide (α-GalCer) IFN-γ as an adjuvant or stimulating agent. Expressed Spike protein encoded by SARS-CoV-2 is designated by a star on FIG. 17A. FIG. 17B shows an exemplary vial containing lyophilized EDV-COVID-19 vaccine composition.

FIG. 18 is a graphical depiction of an EDV-COVID-19 vaccine composition, comprising a bacterial expression plasmid ("EDV"), such as that shown in FIG. 16B, wherein the EDV contains (i) a plasmid expressing cloned Spike proteins from original SARS-CoV-2 and multiple genetic variants, such as delta variant and Brazil variant, (ii) a gene expression promotor expressing all proteins as a single mRNA and separate proteins in the EDV cytoplasm, (iii) multiple Spike proteins, including Spike protein produced by SARS-CoV-2, Brazil variant Spike Protein, and delta variant Spike protein, and (iv) the CD1d-restricted iNKT cell antigen glycolipid α-galactosylceramide (α-GalCer) IFN-γ as an adjuvant or stimulating agent. Expressed Spike proteins encoded are designated by stars on FIG. 18.

FIGS. 19A-19C shows the results of administering a bacterial minicell comprising α-galactosylceramide (α-GalCer) to three pancreatic cancer patients (CB03, CB17, and CB41) over a 39 day period, or 4 pancreatic cancer patients (CB11, CB14, CB18, and CB41) over a 46 day period.

Measurement of serum IFN-alpha (pg/mL) (FIG. 19A) and serum IFN-gamma (FIG. 19B) are shown on the Y axis of the graphs depicted in FIGS. 19A and 19B. The data shows that EDV-αGC elicits a Th1 response and increase lymphocyte levels in pancreatic cancer patients. FIG. 19A shows a sustained increase in serum IFNα levels from all 3 patients following 2 doses of EDV-αGC, and FIG. 19B shows a sustained increase in serum IFNγ levels from all 3 patients following 2 doses (one week apart) of EDV-αGC. IFN levels were measured via ELISA from patients' blood serum samples taken throughout treatment cycles. FIG. 19C shows the results of measuring lymphocyte counts ($\times 10^9$/L) for four pancreatic cancer patients (CB11, CB14, CB18, and CB41) over a 46 day period following 2 doses (one week apart) of EDV-αGC. The results depicted in FIG. 19C show a rise in lymphocyte counts to within normal range (1.0-4.0) in the four pancreatic cancer patients. Lymphocyte levels were measured from patient blood samples throughout treatment cycles, by pathology service.

Figure 5:
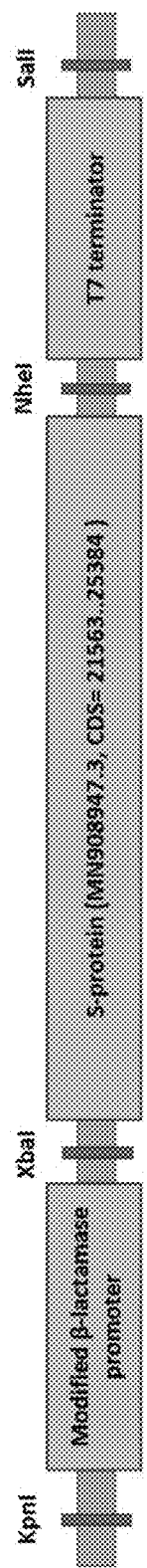
FIG. 5 shows construction of an expression cassette.

A mature SARS-CoV-2 virus has four structural proteins, namely, envelope, membrane, nucleocapsid, and spike. It is believed that all these proteins may serve as antigens to stimulate neutralizing antibodies and increase CD4+/CD8+ T-cell responses.

The composition can be administered via any pharmaceutically acceptable method, such as but not limited to injection (parenteral, intramuscular, intravenous, intraportal, intrahepatic, peritoneal, subcutaneous, intratumoral, or intradermal administration), oral administration, application of the formulation to a body cavity, inhalation, insufflation, nasal administration, pulmonary administration, or any combination of routes also may be employed.

The compositions can be administered to subjects at risk of viral infection as a vaccine, or the compositions can be administered as a therapeutic to a subject who is suffering from a viral infection.

The major areas being currently explored for the treatment/vaccines against SARS-CoV2 include: (1) antiviral drugs (e.g. Gilead Sciences; nucleotide analog Remdesivir); (2) Cocktail monoclonal antibodies (e.g. Regeneron); and (3) Attenuated viruses as vaccines to stimulate a potent antibody response to the viral proteins. Each of these strategies face difficulties but most importantly, none of these approaches is able to solve the problem of lymphopenia in the elderly and immune-compromised patients to be able to overcome the viral infection. In the absence of a robust immune system, this population of patients will still be most vulnerable and likely to succumb to the disease.

A. Immunotherapy Aspects of the Disclosure

Effective immunotherapy strategies for the treatment of diseases such as cancer depend on the activation of both innate and adaptive immune responses. Cells of the innate immune system interact with pathogens via conserved pattern-recognition receptors, whereas cells of the adaptive immune system recognize pathogens through diverse, antigen-specific receptors that are generated by somatic DNA rearrangement. Invariant natural killer T (iNKT) cells are a subset of lymphocytes (Type I NKT) that bridge the innate and adaptive immune systems. iNKT cells express an invariant a chain T cell receptor (Vα24-Jα18 in humans and Vα14-Jα18 in mice) that is specifically activated by certain glycolipids presented in the context of the non-polymorphic MHC class I-like protein, CD1d. CD1d binds to a variety of dialkyl lipids and glycolipids, such as the glycosphingolipid α-galactosylceramide (α-GalCer). iNKT cell TCR recognition of the CD1d-lipid complex results in the release of pro-inflammatory and regulatory cytokines, including the Th1 cytokine interferon gamma (IFNγ). The release of cytokines in turn activates adaptive cells, such as T and B cells, and innate cells, such as dendritic cells and NK cells.

α-GalCer, also known as KRN7000, chemical formula $C_{50}H_{99}NO_9$, is a synthetic glycolipid derived from structure-activity relationship studies of galactosylceramides isolated from the marine sponge *Agelas mauritianus*. α-GalCer is a strong immunostimulant and shows potent anti-tumor activity in many in vivo models. A major challenge to using α-GalCer for immunotherapy is that it induces anergy in iNKT cells because it can be presented by other CD1d expressing cells, such as B cells, in the peripheral blood. Delivery of α-GalCer also has been shown to induce liver toxicity.

In prior EnGeneIC disclosures, the use of plasmid-packaged minicells in the treatment of neoplastic diseases has been demonstrated, where the primary function of the plasmid was to encode siRNAs or miRNAs to silence genes in cancer cells that were responsible for cell proliferation or drug resistance. It has been shown that in the end-stage cancer patients who are highly immuno-compromised, intact bacterial minicell therapy (also referred to as "EnGeneIC Dream Vector™" or EDV™) results in: (1) activation and proliferation of CD8+ T cells, Macrophages, NK cells, Dendritic cells, and iNKT cells. This result is exactly what is desired in a viral vaccine, such as a SARs-CoV-2 therapeutic/vaccine.

In the present disclosure, the function of the plasmid-packaged minicell component of the full composition (which includes a CD1d-recognized antigen such as α-GC-packaged minicell) has a novel function not shown or described before. Specifically, the plasmid is used to encode viral proteins in the parent bacterial cell and the proteins segregate into the minicell at the time of asymmetric cell division. These viral proteins are delivered into the lysosomes of antigen processing and presenting cells (APCs) such as macrophages and dendritic cells. Post-antigen processing, the viral protein epitopes are displayed on the APC surface via MHC Class I and Class II molecules, which is predicted to result in a potent antibody response to the viral proteins. Additionally, the plasmid itself being a double stranded nucleic acid is recognized by nucleic acid sensing proteins in the APC and this then triggers the secretion of Type I interferons (IFNα and IFNβ).

This unique dual trigger of antibody response to viral proteins and Type I interferon response results in not only mopping up viral particles released from infected cells but also results in cells of the immune system being able to recognize virally infected cells and kill them. This dual trigger has not been described before, particularly the ability of Type I interferon to trigger a heretofore uncharacterized mechanism by which virally infected cells can be recognized and killed.

In addition, in the present disclosure, post-presentation of α-GC/CD1d to the iNKT cell receptor, the trigger of IFNγ, is the key to augmenting anti-viral immunity. The exact mechanism of action is unknown, but IFNγ is critical in identifying and destroying virally infected cells.

In the United States, several clinical trials have been conducted where anticancer-agent loaded intact, bacterially derived minicells, and microRNA mimic loaded intact, bacterially derived minicells, have been administered to humans in methods of treating cancer. See, e.g., ClinicalTrials.gov Identifier Nos. NCT02766699, NCT02687386, and NCT02369198. In addition, in Australia a bacterial minicell loaded with α-GC is being administered to patients in a Phase IIa clinical trial in end-stage cancer patients. The results have shown that intact, bacterially derived minicells loaded with alpha-GC are a potent stimulator of IFN-γ. See Trial ID No. ACTRN12619000385145. Thus, in vivo efficacy in humans of intact, bacterially derived minicells loaded with a CD1d-recognized antigen has been shown, and additionally efficacy in humans of intact, bacterially derived minicells loaded with a target compound (e.g., an anticancer compound instead of a viral antigen) has been shown.

Additionally, the disclosed composition has another critical function that allows elderly and immune-compromised patients to recover from lymphopenia (rapid depletion of lymphocytes including macrophages, dendritic cells, NK cells and CD8+ T cells), which is the main reason viruses like SARS-CoV-2 takes over in these patients and they end up with Respiratory distress syndrome and eventual death. Specifically, the bacterial minicells of the composition themselves activate macrophages via recognition of pathogen associated molecular patterns (PAMPs) like LPS. This provides the activation, maturation and proliferation signals to resting monocytes in bone marrow, resulting in a significant increase in activated macrophages and dendritic cells. Additionally, the minicell-associated PAMPs also activate NK cells and these are also provoked into proliferation. Further still, the activated macrophages and dendritic cells home into the infected area and engulf the apoptotic virally infected cells. They then migrate into the draining lymph nodes and activate the naive CD8+ T cells which then get activated and proliferate.

Therefore, the minicell component of the composition, by virtue of the PAMP signals, is able to overcome lymphopenia in elderly and immune-compromised patients, or patients with underlying comorbidities, and the activation of these lymphocytes helps to overcome the viral infection and prevent the patient from tipping over into respiratory distress and death.

II. Background Regarding Viral Infections

The present disclosure is directed to vaccine compositions useful against any viral disease, including but not limited to coronavirus infections.

A. Coronavirus Infections

Coronaviruses are a family of hundreds of viruses that can cause fever, respiratory problems, and sometimes gastrointestinal symptoms. SARS-CoV-2 is one of seven members of this family known to infect humans, and the third in the past three decades to jump from animals to humans. Since emerging in China in December 2019, this new coronavirus has caused a global health emergency.

Patients infected with SARS-CoV or MERS-CoV initially present with mild, influenza-like illnesses with fever, dyspnea, and cough. Most patients recover from this illness. However, the most vulnerable populations are patients over the age of 65 and patients with comorbidities that result in immune-suppression such as cancer, HIV, etc., where the disease progresses to more severe symptoms and is characterized by an atypical interstitial pneumonia and diffuse alveolar damage. Both SARS-CoV and MERS-CoV are capable of causing acute respiratory distress syndrome (ARDS), the most severe form of acute lung injury where alveolar inflammation, pneumonia, and hypoxic lung conditions lead to respiratory failure, multiple organ disease, and death in 50% of ARDS patients. As the disease progresses, lymphopenia is commonly observed. Most of the deaths that occur from CoV-2 infection are a result of the severe lymphopenia in immune-compromised patients and the disease takes over resulting in ARDS.

SARS-CoV-2 (COVID-19) causes atypical pneumonia in infected people and the symptoms include fever, dry cough, and fatigue. Most patients have lymphopenia (drop in white blood cell counts particularly T cells, B cells and NK cells). Current observations indicate that the patients most likely to die from this disease are those that are immune-compromised (elderly and those with immunosuppressive disease, such as cancer) and patients with diabetes and other underlying health conditions, such as high blood pressure, heart disease, and respiratory disorders. The former group of patients most likely succumb due to the lymphopenia and hence the viral replication and infection of both lungs becomes uncontrolled resulting in Acute Respiratory Distress Syndrome (ARDS).

The viral proliferation takes over once the major cells of the immune system e.g. T cells, B cells, macrophages and NK cells are depleted. In elderly patients, immune function is not as robust as it is in younger people. Studies have shown that in most people, their immune function is fine in their 60s, or even in their 70s. The immune functions go down rather quickly after age 75 or 80.

COVID-19 spreads rapidly by human-to-human transmission with a median incubation period of 3.0 days (range, 0 to 24.0) and the time from symptom onset to developing pneumonia is 4.0 days (range, 2.0 to 7.0) (Guan et al., 2020). Fever, dry cough, and fatigue are common symptoms at onset of COVID-19 (Huang et al., 2020). Most patients have lymphopenia and bilateral ground-glass opacity changes on chest CT scans (Huang et al., 2020; Duan and Qin, 2020).

The genomic sequence of the first SARS-CoV-2 (Wuhan-Hu-1) has been completed (Genbank Accession no. MN908947.3; Wu et al., 2020). Large-scale culture of SARS-CoV-2 has been carried out and an inactivated virus vaccine has been prepared through the employment of established physical and chemical methods such as UV light, formaldehyde, and β-propiolactone (Jiang et al., 2005). The development of attenuated-virus vaccines is also possible by screening the serially propagated SARS-CoV-2 with reduced pathogenesis such as induced minimal lung injury, diminished limited neutrophil influx, and increased antiinflammatory cytokine expressions compared with the wild-type virus (Regla-Nava et al., 2015). Both inactivated and attenuated virus vaccines have their own disadvantages and side effects (Table 1; reproduced from Shang et al., 2020).

TABLE 1

Advantages and disadvantages of different vaccine strategies.

| Vaccine strategy | Advantages | Disadvantages | References |
|---|---|---|---|
| Inactivated virus vaccines | Easy to prepare; safety; high-titer neutralizing antibodies | Potential inappropriate for highly immunosuppressed individuals | 25 |
| Attenuated virus vaccines | Rapid development; induce high immune responses | Phenotypic or genotypic reversion possible; can still cause some disease | 25 |

TABLE 1-continued Advantages and disadvantages of different vaccine strategies.

| Vaccine strategy | Advantages | Disadvantages | References |
| --- | --- | --- | --- |
| Subunit vaccines | High safety; consistent production; can induce cellular and humoral immune responses; high-titer neutralizing antibodies | High cost; lower immunogenicity; require repeated doses and adjuvants | 12, 14 |
| Viral vector vaccines | Safety; induces high cellular and humoral immune responses | Possible present pre-existing immunity | 12 |
| DNA vaccines | Easier to design; high safety; high-titer neuralizing antibodies | Lower immune responses in humans; repeated doses may cause toxicity | 23 |
| mRNA vaccines | Easier to design; high degree of adaptability; induce strong immune responses | Highly unstable under physiological conditions | 23 |

Current COVID-19 vaccines being used in at least one region of the world include the Pfizer/BioNTech Comirnaty COVID-19 vaccine, Moderna COVID-19 vaccine (mRNA 1273), Janssen/Ad26.COV 2.S developed by Johnson & Johnson, SII/Covishield and AstraZeneca/AZD1222 vaccines (developed by AstraZeneca/Oxford and manufactured by the State Institute of India and SK Bio respectively), Sinopharm COVID-19 vaccine, produced by Beijing Bio-Institute of Biological Products Co Ltd, subsidiary of China National Biotec Group (CNBG), and the Sinovac Biotech Ltd. CoronaVac COVID-19 Vaccine.

None of these therapies are likely to stall the death of immune-compromised patients who get infected just as is currently seen in the case of influenza virus infected patients. Each year the largest number of deaths from flu infections occurs in immune-compromised patients and the elderly.

All new therapies under development are (i) anti-viral drugs to stem the proliferation of the virus systemically or (ii) attenuated viruses as vaccines to stimulate a potent antibody response to the viral proteins.

B. Background Regarding Coronaviruses and SARS-CoV-2

The coronaviral genome encodes four major structural proteins: the spike (S) protein, nucleocapsid (N) protein, membrane (M) protein, and the envelope (E) protein, all of which are required to produce a structurally complete viral particle. Some CoVs do not require the full ensemble of structural proteins to form a complete, infectious virion, suggesting that some structural proteins might be dispensable or that these CoVs might encode additional proteins with overlapping compensatory functions. Individually, each protein primarily plays a role in the structure of the virus particle, but they are also involved in other aspects of the replication cycle. The S protein mediates attachment of the virus to the host cell surface receptors and subsequent fusion between the viral and host cell membranes to facilitate viral entry into the host cell. In some CoVs, the expression of S at the cell membrane can also mediate cell-cell fusion between infected and adjacent, uninfected cells. This formation of giant, multinucleated cells, or syncytia, has been proposed as a strategy to allow direct spreading of the virus between cells, subverting virus-neutralising antibodies.

Figure 22:
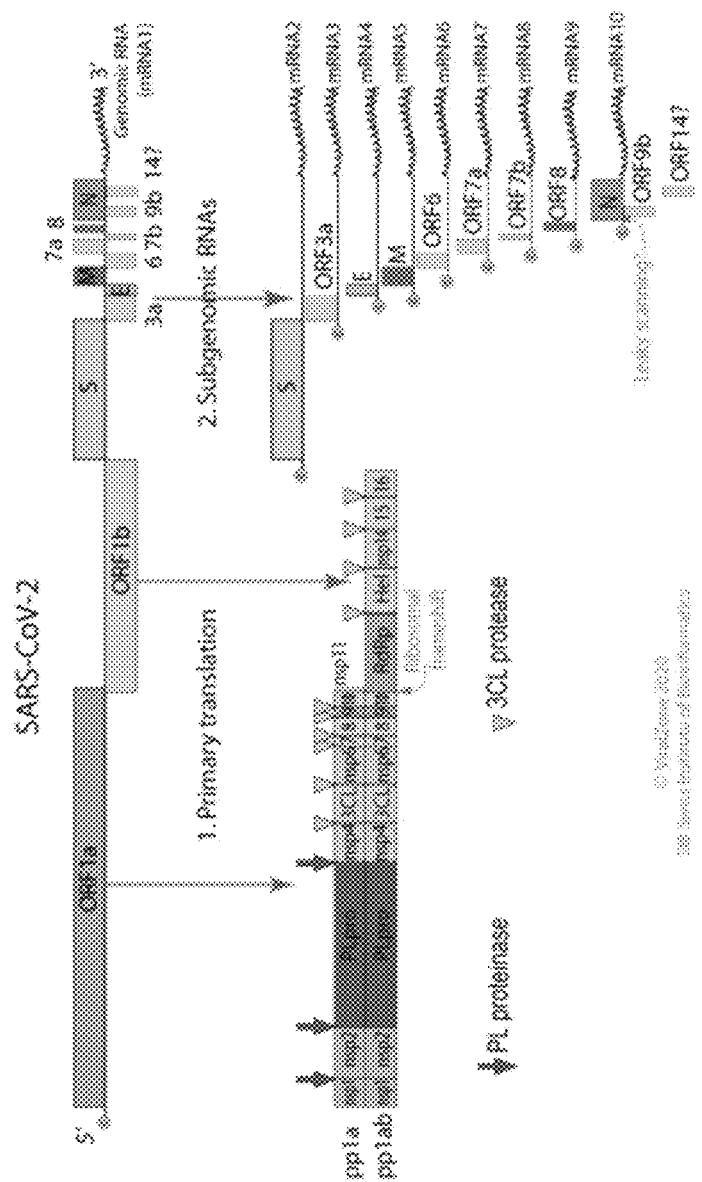

FIG. 22 shows the genome of the SARS-CoV-2 virus, identifying transcription sites and protein coding domains. www.viralzone.espasy.ort/resources/nCoV_genome_bi-s.png.

It has been shown that the SARS-CoV-2 spike (S) glycoprotein binds to the cell membrane protein angiotensin-converting enzyme 2 (ACE2) to enter human cells. COVID-19 has been shown to bind to ACE2 via the S protein on its surface. During infection, the S protein is cleaved into subunits, S1 and S2. S1 contains the receptor binding domain (RBD) which allows coronaviruses to directly bind to the peptidase domain (PD) of ACE2. S2 then likely plays a role in membrane fusion.

Unlike the other major structural proteins, N is the only protein that functions primarily to bind to the CoV RNA genome, making up the nucleocapsid. Although N is largely involved in processes relating to the viral genome, it is also involved in other aspects of the CoV replication cycle and the host cellular response to viral infection. Transient expression of N was shown to substantially increase the production of virus-like particles (VLPs) in some CoVs, suggesting that it might not be required for envelope formation, but for complete virion formation instead.

The M protein is the most abundant structural protein and defines the shape of the viral envelope. It is also regarded as the central organizer of CoV assembly, interacting with all other major coronaviral structural proteins. Homotypic interactions between the M proteins are the major driving force behind virion envelope formation but, alone, is not sufficient for virion formation. Binding of M to N stabilises the nucleocapsid (N protein-RNA complex), as well as the internal core of virions, and, ultimately, promotes completion of viral assembly. Together, M and E make up the viral envelope and their interaction is sufficient for the production and release of VLPs.

The CoV envelope (E) protein is the smallest of the major structural proteins. It is an integral membrane protein involved in several aspects of the virus' life cycle, such as assembly, budding, envelope formation, and pathogenesis. During the replication cycle, E is abundantly expressed inside the infected cell, but only a small portion is incorporated into the virion envelope. The majority of the protein is localised at the site of intracellular trafficking, where it participates in CoV assembly and budding. Recombinant CoVs lacking E exhibit significantly reduced viral titers, crippled viral maturation, or yield propagation incompetent progeny, demonstrating the importance of E in virus production and maturation.

Coronaviruses are viruses whose genome is a single-stranded mRNA, complete with a 3'-UTR and poly-A tail. In a subset of coronaviruses that include 2019-nCoV, SARS and MERS, the3'-UTR contains a highly-conserved sequence (in an otherwise rather variable message) that folds into a unique structure, called the s2m (stem two motif). Although the s2m appears to be extremely conserved in sequence, and is required for virus viability, its exact function is not known. The 2019 Wuhan Novel Coronavirus (COVID-19, formerly 2019-nCoV) possesses almost exactly the same s2m sequence (and therefore structure) as SARS.

SARS-CoV-2 genome sequences are being released and have been published on https://www.nebi.nlm.nih.gov/genbank/sars-cov-2-seqs/(downloaded on Mar. 24, 2020), including the multiple complete nucleotide sequences from viruses around the world, as well as sequences of particular viral genes, such as the S gene, N gene, M gene, etc. Examples include GenBank accession numbers MN908947.3, MN975262.1, NC_045512.2, MN997409.1, MN985325.1, MN988669.1, MN988668.1, MN994468.1, MN994467.1, MN988713.1, and MN938384.1. SARS-CoV-2, is an enveloped, single- and positive-stranded RNA virus with a genome comprising 29,891 nucleotides, which encode the 12 putative open reading frames responsible for the synthesis of viral structural and nonstructural proteins (Wu et al., 2020; Chen et al., 2020). A mature SARS-CoV-2 has four structural proteins, namely, envelope, membrane, nucleocapsid, and spike (Chen et al., 2020). All of these proteins may serve as antigens to stimulate neutralizing antibodies and increase CD4+/CD8+ T-cell responses (Jiang et al., 2015). However, subunit vaccines require multiple booster shots and suitable adjuvants to work, and certain subunit vaccines such as hepatitis B surface antigen, PreS1, and PreS2 may fail to yield protective response when tested clinically. The DNA and mRNA vaccines that are easier to design and proceed into clinical trials very quickly remain experimental. The viral vector-based vaccines could also be quickly constructed and used without an adjuvant. However, development of such vaccines might not start until antigens containing the neutralizing epitopes are identified. The E and M proteins have important functions in the viral assembly of a coronavirus, and the N protein is necessary for viral RNA synthesis. Deletion of E protein abrogated the virulence of CoVs, and several studies have explored the potential of recombinant SARS-CoV or MERS-CoV with a mutated E protein as live attenuated vaccines. The M protein can augment the immune response induced by N protein DNA vaccine against SARS-CoV; however, the conserved N protein across CoV families implies that it is not a suitable candidate for vaccine development, and the antibodies against the N protein of SARS-CoV-2 do not provide immunity to the infection. The critical glycoprotein S of SARS-CoV-2 is responsible for virus binding and entry. The S precursor protein of SARS-CoV-2 can be proteolytically cleaved into S1 (685 aa) and S2 (588 aa) subunits. The S2 protein is well conserved among SARS-CoV-2 viruses and shares 99% identity with that of bat SARS-CoVs. The vaccine design based on the S2 protein may boost the broad-spectrum antiviral effect and is worth testing in animal models. Antibodies against the conserved stem region of influenza hemagglutinin have been found to exhibit broadly cross-reactive immunity, but are less potent in neutralizing influenza A virus. In contrast, the S1 subunit consists of the receptor-binding domain (RBD), which mediates virus entry into sensitive cells through the host angiotensin-converting enzyme 2 (ACE2) receptor. The S1 protein of 2019-nCoV shares about 70% identity with that of human SARS-CoVs. The highest number of variations of amino acids in the RBD is located in the external subdomain, which is responsible for the direct interaction between virus and host receptor.

C. SARS-CoV-2 Variants

According to the US Centers for Disease Control and Prevention (CDC), a SARS-CoV-2 variant has one or more mutations that differentiate it from other variants in circulation. As expected, multiple variants of SARS-CoV-2 have been documented in the United States and globally throughout this pandemic. To inform local outbreak investigations and understand national trends; scientists compare genetic differences between viruses to identify variants and how they are related to each other. The US Department of Health and Human Services (HHS) established a SARS-CoV-2 Interagency Group (SIG) to improve coordination among the CDC, National Institutes of Health (NIH), Food and Drug Administration (FDA), Biomedical Advanced Research and Development Authority (BARDA), and Department of Defense (DoD). This interagency group is focused on the rapid characterization of emerging variants and actively monitors their potential impact on critical SARS-CoV-2 countermeasures, including vaccines, therapeutics, and diagnostics.https://www.cdc.gov/coronavirus/2019-ncov/variants/variant-info.html (accessed on Jul. 21, 2021).

Genetic variants of SARS-CoV-2 have been emerging and circulating around the world throughout the COVID-19 pandemic. Viral mutations and variants in the United States are routinely monitored through sequence-based surveillance, laboratory studies, and epidemiological investigations.

Infection and inoculation both elicit an immune response against Covid-19 that lasts for months and possibly years, a growing body of research shows, but the power of vaccines against known variants make the shots critical to containing the virus. Variants including the Delta strain that is now t in the U.S. can partially evade the immune response from prior infection and vaccination, recent research shows. Full vaccination still appears to offer solid protection against them. The combination of immunity from infection and vaccination will likely serve as a buffer as the Delta variant takes hold in the U.S., epidemiologists say. But there is still opportunity for the virus to spread. *Wall Street Journal*, "COVID-19 Immune Response Could be Long Lasting, but Variants Present Risks" (Jul. 16, 2021).

A US government SARS-CoV-2 Interagency Group (SIG) interagency group developed a Variant Classification scheme that defines three classes of SARS-CoV-2 variants: (1) SARS-CoV-2 Variant of Interest; (2) SARS-CoV-2 Variant of Concern; and (3) SARS-CoV-2 Variant of High Consequence A SARS-CoV-2 "variant of interest" is defined by the CDC as a variant with specific genetic markers that have been associated with changes to receptor binding, reduced neutralization by antibodies generated against previous infection or vaccination, reduced efficacy of treatments, potential diagnostic impact, or predicted increase in transmissibility or disease severity.

Possible attributes of a VOI include, for example, specific genetic markers that are predicted to affect transmission, diagnostics, therapeutics, or immune escape, and/or evidence that it is the cause of an increased proportion of cases or unique outbreak clusters.

SARS-CoV-2 Variants of Interest (VOI) include B.1.427 (Pango lineage), which has Spike Protein Substitutions: L452R, D614G, and has been named "Epsilon." It was first identified in the United States (California). Notable attributes include about 20% increased transmission and a modest decrease in susceptibility to the combination of bamlanivimab and etesevimab; however, the clinical implications of this decrease are not known. Alternative monoclonal antibody treatments are available, and the variant exhibits reduced neutralization by convalescent and post-vaccination sera. This variant was deescalated from a VOC on Jun. 29, 2021, due to the significant decrease in the proportion of B.1.427 lineage viruses circulating nationally and available data indicating that vaccines and treatments are effective against this variant.

A second SARS-CoV-2 VOI is B.1.429 (Pango lineage), which has Spike Protein Substitutions: S131, W152C, L452R, D614G, and has been named "Epsilon". Notable attributes include about 20% increased transmission and reduced susceptibility to the combination of bamlanivimab and etesevimab; however, the clinical implications of this decrease are not known. Alternative monoclonal antibody treatments are available, and the variant exhibits reduced neutralization by convalescent and post-vaccination sera. This variant was deescalated from a VOC on Jun. 29, 2021, due to the significant decrease in the proportion of B.1.429 lineage viruses circulating nationally and available data indicating that vaccines and treatments are effective against this variant.

A third SARS-CoV-2 VOI is B.1.525 (Pango lineage), which has Spike Protein Substitutions: A67V, 69del, 70del, 144del, E484K, D614G, Q677H, F888L, designed "Eta." The variant was first identified in the United Kingdom/ Nigeria—December 2020. Notable attributes include a potential reduction in neutralization by some Emergency Use Authorization (EUA) monoclonal antibody treatments, and a potential reduction in neutralization by convalescent and post-vaccination sera.

A fourth SARS-CoV-2 VOI is B.1.526 (Pango lineage), which has Spike Protein Substitutions: L5F, (D80G*), T95I, (Y144-*), (F157S*), D253G, (L452R*), (S477N*), E484K, D614G, A701V, (T859N*), (D950H*), (Q957R*), and is named "Iota." The variant was first identified in the United States (New York)—November 2020. Notable attributes include reduced susceptibility to the combination of bamlanivimab and etesevimab monoclonal antibody treatment; however, the clinical implications of this are not known. Alternative monoclonal antibody treatments are available, and the variant exhibits reduced neutralization by convalescent and post-vaccination sera. B.1.526.1 sublineage has been consolidated with this parent lineage.

A fifth SARS-CoV-2 VOI is B.1.617.1 (Pango lineage), which has Spike Protein Substitutions: (T95I), G142D, E154K, L452R, E484Q, D614G, P681R, Q1071H, and is named "Kappa." The variant was first identified in India— December 2020. Notable attributes include potential reduction in neutralization by some EUA monoclonal antibody treatments, and potential reduction in neutralization by post-vaccination sera.

A sixth SARS-CoV-2 VOI is B.1.617.3 (Pango lineage), which has Spike Protein Substitutions: T19R, G142D, L452R, E484Q, D614G, P681R, D950N, and is named "20A." The variant was first identified in India—October 2020. Notable attributes include potential reduction in neutralization by some EUA monoclonal antibody treatments, and potential reduction in neutralization by post-vaccination sera.

A SARS-CoV-2 "Variant of Concern" (VOC) is defined by the CDC as a variant for which there is evidence of an increase in transmissibility, more severe disease (e.g., increased hospitalizations or deaths), significant reduction in neutralization by antibodies generated during previous infection or vaccination, reduced effectiveness of treatments or vaccines, or diagnostic detection failures.

Possible attributes of a VOC include, in addition to the possible attributes of a VOI, (a) Evidence of impact on diagnostics, treatments, or vaccines; (b) Widespread interference with diagnostic test targets; (c) Evidence of substantially decreased susceptibility to one or more class of therapies; (d) Evidence of significant decreased neutralization by antibodies generated during previous infection or vaccination; (e) Evidence of reduced vaccine-induced protection from severe disease; (f) Evidence of increased transmissibility; and (g) Evidence of increased disease severity.

A first VOC is B.1.1.7 (Pango lineage), which has Spike Protein Substitutions: 69del, 70del, 144del, (E484K*), (S494P*), N501Y, A570D, D614G, P681H, T716I, S982A, D1118H (K1191N*), and is named "Alpha." The variant was first identified in the United Kingdom, and notable attributes include (1) ~50% increased transmission, (2) potential increased severity based on hospitalizations and case fatality rates, (3) no impact on susceptibility to EUA monoclonal antibody treatments, and (4) minimal impact on neutralization by convalescent and post-vaccination sera.

A second VOC is B.1.351 (Pango lineage), which has Spike Protein Substitutions: D80A, D215G, 241del, 242del, 243del, K417N, E484K, N501Y, D614G, A701V, and is named "Beta." The variant was first identified in South Africa, and notable attributes include (1) ~50% increased transmission, (2) significantly reduced susceptibility to the combination of bamlanivimab and etesevimab monoclonal antibody treatment, but other EUA monoclonal antibody treatments are available, and (3) reduced neutralization by convalescent and post-vaccination sera.

A third VOC is B.1.617.2 (Pango lineage), which has Spike Protein Substitutions: T19R, (V70F*), T95I, G142D, E156-, F157-, R158G, (A222V*), (W258L*), (K417N*), L452R, T478K, D614G, P681R, D950N, and is named "Delta." The variant was first identified in India, and notable attributes include (1) increased transmissibility, (2) potential reduction in neutralization by some EUA monoclonal antibody treatments, and (3) potential reduction in neutralization by post-vaccination sera. AY.1, AY.2 and AY.3 are currently aggregated with B.1.617.2.

A third VOC is P.1 (Pango lineage), which has Spike Protein Substitutions: L18F, T20N, P26S, D138Y, R190S, K417T, E484K, N501Y, D614G, H655Y, T1027I, and is named "Gamma." The variant was first identified in Japan/ Brazil, and notable attributes include (1) significantly reduced susceptibility to the combination of bamlanivimab and etesevimab monoclonal antibody treatment, but other EUA monoclonal antibody treatments are available, and (2) reduced neutralization by convalescent and post-vaccination sera.

Finally, a SARS-CoV-2 "variant of high consequence" (VHC) is defined by the CDC as a variant that has clear evidence that prevention measures or medical countermeasures (MCMs) have significantly reduced effectiveness relative to previously circulating variants. Possible attributes of a VHC include, in addition to the possible attributes of a VOC, include the following impact on Medical Countermeasures (MCM), (1) demonstrated failure of diagnostics, (2) evidence to suggest a significantly reduction in vaccine effectiveness, a disproportionately high number of vaccine breakthrough cases, or very low vaccine-induced protection against severe disease, (3) significantly reduced susceptibility to multiple Emergency Use Authorization (EUA) or approved therapeutics, and (4) more severe clinical disease and increased hospitalizations. A VHC would require notification to WHO under the International Health Regulations, reporting to CDC, an announcement of strategies to prevent or contain transmission, and recommendations to update treatments and vaccines. Currently, there are no SARS-CoV-2 variants that rise to the level of high consequence.

As of Jun. 28, 2021, it has been reported that there are four notable SARS-CoV-2 variants in the US: B.1.1.7 (Alpha), B.1.351 (Beta), P.1 (Gamma), and B.1.617.2 (Delta). "About Variants of the Virus that Causes COVID-19", www.cdc.gov/coronavirus/2019-ncov/variants/variant.html (Jun. 28, 2021).

B.1.1.7 (Alpha) variant was first detected in the United States in December 2020. It was initially detected in the United Kingdom. Alpha. (B.1.1.7) COVID-19 variant appears to spread more easily, with about a 50% increase in transmission as compared to previous circulating variants. This variant also might have an increased risk of hospitalization and death. www.mayoclinic.org/diseases-conditions/coronavirus/expert-answers/covid-variant/faq-20505779 (accessed on Jul. 16, 2021).

B.1.351 (Beta) variant was first detected in the United States at the end of January 2021. It was initially detected in South Africa in December 2020. Beta (B.1.351) variant appears to spread more easily, with about a 50% increase in transmission as compared to previous circulating variants. It also reduces the effectiveness of some monoclonal antibody medications and the antibodies generated by a previous COVID-19 infection or COVID-19 vaccine. www.mayoclinic.org/diseases-conditions/coronavirus/expert-answers/covid-variant/faq-20505779 (accessed on Jul. 16, 2021).

P.1 (Gamma) variant was first detected in the United States in January 2021. P.1 was initially identified in travelers from Brazil, who were tested during routine screening at an airport in Japan, in early January. Gamma (P.1) variant reduces the effectiveness of some monoclonal antibody medications and the antibodies generated by a previous COVID-19 infection or a COVID-19 vaccine. www.mayoclinic.org/diseases-conditions/coronavirus/expert-answers/covid-variant/faq-20505779 (accessed on Jul. 16, 2021).

Finally, B.1.617.2 (Delta) variant was first detected in the United States in March 2021. It was initially identified in India in December 2020. Based on current data, variant B.1.1.7 (Delta) is the most common variant across the US. Id. B.1.1.7 (Delta) variant potentially spreads more easily than other variants. Research has shown that it spreads easily in indoor sports settings and households. This variant also might reduce the effectiveness of some monoclonal antibody treatments and the antibodies generated by a COVID-19 vaccine. www.mayoclinic.org/diseases-conditions/coronavirus/expert-answers/covid-variant/faq-20505779 (accessed on Jul. 16, 2021).

These variants seem to spread more easily and quickly than other variants, which may lead to more cases of COVID-19. Id. An increase in the number of cases will put more strain on healthcare resources, lead to more hospitalizations, and potentially more deaths. "About Variants of the Virus that Causes COVID-19", www.cdc.gov/coronavirus/2019-ncov/variants/variant.html (Jun. 28, 2021).

Different variants have emerged in Brazil, California and other areas. A variant called B.1.351, which first appeared in South Africa, may have the ability to re-infect people who have recovered from earlier versions of the coronavirus. It might also be somewhat resistant to some of the coronavirus vaccines in development. Still, other vaccines currently being tested appear to offer protection from severe disease in people infected with B.1.351. www.hopkinsmedicine.org/health/conditions-and-diseases/coronavirus/a-new-strain-of-coronavirus-what-you-should-know (accessed on Jul. 16, 2021).

III. Overview of how the Disclosed Compositions Function to Treat and/or Vaccinate Against Viral Infections The present invention aims to intervene pre-infection, or at an early stage post-infection, with a virus, which can be but is not limited to a coronavirus such as SARS-CoV or MERS-CoV. The compositions and methods address issues including (i) overcoming lymphopenia to prevent the viral infection/disease from overtaking a patient's own immune defences, (ii) stimulating a high titer of systemic antibodies to proteins exposed on the surface of the virus to rapidly mop up viral particles released from infected cells and thereby limit the infection of other healthy cells, and (iii) stimulating a potent Type I and Type II interferon response, which is well known to rapidly combat a range of different viral infections through a plethora of effects such as specific stimulation of antiviral immunity and virally infected cell elimination.

To address these and other needs, the present disclosure provides, in accordance with one aspect, a composition comprising a combination of (i) a vector, which can be intact bacterial-derived minicells which are optionally recombinant, packaged with a plasmid encoding at least one viral protein which functions to stimulate an antibody response to the viral protein and stimulate Type I interferons; (ii) a vector, which can be intact bacterially-derived minicells which are optionally recombinant, packaged with a CD1d-recognized antigen, and (iii) at least one pharmaceutically acceptable carrier. The vector packaged with a CD1d-recognized antigen, such as α-GalCer, functions to stimulate Type II interferon. Further, the minicell vector itself functions to stimulate the activation, maturation and proliferation of cells of the immune system. In another aspect, the intact bacterially-derived minicells can also be replaced with killed bacterial cells.

Thus, as described herein, in certain embodiments the disclosure encompasses compositions comprising an immunogenically effective amount of a combination of (a) a vector or intact, bacterially derived minicells or killed bacterial cells that encapsulate one or more viral antigens and a plasmid and (b) a vector or intact, bacterially derived minicells or killed bacterial cells that encapsulate a CD1d-recognized antigen, such as α-galactosylceramide (α-GalCer). In some embodiments, the encapsulated CD1d-recognized antigen is capable of uptake by a phagocytic cell, such as a dendritic cell or a macrophage. Following uptake, the CD1d-recognized cell antigen form complexes with CD1d within the lysosomes of the phagocytic cells and is subsequently transported to the surface of the phagocytic cells where the CD1d-recognized antigen bound to CD1d is presented for recognition by an iNKT cell. In some embodiments, the CD1d-recognized cell antigen induces a Th1 cytokine response particularly IFNγ by an iNKT cell that recognizes the CD1d-recognized cell antigen bound to CD1d on the surface of the phagocytic cell. IFNγ is also known to trigger a potent antiviral immune response. The ability of CD1d-restricted NKT cells to activate innate and adaptive immune responses has led to the idea that these cells can modulate immunity to infectious agents. In addition, CD1d-restricted iNKT cells may directly contribute to host resistance as they express a variety of effector molecules that could mediate an antimicrobial effect. The CD1 proteins are antigen-presenting molecules that present lipid antigens to T cells.

In one aspect, the intent of administering a composition described herein to a subject in need would be to rapidly lift the subject out of lymphopenia and simultaneously activate the key cells of the immune system to fight against the virus infection, particularly in elderly and immune-compromised patients. This would prevent exacerbation of the viral infection and resultant death of these patients. Consequently, infected subjects would suffer milder flu-like symptoms and recover more rapidly as the body's own immune system tips the balance over to recovery.

In one aspect of the disclosure, all four SARS-CoV-2 structural protein (Envelope, Membrane, Nucleocapsid and Spike) encoding genes are cloned in a plasmid that carries a bacterial origin of replication and the genes are transcribed using a bacterial gene expression promoter so that the proteins are only expressed in the EDV™-producing bacterial cell and segregated into the EDV™ cytoplasm. Thus, all four of the SARS-CoV-2 proteins can be expressed from a single bacterial expression promoter. Alternatively, the genes can be transcribed under a mammalian gene expression promoter so the proteins are expressed only by mammalian cells. The recombinant plasmid can be transformed into a minicell producing strain of *Salmonella typhimurium*. Such a recombinant intact, bacterially derived minicell therapeutic is expected to elicit a potent antibody response to all four CoV-2 proteins.

Additionally, when the recombinant intact, bacterially derived minicells are administered systemically in a SARS-CoV-2 virus infected patient, the intact, bacterially derived minicells are rapidly taken up by professional phagocytic cells such as macrophages and dendritic cells and the intact, bacterially derived minicells are broken down in the lysosomes releasing the plasmid DNA. This DNA is then recognized by intracellular DNA sensors like cGAS, AIM2, IFI16 and others and this will trigger a Type I interferon (IFN$\alpha$ and IFN$\beta$) response. These interferons are known to be potent inducers of antiviral defence.

Immunologists and health authorities caution that not everyone generates a robust immune response following a Covid-19 infection, especially people who are older or have weakened immune systems. Immune response also likely depends on how much virus a person was exposed to or how ill they became. Vaccines appear to confer more consistent protection than infection. Wall Street Journal, "COVID-19 Immune Response Could be Long Lasting, but Variants Present Risks" (Jul. 16, 2021). Many people who are immunocompromised fail to elicit a strong immune response even after full vaccination. Israel has started giving booster shots to people with weaker immune systems as cases caused by the Delta variant increase in the country. Id. An advisory panel to the CDC is scheduled to discuss the potential for additional doses for immunocompromised individuals next week. Id. Thus, there is a particular need for a vaccine that would be effective for this at-risk patient population.

The SARS-CoV-2 vaccine compositions described herein can comprise at least one antigen from a SARS-CoV-2 variant, and in other aspects can comprise at least one antigen from multiple SARS-CoV-2 variants (e.g., Alpha, Beta, Gamma, Delta). The vaccine compositions can additionally comprise a SARS-CoV-2 antigen from a non-variant SARS-CoV-2 strain.

In one aspect, a Spike protein antigen from a SARS-CoV-2 variant is utilized in the compositions described herein. As noted above, the compositions can additionally comprise a viral antigen from a SARS-CoV-2 non-variant strain.

In another aspect, the SARS-CoV-2 antigen, either from a variant or non-variant strain, can be the receptor binding domain (RBD) of a Spike proteins, i.e., the site that is involved in binding to the human ACE2 receptor.

In one aspect, the vaccine compositions described herein comprise, within a single minicell, a bacterial gene expression plasmid encoding at least one SARS-CoV-2 antigen, such as a Spike protein, Spike protein (or other SARS-CoV-2 antigen) expressed by the plasmid, and $\alpha$-galactosyl ceramide as an adjuvant that elicits an IFN$\gamma$ response. In other aspects, the plasmid can encode more than one SARS-CoV-2 antigen, such as Spike proteins from a SARS-CoV-2 variant (e.g., Alpha, Beta, Gamma, Delta, or other variants described herein or as yet unidentified) as well as from a SARS-CoV-2 strain.

In other aspects, the disclosure encompasses a composition comprising a first minicell comprising $\alpha$-galactosyl ceramide as an adjuvant that elicits an IFN$\gamma$ response and a second minicell comprising a bacterial gene expression plasmid encoding at least one SARS-CoV-2 antigen, such as a Spike protein, and Spike protein (or other SARS-CoV-2 antigen) expressed by the plasmid. Again, in other aspects, the plasmid can encode more than one SARS-CoV-2 antigen, such as Spike proteins from a SARS-CoV-2 variant (e.g., Alpha, Beta, Gamma, Delta, or other variants described herein or as yet unidentified) as well as from a SARS-CoV-2 strain.

Unlike current COVID-19 vaccines, the bacterial minicell coronavirus vaccine is expected to be effective against COVID-19 variants, both present variants as well as emergent variants. This is because, as described herein, the design of the bacterial minicell coronavirus vaccines results in broad antiviral effectiveness, which is in contrast to all COVID-19 vaccines currently being used. Effectiveness against variants is critical for the long term success and management of the COVID-19 pandemic.

Exemplary advantages of the present vaccine compositions described herein over other COVID-19 vaccines are detailed in Table 2 below.

TABLE 2

|  | EDV-COVID-19 Therapeutic vaccine | Other vaccines e.g. Pfizer-BioNTech, Moderna, Regeneron |
|---|---|---|
| Anti-spike protein serum IgG & IgM response | Yes | Yes |
| Anti-spike protein nasal and oral mucosa secretory IgA response with intranasal delivery | Yes | No |
| Anti-viral IFN-$\alpha$ & IFN-$\beta$ response | Yes | Only some e.g. those carrying nucleic acids like mRNA |
| Anti-viral IFN-$\gamma$ response | Yes | No |
| Alleviation of lymphopenia especially in elderly | Yes | No |
| Activation of WBC to fight viral infection | Yes | Only some |
| CD8+ cytotoxic T cell & iNKT cell response specific to SARS-CoV-2 | Yes | No. Some capable of CD8+ T cell responses. |
| Can be effective in immuno-compromised patients e.g. cancer | Yes | No |
| Can be effective in elderly with co-morbidities | Yes | Only some |
| Toxicity | None | Some patients with severe toxicity |

TABLE 2-continued

|  | EDV-COVID-19 Therapeutic vaccine | Other vaccines e.g. Pfizer-BioNTech, Moderna, Regeneron |
| --- | --- | --- |
| Can it be effective in patients with auto-antibodies to IFNα | Yes. Because it also provokes IFNβ and IFNγ anti-viral responses | No. Because they do not elicit other anti-viral interferon responses |
| Can the vaccine be readily altered to cover emerging mutant SARS-CoV-2 viruses | Yes. Simply add a new plasmid to the EDV which carries gene sequences for the mutant proteins. Multiple sequences can be carried by the same plasmid | No. Completely new vaccines have to be engineered. |
| Does it work as a vaccine as well as a therapeutic | Yes | No - One or the other |
| Storage & transport issues | No problems. Can be stored & transported at room temperature. | Serious issue. Storage and transport at −20° C. to −70° C. |
| Shelf life | Over 3 years | 2 months to 6 months |
| Cost of product | Inexpensive to make. Affordable world-wide | Some quite expensive & prohibitive in many countries. |

FIGS. 1, 17 and 18 depict various exemplary vaccine constructs according to the disclosure. A first construct (FIG. 17) shows a typical EDV-COVID-19 vaccine composition comprising a bacterial minicell containing a combination of (i) a bacterial gene expression plasmid encoding the SAR-CoV-2 Spike protein, (ii) a Spike protein expressed by the plasmid, and (iii) a glycolipid α-galactosyl ceramide as an adjuvant that elicits an IFNγ response. The second construct (FIG. 18) shows a graphical depiction of an EDV-COVID-19 vaccine composition comprising a bacterial expression plasmid containing a combination of (i) a plasmid expressing cloned Spike proteins from original SARS-CoV-2 and multiple genetic variants, such as delta variant and Brazil variant, (ii) a gene expression promotor expressing all proteins as a single mRNA and separate proteins in the EDV cytoplasm, (iii) multiple Spike proteins, including Spike protein produced by SARS-CoV-2, Brazil variant Spike Protein, and delta variant Spike protein, and (iv) the CD1d-restricted iNKT cell antigen glycolipid α-galactosylceramide (α-GalCer) as an adjuvant or IFN-γ stimulating agent. Expressed Spike proteins encoded are designated by stars on FIG. 18.

A key point of these exemplary constructs is that the plasmids are bacterial expression with bacterial origin of replication, and therefore they do not replicate in human cells and do not integrate into the chromosome. The plasmids remain episomal and degrade when the cell completes its life span.

In another aspect of the disclosure, the vaccine compositions described herein comprise one or more minicells comprising a plasmid having a bacterial gene expression promoter which produces the SARS-CoV-2 antigen (e.g., Spike protein or other SARS-CoV-2 antigen) in the parent bacterial strain and which then segregates into the recombinant minicell. Therefore, in one aspect the composition carries the plasmid, Spike proteins (or other SARS-CoV-2 antigen) and α-galactosyl ceramide in the same minicell or in multiple minicells.

In another aspect, the plasmid can carry a mammalian gene expression promoter so the Spike proteins are only expressed in the human professional phagocytic cells once the minicells have been phagocytosed, plasmid released and mRNA expressed in the mammalian cell nucleus. Therefore, this composition differs from the composition described above since this minicell composition carries the recombinant plasmid with a mammalian gene expression promoter and Spike protein genes (or other SARS-CoV-2 antigen) from SARS-CoV-2 and mutant or variant SARS-CoV-2 cloned downstream of the promoter and α-galactosyl ceramide. Therefore, in this vaccine composition, the Spike proteins are missing in the minicell.

The plasmid can also be a mammalian expression plasmid, where the gene expression promoter can be a mammalian expression promoter. Therefore, the Spike proteins are not produced in the EDV cytoplasm. Instead, when the EDVs are broken down in the lysosomes of the professional phagocytic cells like macrophages, dendritic cells, NK cells, the plasmid is released, exported to the nucleus and the Spike protein is expressed after the mammalian gene expression promoter expresses the mRNA.

In another aspect, the gene sequences from SARS-CoV-2 and/or mutant/variant SARS-CoV-2 viruses that are cloned in the plasmid can comprise the entire Spike protein encoding genes or just the human ACE2 receptor binding (RBD) gene sequences since the desired antibody response is against the RBD regions of these virus Spike proteins (or other SARS-CoV-2 antigens).

The EDV-COVID-19 vaccines can be administered intramuscularly, intranasaly, or orally. In general, intramuscular administration is preferred. However, the vaccines can be given intranasally or orally to induce a secretory IgA response in the mucosal tract and the lungs. Also, this would elicit an innate and adaptive immune response in the lungs and the oral passages. The vaccines can also be mixed and matched in that the same vaccine can be given intramuscularly and intranasaly to elicit a robust systemic and mucosal immune response.

The EDV-COVID-19 vaccine composition can be readily lyophilized, stored at room temperature, with a shelf life of over 3 years. The EDV-COVID-19 vaccine composition can be courier shipped anywhere in the world and stored at, for example, a hospital pharmacy. Transport and storage can also be done at room temperature. Further, there is a low cost of manufacture, meaning that the EDV-COVID-19 vaccine composition is affordable worldwide.

Figure 23:
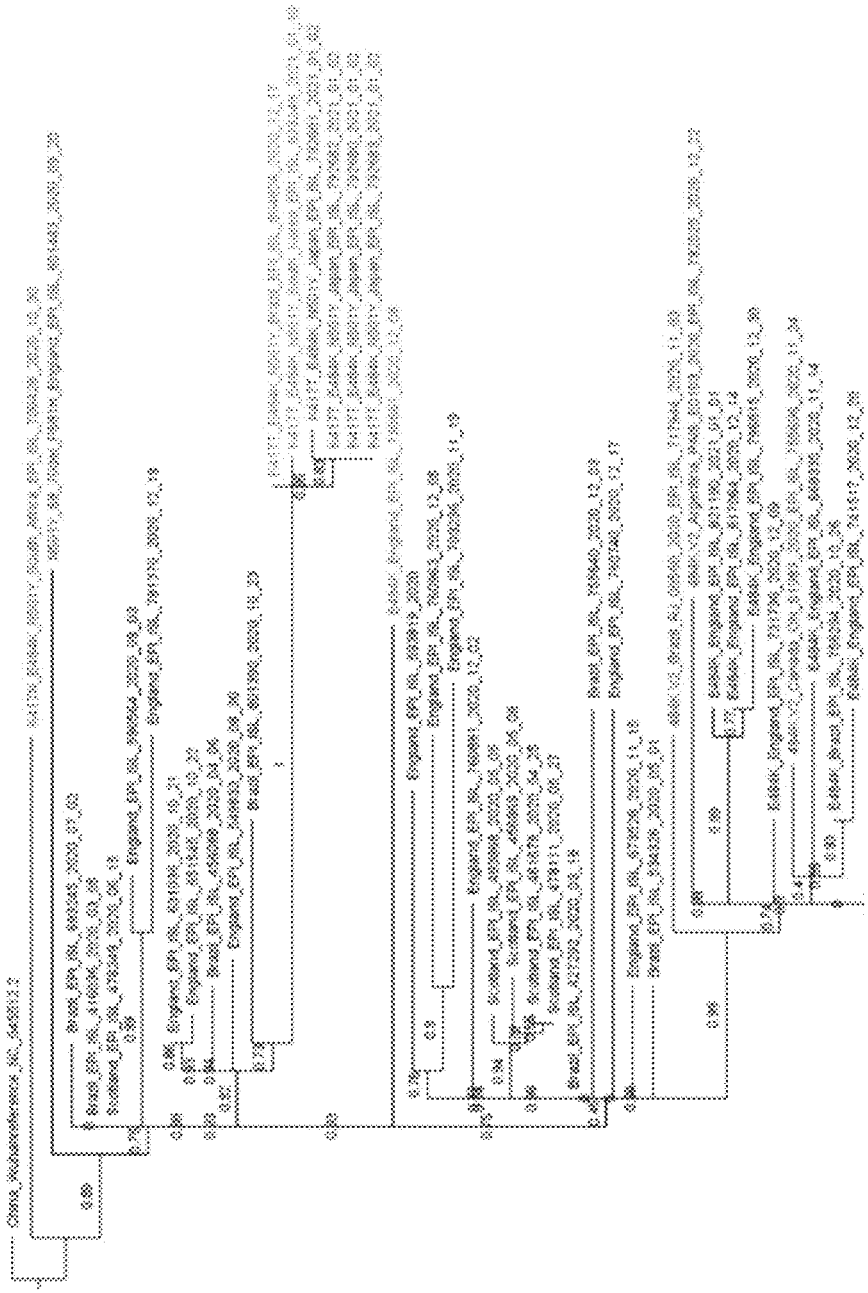

The genomic sequence of a number of different SARS-CoV-2 virus strains and variants, including the Spike proteins of such viruses, is known. See e.g., FIG. 23, which depicts a representative phylogenetic tree of SARS-CoV-2 virus and known variants. Full genome SARS-CoV-2 sequences were downloaded on 19 Jan. 2021 from GISAID (gisaid.org/), aligned using MAFFT: mafft.cbrc.jp/alignment/software/and manually edited using BioEdit v7.2.5. Phylogenetic tree construction was performed using Fast-Tree v2.1.11, with Shimodaira-Hasegawa-like local branch supports, and displayed using FigTree v1.4.4. Excerpted from Toovey et al., *J. Infect.*, 82(5):e23-324 (Feb. 3, 2021).

A new viral strain occurs when a virus goes through one or more mutations that change its behavior in some way, but a variant develops when a virus goes through a mutation of any kind. Examples of SARS-CoV-2 strains include the L strain, the S strain, the V strain, the G strain, the GR strain, and the GH strain. sciencedaily.com/releases/2020/08/200803105246.htm.

Examples of known SARS-CoV-2 variants include, but are not limited to, (1) UK SARS-CoV-2 variant (B.1.1.7/VOC-202012/01), also known as the Alpha variant (B.1.1.7 (Alpha)); (2) B.1.1.7 with E484K variant; (3) B.1.617.2 (Delta) variant; (4) B.1.351 (Beta) variant, also known as the South Africa variant; (5) P.1 (Gamma) variant; (6) B.1.525 (Eta) variant; (7) B.1.526 (Iota) variant; (8) B.1.617 (Kappa, Delta) variants; (9) B.1.617.1 (Kappa) variant; (10) B.1.617.2 variant; (11) B.1.617.3 variant; (12) Lambda (lineage C.37) variant; (13) Epsilon (lineages B.1.429, B.1.427, CAL.20C) variants; (14) Zeta (lineage P.2) variant; (15) Theta (lineage P.3) variant; (16) R.1 variant; (17) Lineage B.1.1.207 variant; and (18) Lineage B.1.620 variant.

Other SARs-CoV-2 variants include SARS-CoV-2 variants having (1) a L452R Spike Protein Substitution, (2) an E484K Spike Protein Substitution, (3) K417N, E484K, N501Y Spike Protein Substitution, (4) K417T, E484K, N501Y Spike Protein Substitution, and (5) SARs-CoV-2 variants having one or more of the following missense mutations: N440, L452R, S477G/N, E484Q, E484K, N501Y, D614G, P681H, P681R, and A701V.

See also (1) Lu et al., "Genomic Characterization and epidemiology of 2019 novel coronavirus: implications for virus origins and receptor binding," *The Lancet,* 395:565-574 (Feb. 22, 2020); (2) Galloway et al., "Emergence of SARS-CoV-2 B.1.1.7 Lineage—United States, Dec. 29, 2020-Jan. 12, 2021," *Centers for Disease Control and Prevention,* 70(3):95-99 (Jan. 22, 2021) (SARS-CoV-2 UK variant sequencing, B.1.1.7 lineage (201/501Y.V1)); (3) Toovey et al., "Introduction of Brazilian SARS-CoV-2 484K.V2 related variants into the UK," J. Infect., 82(5):e23-e24 (Feb. 3, 2021) (describing two Brazilian variants); (4) Sah et al., "Complete Genome Sequence of a 2019 Novel Coronavirus (SARS-CoV-2) Strain Isolated in Nepal," *ASM Journals, Microbiology Resource Announcements,* 9(11) (Mar. 11, 2020); and (5) "Variants of SARS-CoV-2", www.wikipedia.org/wiki/Variants_of_SARS-CoV-2 #Notable_missense_mutations.

Surprisingly, and in contrast to at least some of the COVID-19 vaccines currently being used, the vaccine compositions described herein generate immunity as measured by IgG titers against multiple SARS-CoV-2 variants. In particular, FIGS. 24A-D show the results of IgG titers following administration to five different groups of mice (n=6 per group; ELISA samples run in triplicate): Group 1=saline; Group 2=EDV (bacterial minicell with no payload); Group 3=$EDV_{control}$ (EDVs carrying the plasmid with no insert expressing the Spike protein i.e. plasmid backbone only); Group 4=$EDV_{covid}$ (bacterial minicell comprising the plasmid and the encoded SARS-CoV-2 Spike protein) and Group 5=$EDV_{Covid+\alpha GC}$ (construct shown in FIG. 17). The mice were given $3\times10^9$ EDVs. The results shown in FIGS. 24A-D, detailing S1 subunit-specific IgG titers 3E9 following split dose IM at day 28, demonstrate that serum IgG titers obtained from mice treated with EDV-COVID-GC binds strongly to all four mutant virus Spike proteins: (1) SARS-CoV-2 variant Alpha (B.1.1.7.UK) (FIG. 24A); (2) SARS-CoV-2 variant Beta (B.1.351. SA) (FIG. 24B); (3) SARS-CoV-2 variant Delta (B.1.617.2 India) (FIG. 24C); and (4) SARS-CoV-2 variant Gamma (P.1 Brazil) (FIG. 24D).

IV. Intact Bacterially-Derived Minicells

The term "minicell" is used herein to denote a derivative of a bacterial cell that lacks chromosomes ("chromosome-free") and is engendered by a disturbance in the coordination, during binary fission, of cell division with DNA segregation. Minicells are distinct from other small vesicles, such as so-called "membrane blebs" (about 0.2 μm or less in size), which are generated and released spontaneously in certain situations but which are not due to specific genetic rearrangements or episomal gene expression. Bacterially derived minicells employed in this disclosure are fully intact and are distinguished from other chromosome-free forms of bacterial cellular derivatives characterized by an outer or defining membrane that is disrupted or degraded, even removed. The intact membrane that characterizes the minicells of the present disclosure allows retention of the therapeutic payload within the minicell until the payload is released.

Intact, bacterially-derived minicells or EDVs™ are anucleate, non-living nanoparticles produced as a result of inactivating the genes that control normal bacterial cell division, thereby de-repressing polar sites of cell. Moreover, in contrast to current stealth liposomal drug carriers like DOXIL (liposomal doxorubicin), for example, that can package only ~14,000 molecules per particle, or "armed antibodies," which can carry fewer than 5 drug molecules, bacterial minicells can readily accommodate payloads of up to 1 million drug molecules.

The minicells employed in the present disclosure can be prepared from bacterial cells, such as *E. coli* and *S. typhymurium*. Prokaryotic chromosomal replication is linked to normal binary fission, which involves mid-cell septum formation. In *E. coli*, for example, mutation of min genes, such as minCD, can remove the inhibition of septum formation at the cell poles during cell division, resulting in production of a normal daughter cell and an chromosome-less minicell.

In addition to min operon mutations, chromosome-less minicells also are generated following a range of other genetic rearrangements or mutations that affect septum formation, for example, in the divIVB1 in *B. subtilis*. Minicells also can be formed following a perturbation in the levels of gene expression of proteins involved in cell division/chromosome segregation. For instance, over-expression of minE leads to polar division and production of minicells. Similarly, chromosome-less minicells can result from defects in chromosome segregation, e.g., the smc mutation in *Bacillus subtilis*, the spoOJ deletion in *B. subtilis*, the mukB mutation in *E. coli*, and the parC mutation in *E. coli*. Further, CafA can enhance the rate of cell division and/or inhibit chromosome partitioning after replication, resulting in formation of chained cells and chromosome-less minicells.

Accordingly, minicells can be prepared for the present disclosure from any bacterial cell, be it of Gram-positive or Gram-negative origin due to the conserved nature of bacterial cell division in these bacteria. Furthermore, the minicells used in the disclosure should possess intact cell walls (i.e., are "intact minicells"), as noted above, and should be distinguished over and separated from other small vesicles, such as membrane blebs, which are not attributable to specific genetic rearrangements or episomal gene expression.

In a given embodiment, the parental (source) bacteria for the minicells can be Gram positive, or they can be Gram negative. In one aspect, the parental bacteria are one or more selected from Terra-/Glidobacteria (BV1), Proteobacteria (BV2), BV4 including Spirochaetes, Sphingobacteria, and Planctobacteria. Pursuant to another aspect, the bacteria are one or more selected from Firmicutes (BV3) such as Bacilli, Clostridia or Tenericutes/Mollicutes, or Actinobacteria (BV5) such as Actinomycetales or Bifidobacteriales.

Pursuant to the disclosure, killed bacterial cells are non-living prokaryotic cells of bacteria, cyanobateria, eubacteria and archaebacteria, as defined in the 2nd edition of *Bergey's Manual Of Systematic Biology*. Such cells are deemed to be "intact" if they possess an intact cell wall and/or cell membrane and contain genetic material (nucleic acid) that is endogenous to the bacterial species. Methods of preparing killed bacterial cells are described, for instance, in U.S. 2008/0038296.

In yet a further aspect, the bacteria are one or more selected from Eubacteria (Chloroflexi, Deinococcus-Thermus), Cyanobacteria, Thermodesulfobacteria, thermophiles (Aquificae, Thermotogae), Alpha, Beta, Gamma (Enterobacteriaceae), Delta or Epsilon Proteobacteria, Spirochaetes, Fibrobacteres, Chlorobi/Bacteroidetes, Chlamydiae/Verrucomicrobia, Planctomycetes, Acidobacteria, Chrysiogenetes, Deferribacteres, Fusobacteria, Gemmatimonadetes, Nitrospirae, Synergistetes, Dictyoglomi, Lentisphaerae Bacillales, Bacillaceae, Listeriaceae, Staphylococcaceae, Lactobacillales, Enterococcaceae, Lactobacillaceae, Leuconostocaceae, Streptococcaceae, Clostridiales, Halanaerobiales, Thermoanaerobacterales, Mycoplasmatales, Entomoplasmatales, Anaeroplasmatales, Acholeplasmatales, Haloplasmatales, Actinomycineae, Actinomycetaceae, Corynebacterineae, Nocardiaceae, Corynebacteriaceae, Frankineae, Frankiaceae, Micrococcineae, Brevibacteriaceae, and Bifidobacteriaceae.

For pharmaceutical use, a composition of the disclosure should comprise minicells or killed bacterial cells that are isolated as thoroughly as possible from immunogenic components and other toxic contaminants. Methodology for purifying bacterially derived minicells to remove free endotoxin and parent bacterial cells are described, for example, in WO 2004/113507. Briefly, the purification process achieves removal of (a) smaller vesicles, such as membrane blebs, which are generally smaller than 0.2 µm in size, (b) free endotoxins released from cell membranes, and (c) parental bacteria, whether live or dead, and their debris, which also are sources of free endotoxins. Such removal can be implemented with, inter alia, a 0.2 µm filter to remove smaller vesicles and cell debris, a 0.45 µm filter to remove parental cells following induction of the parental cells to form filaments, antibiotics to kill live bacterial cells, and antibodies against free endotoxins.

Underlying the purification procedure is a discovery that, despite the difference of their bacterial sources, all intact minicells are approximately 400 nm in size, i.e., larger than membrane blebs and other smaller vesicles and yet smaller than parental bacteria. Size determination for minicells can be accomplished by using solid-state, such as electron microscopy, or by liquid-based techniques, e.g., dynamic light scattering. The size value yielded by each such technique can have an error range, and the values can differ somewhat between techniques. Thus, the size of minicells in a dried state can be measured via electron microscopy as approximately 400 nm±50 nm. Dynamic light scattering can measure the same minicells to be approximately 500 nm±50 nm in size. Also, drug-packaged, ligand-targeted minicells can be measured, again using dynamic light scattering, to be approximately 400 nm to 600 nm±50 nm.

Another structural element of a killed bacterial cells or a minicell derived from Gram-negative bacteria is the O-polysaccharide component of lipopolysaccharide (LPS), which is embedded in the outer membrane via the lipid A anchor. The component is a chain of repeat carbohydrate-residue units, with as many as 70 to 100 repeat units of four to five sugars per repeat unit of the chain. Because these chains are not rigid, in a liquid environment, as in vivo, they can adopt a waving, flexible structure that gives the general appearance of seaweed in a coral sea environment; i.e., the chains move with the liquid while remaining anchored to the minicell membrane.

Influenced by the O-polysaccharide component, dynamic light scattering can provide a value for minicell size of about 500 nm to about 600 nm, as noted above. Nevertheless, minicells from Gram-negative and Gram-positive bacteria alike readily pass through a 0.45 µm filter, which substantiates an effective minicell size of 400 nm±50 nm. The above-mentioned scatter in sizes is encompassed by the present invention and, in particular, is denoted by the qualifier "approximately" in the phrase "approximately 400 nm in size" and the like.

In relation to toxic contaminants, a composition of the disclosure preferably comprises less than about 350 EU free endotoxin. Illustrative in this regard are levels of free endotoxin of about 250 EU or less, about 200 EU or less, about 150 EU or less, about 100 EU or less, about 90 EU or less, about 80 EU or less, about 70 EU or less, about 60 EU or less, about 50 EU or less, about 40 EU or less, about 30 EU or less, about 20 EU or less, about 15 EU or less, about 10 EU or less, about 9 EU or less, about 8 EU or less, about 7 EU or less, about 6 EU or less, about 5 EU or less, about 4 EU or less, about 3 EU or less, about 2 EU or less, about 1 EU or less, about 0.9 EU or less, about 0.8 EU or less, about 0.7 EU or less, about 0.6 EU or less, about 0.5 EU or less, about 0.4 EU or less, about 0.3 EU or less, about 0.2 EU or less, about 0.1 EU or less, about 0.05 EU or less, or about 0.01 EU or less.

A composition of the disclosure also can comprise at least-about $10^9$ minicells or killed bacterial cells, e.g., at least about $1 \times 10^9$, at least about $2 \times 10^9$, at least about $5 \times 10^9$, or at least $8 \times 10^9$ In some embodiments, the composition comprises no more than about $10^{11}$ minicells or killed bacterial cells, e.g., no more than about $1 \times 10^{11}$ or no more than about $9 \times 10^{10}$, or no more than about $8 \times 10^{10}$.

V. CD1d-Recognized Antigens

In one embodiment, the adjuvant composition comprises (a) an immunogenically effective amount of an encapsulated CD1d-recognized antigen and (b) a minicell carrying a recombinant plasmid encoding one or more viral antigens.

In one embodiment, the CD1d-recognized antigen and the recombinant plasmid are packaged within two intact bacterially derived minicells or killed bacterial cells. The CD1d-recognized antigen can be comprised within a first intact bacterially-derived minicell or killed bacterial cell, and the recombinant plasmid encoding viral antigens is comprised within a second intact bacterially-derived minicell or killed bacterial cell.

It is well recognized that early in infection, IFN stimulation results in altered cellular transcriptional programs, leading to an antiviral state characterized by the activation of a large set of host genes with partially defined antiviral functions [Schoggins et al., 2011].

In some embodiments, the immune response produced in the target cells comprises the production of Type I interferon, including interferon-α and/or interferon-β.

This bacterial minicell treatment should reduce the severity of the disease in almost all patients and reduce the duration of the disease making it more like just a common cold. Alternatively, the treatment may be administered in a healthy person as a vaccine to protect against the viral infection where the virus carries the proteins encoded by the recombinant plasmid carried in the minicell.

The present compositions and methods comprise a vector, which can be an intact bacterially derived minicell, that comprises a CD1d-recognized antigen. Such antigens result in an increases the level (e.g., the activity or expression level) of type II interferons, e.g., IFN-γ (gamma). IFN-γ is involved in the regulation of the immune and inflammatory responses; in humans, there is only one type of interferon-gamma. It is produced in activated T cells and natural killer cells. IFN-γ potentiates the effects of type I IFNs. IFN-γ released by Th1 cells recruits leukocytes to a site of infection, resulting in increased inflammation. It also stimulates macrophages to kill bacteria that have been engulfed. IFN-γ released by Th1 cells also is important in regulating the Th2 response.

IFNγ cytokines are released by innate Natural Killer (NK) cells upon binding of natural antigen, but glycosphingolipid compounds can function as potent activators of both innate and acquired immune responses. Exposure to a glycosphingolipid induces a potent cytokine response by innate natural killer T (iNKT) cells, including the type II interferon, IFN-γ, and a number of Interleukins (Th1-, Th2-, and/or Th17-type cytokines). iNKT cells then induce DC maturation and display T cell helper-like functions that result in the development of cytotoxic T cell responses.

Examples of glycosphingolips useful to induce a IFN type II response are described herein and include C-glycosidific form of α-galactosylceramide (α-C-GalCer), α-galactosylceramide (α-GalCer), 12 carbon acyl form of galactosylceramide (β-GalCer), β-D-glucopyranosylceramide (p-GlcCer), 1,2-Diacyl-3-0-galactosyl-sn-glycerol (BbGL-II), diacylglycerol containing glycolipids (Glc-DAG-s2), ganglioside (GD3), gangliotriaosylceramide (Gg3Cer), glycosylphosphatidylinositol (GPI), α-glucuronosylceramide (GSL-1 or GSL-4), isoglobotrihexosylceramide (iGb3), lipophosphoglycan(LPG), lyosphosphatidylcholine (LPC), α-galactosylceramide analog (OCH), and threitolceramide. In a particular embodiment the minicell disclosed herein comprises α-galactosylceramide (α-GalCer) as a type II IFN agonist.

In some embodiments, the CD1d-recognized antigen is a glycosphingolipid. In some embodiments, the glycosphingolipid is selected from among α-galactosylceramide (α-GalCer), C-glycosidific form of α-galactosylceramide (α-C-GalCer), 12 carbon acyl form of galactosylceramide (β-GalCer), β-D-glucopyranosylceramide (β-GlcCer), 1,2-Diacyl-3-O-galactosyl-sn-glycerol (BbGL-II), diacylglycerol containing glycolipids (Glc-DAG-s2), ganglioside (GD3), gangliotriaosylceramide (Gg3Cer), glycosylphosphatidylinositol (GPI), α-glucuronosylceramide (GSL-1 or GSL-4), isoglobotrihexosylceramide (iGb3), lipophosphoglycan(LPG), lyosphosphatidylcholine (LPC), α-galactosylceramide analog (OCH), threitolceramide, and a derivative of any thereof. In some embodiments, the glycosphingolipid is α-GalCer. In some embodiments, the glycosphingolipid is a synthetic α-GalCer analog. In some embodiments, the synthetic α-GalCer analog is selected from among 6'-deoxy-6'-acetamide α-GalCer (PBS57), napthylurea α-GalCer (NU-α-GC), NC-α-GalCer, 4ClPhC-α-GalCer, PyrC-α-GalCer, α-carba-GalCer, carba-α-D-galactose α-GalCer analog (RCAI-56), 1-deoxy-neo-inositol α-GalCer analog (RCAI-59), 1-O-methylated α-GalCer analog (RCAI-92), and HS44 aminocyclitol ceramide. In some embodiments, the CD1d-recognized antigen is derived from a bacterial antigen, a fungal antigen, or a protozoan antigen.

α-GC, an IFN type II agonist is known to stimulate the immune system through activation of a type of white blood cell known as natural killer T cell (NKT cell).

The minicell can deliver type II IFN agonists directly to cells of the immune system, with a view to enhancing iNKT cell activation and type II interferon IFN-γ production in vivo. Non-targeted intact, bacterially derived minicells are taken up by phagocytic cells of the immune system, where they are broken down in endosomes, and αGC is presented to iNKT cells for immune activation. Accordingly, in some embodiments the minicell provides targeted delivery of type II interferon agonists. In other embodiments, the composition disclosed herein comprises a non-targeted minicell comprising a type II interferon agonist.

IFN-γ production is controlled by cytokines secreted by antigen presenting cells (APCs), most notably interleukin (IL)-12-and IL-18. These cytokines serve as a bridge to link infection with IFN-γ production in the innate immune response. Macrophage recognition of many pathogens induces secretion of IL-12 and chemokines. These chemokines attract NK cells to the site of inflammation, and IL-12 promotes IFN-γ synthesis in these cells. In macrophages, natural killer cells and T cells, the combination of IL-12 and IL-18 stimulation further increases IFN-γ production. Accordingly, any of these proteins or their combinations are suitable agents for the purpose of this disclosure.

Negative regulators of IFN-gamma production include IL-4, IL-10, transforming growth factor β and glucocorticoids. Proteins or nucleic acids that inhibit these factors will be able to stimulate the production of IFN-7.

Also suitable for use in this context are polynucleotides that encode IFN-γ or genes that activate the production and/or the secretion of IFN-γ.

The agent that increases the level of IFN-γ may also be a viral vaccine. A number of viral vaccines are available that can induce IFN-γ production without causing infection or other types of adverse effects. Illustrative of this class of viral-vaccine agent is a flu (influenza) vaccine.

Serum concentration of IFN-γ required for effectively activating host immune response to is low when the patient also receives administration of drug-loaded, bispecific antibody-targeted minicells or killed bacterial cells. Thus, in one aspect the inventive methodology results in increase of serum IFN-γ concentration that is not higher than about 30,000 μg/mL. In another aspect, the serum IFN-γ concentration is increased to not higher than about 5000 μg/mL, 1000 μg/mL, 900 μg/mL, 800 μg/mL, 700 μg/mL, 600 μg/mL, 500 μg/mL, 400 μg/mL, 300 μg/mL, 200 μg/mL, or 100 μg/mL. In a further aspect, the resulting serum IFN-gamma concentration is at least about 10 μg/mL, or at least about 20 μg/mL, 30 μg/mL, 40 μg/mL, 50 μg/mL, 60 μg/mL, 70 μg/mL, 80 μg/mL, 90 μg/mL, 100 μg/mL, 150 μg/mL, 200 μg/mL, 300 μg/mL, 400 μg/mL or 500 μg/mL.

Pursuant to some aspects, the agent is an IFN-γ protein or an engineered protein or analog. In some aspects, the administration achieves from about 0.02 ng to 1 microgram of IFN-γ per ml of host blood. In one aspect, the achieved IFN-gamma concentration in the host blood is from about 0.1 ng to about 500 ng per ml, from about 0.2 ng to about 200 ng per ml, from about 0.5 ng to about 100 ng per ml, from about 1 ng to about 50 ng per ml, or from about 2 ng to about 20 ng per ml.

In some embodiments, the encapsulated CD1d-recognized antigen (e.g., α-GalCer) and the minicell carrying the recombinant plasmid encoding at least one viral antigen are administered simultaneously. In some embodiments, the encapsulated CD1d-recognized antigen (e.g., α-GalCer) and the minicell carrying the recombinant plasmid encoding viral antigens are administered sequentially. In some embodiments, the encapsulated CD1d-recognized antigen (e.g., α-GalCer) and the minicell carrying the recombinant plasmid encoding viral antigens are administered multiple times. In some embodiments, the encapsulated CD1d-recognized antigen (e.g., α-GalCer) and the minicell carrying the recombinant plasmid encoding viral antigens are administered at least once a week or twice a week or three times per week or four times per week until the disease is resolved.

Following infection with SARS-CoV-2, the aim of this therapy would be to achieve the following: (1) stimulate innate and adaptive immunity via recruitment of fresh monocytes and dendritic cells from the bone marrow and activation of NK cells. This would keep the immune status high in the patients as the disease progresses and prevent the development of lymphopenia. (2) Physiologically well tolerated secretion of Type I (IFNα and IFNβ) and Type II (IFNγ) interferons. It is well recognized that early in viral infection, IFN stimulation results in altered cellular transcriptional programs, leading to an antiviral state characterized by the activation of a large set of host genes with partially defined antiviral functions. This activation would enable rapid elimination of virally infected cells along with a reduction in viral replication. (3) Secrete antibodies to the four structural proteins of the virus (Envelope, Membrane, Spike and Nucleocapsid) and this would aim to mop up a significant number of viral particles that are released from infected cells. All of the above would be expected with minimal to no toxicity.

The compositions can be administered to subjects at risk of a SARS-CoV-2 variant infection as a vaccine, or the compositions can be administered as a therapeutic to a subject who is suffering from a SARS-CoV-2 variant infection viral infection.

Additionally, it has never been reported that IFNγ augments serum IgG antibody response to any antigen. The present disclosure is the first to demonstrate this phenomenon. This discovery is clearly seen in FIGS. 6A-6B, where the EDV composition carrying the plasmid and Spike protein did not elicit high levels of IgG antibodies to the Spike protein. In contrast, the EDV composition carrying the same COVID plasmid and Spike protein, and additionally also carrying αGC, provided a highly significant rise in IgG antibody titers to the Spike protein (FIGS. 6A, 6B). Similarly, only the composition carrying the combination of a SAR-CoV-2 antigen and αGC triggered a robust IFNα (FIG. 7A), IFNγ (FIG. 7B), IL12 (FIG. 7C), IL6 (FIG. 7D), and TNFα (FIG. 7F) response. The only function of αGC is to rapidly trigger the secretion of IFNγ which then stimulates a plethora of anti-viral immune responses. This is the first discovery showing that one or more of the effects of IFNγ is to augment anti-viral serum IgG antibody titers.

VI. Loading Viral Antigens and CD1d-Recognized Antigens into Minicells or Killed Bacterial Cells Viral antigens as well as CD1d-recognized antigens can be packaged into minicells or killed bacterial cells directly, by co-incubating a plurality of intact minicells or killed bacterial cells with the antigens in a buffer. The buffer composition can be varied, as a function of conditions well known in this field, to optimize the loading of the antigens in the intact minicells. The buffer also may be varied in dependence on the antigen (e.g., dependent upon the nucleotide sequence or the length of the nucleic acid to be loaded in the minicells in the case of a nucleic acid payload). An exemplary buffer suitable for loading includes, but is not limited to, phosphate buffered saline (PBS). Once packaged, the antigen remains inside the minicell and is protected from degradation. Prolonged incubation studies with siRNA-packaged minicells incubated in sterile saline have shown, for example, no leakage of siRNAs.

Antigens such as proteins that can be encoded for by a nucleic acid, can be introduced into minicells by transforming into the parental bacterial cell a vector, such as a plasmid, that encodes the antigen. When a minicell is formed from the parental bacterial cell, the minicell retains certain copies of the plasmid and/or the expression product, e.g., the antigen. More details of packaging and expression product into a minicell is provided in WO 03/033519.

Data presented in WO 03/033519 demonstrated, for example, that recombinant minicells carrying mammalian gene expression plasmids can be delivered to phagocytic cells and to non-phagocytic cells. WO 03/033519 also described the genetic transformation of minicell-producing parent bacterial strains with heterologous nucleic acids carried on episomally-replicating plasmid DNAs. Upon separation of parent bacteria and minicells, some of the episomal DNA segregated into the minicells. The resulting recombinant minicells were readily engulfed by mammalian phagocytic cells and became degraded within intracellular phagolysosomes. Moreover, some of the recombinant DNA escaped the phagolysosomal membrane and was transported to the mammalian cell nucleus, where the recombinant genes were expressed. In other embodiments, multiple antigens can be packaged in the same minicell.

Antigens can be packaged in minicells by creating a concentration gradient of the antigen between an extracellular medium comprising minicells and the minicell cytoplasm. When the extracellular medium comprises a higher antigen concentration than the minicell cytoplasm, the antigen naturally moves down this concentration gradient, into the minicell cytoplasm. When the concentration gradient is reversed, however, the antigen does not move out of the minicells. More details of the active agent loading process and its surprising nature are found, for instance, in U.S. Patent Application Publication No. 2008/0051469.

VII. Formulations

The disclosure includes within its scope compositions comprising a combination of (a) a vector, intact bacterial minicell, or killed bacterial cell comprising as a payload at least one viral antigen; and (b) a vector, intact bacterial minicell, or killed bacterial cell comprising as a payload at least one CD1d-recognized antigen, both of which are present in at least one pharmaceutically acceptable carrier. The at least one viral antigen and at least one CD1d-recognized antigen can be in the same or different vector, intact bacterial minicell, or killed bacterial cell. At least one of the viral antigen and CD1 d-recognized antigen is present in an intact bacterial minicell.

In another aspect, one of the viral antigen and at least one CD1d-recognized antigen are present in a non-bacterial cell carrier, such as a liposomal carrier. In some aspects, the CD1 d-recognized antigen is the interferon type II agonist α-galactosyl ceramide.

Compositions of the disclosure can be presented in unit dosage form, e.g., in ampules or vials, or in multi-dose containers, with or without an added preservative. The composition can be a solution, a suspension, or an emulsion in oily or aqueous vehicles, and can comprise formulatory agents, such as suspending, stabilizing and/or dispersing agents. A suitable solution is isotonic with the blood of the recipient and is illustrated by saline, Ringer's solution, and dextrose solution. Alternatively, formulations can be in lyophilized powder form, for reconstitution with a suitable vehicle, e.g., sterile, pyrogen-free water or physiological saline. The formulations also can be in the form of a depot preparation. Such long-acting formulations can be administered by implantation (for instance, subcutaneously or intramuscularly) or by intramuscular injection. In some embodiments, administering comprises enteral or parenteral administration. In some embodiments administering comprises administration selected from oral, buccal, sublingual, intranasal, rectal, vaginal, intravenous, intramuscular, and subcutaneous injection.

In some aspects, a minicell-comprising composition that includes a therapeutically effective amount of a viral antigen, as well as a therapeutically effective amount of a CD1d-recognized antigen, is provided. A "therapeutically effective" amount of an antigen is an amount that invokes a pharmacological response when administered to a subject, in accordance with the present disclosure.

In the context of the present disclosure, therefore, a therapeutically effective amount can be gauged by reference to the prevention or amelioration of the viral infection, either in an animal model or in a human subject, when minicells carrying a therapeutic payload are administered, as further described below. An amount that proves "therapeutically effective amount" in a given instance, for a particular subject, may not be effective for 100% of subjects similarly treated for the viral infection, even though such dosage is deemed a "therapeutically effective amount" by skilled practitioners. The appropriate dosage in this regard also will vary as a function, for example, of the stage and severity of the viral infection, as well as whether the subject has any underlying adverse medical conditions, is aged 60+, or is immunocompromised.

A. Administration Routes

Formulations of the disclosure can be administered via various routes and to various sites in a mammalian body, to achieve the therapeutic effect(s) desired, either locally or systemically. Delivery may be accomplished via any pharmaceutically acceptable route, for example, oral administration, application of the formulation to a body cavity, inhalation, nasal administration, pulmonary administration, insufflation, or by injection (e.g., parenteral, intramuscular, intravenous, intraportal, intrahepatic, peritoneal, subcutaneous, intratumoral, or intradermal administration). A combination of routes also may be employed.

B. Purity

Bacterial minicells are substantially free from contaminating parent bacterial cells. Thus, minicell-comprising formulations preferably comprise fewer than about 1 contaminating parent bacterial cell per $10^7$ minicells, fewer than about 1 contaminating parent bacterial cell per $10^8$ minicells, fewer than about 1 contaminating parent bacterial cell per $10^9$ minicells, fewer than about 1 contaminating parent bacterial cell per $10^{10}$ minicells, or fewer than about 1 contaminating parent bacterial cell per $10^{11}$ minicells.

Methods of purifying minicells are known in the art and described in PCT/IB02/04632. One such method combines cross-flow filtration (feed flow is parallel to a membrane surface; Forbes, 1987) and dead-end filtration (feed flow is perpendicular to the membrane surface). Optionally, the filtration combination can be preceded by a differential centrifugation, at low centrifugal force, to remove some portion of the bacterial cells and thereby enrich the supernatant for minicells.

Particularly effective purification methods exploit bacterial filamentation to increase minicell purity. Thus, a minicell purification method can include the steps of (a) subjecting a sample containing minicells to a condition that induces parent bacterial cells to adopt a filamentous form, followed by (b) filtering the sample to obtain a purified minicell preparation.

Known minicell purification methods also can be combined. One highly effective combination of methods is as follows:

Step A: Differential centrifugation of a minicell producing bacterial cell culture. This step, which may be performed at 2,000 g for about 20 minutes, removes most parent bacterial cells, while leaving minicells in the supernatant;

Step B: Density gradient centrifugation using an isotonic and non-toxic density gradient medium. This step separates minicells from many contaminants, including parent bacterial cells, with minimal loss of minicells. Preferably, this step is repeated within a purification method;

Step C: Cross-flow filtration through a 0.45 μm filter to further reduce parent bacterial cell contamination.

Step D: Stress-induced filamentation of residual parent bacterial cells. This may be accomplished by subjecting the minicell suspension to any of several stress-inducing environmental conditions;

Step E: Antibiotic treatment to kill parent bacterial cells;

Step F: Cross-flow filtration to remove small contaminants, such as membrane blebs, membrane fragments, bacterial debris, nucleic acids, media components and so forth, and to concentrate the minicells. A 0.2 μm filter may be employed to separate minicells from small contaminants, and a 0.1 m filter may be employed to concentrate minicells;

Step G: Dead-end filtration to eliminate filamentous dead bacterial cells. A 0.45 um filter may be employed for this step; and Step H: Removal of endotoxin from the minicell preparation. Anti-Lipid A coated magnetic beads may be employed for this step.

C. Administration Schedules

In general, the formulations disclosed herein may be used at appropriate dosages defined by routine testing, to obtain optimal physiological effect, while minimizing any potential toxicity. The dosage regimen may be selected in accordance with a variety of factors including age, weight, sex, medical condition of the patient; the severity of the condition to be treated, the route of administration, and the renal and hepatic function of the patient.

Optimal precision in achieving concentrations of minicell and drug within the range that yields maximum efficacy with minimal side effects may require a regimen based on the kinetics of the minicell and antigen availability to target sites and target cells. Distribution, equilibrium, and elimination of a minicell or antigen may be considered when determining the optimal concentration for a treatment regimen. The dosages of the minicells and antigens may be adjusted when used in combination, to achieve desired effects.

Moreover, the dosage administration of the formulations may be optimized using a pharmacokinetic/pharmacodynamic modeling system. For example, one or more dosage regimens may be chosen and a pharmacokinetic/pharmacodynamic model may be used to determine the pharmacokinetic/pharmacodynamic profile of one or more dosage regimens. Next, one of the dosage regimens for administration may be selected which achieves the desired phanmacokinetic/pharmacodynamic response based on the particular pharmacokinetic/pharmacodynamic profile. See, e.g., WO 00/67776.

Specifically, the formulations may be administered at least once every day for a few days (three to four) or until the symptoms of viral infection subside. In one embodiment, the formulations are administered at least once a day until viral disease subsides.

More specifically, the formulations may be administered at least once a day for about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, or about 31 days. Alternatively, the formulations may be administered about once every day, about once every about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30 or about 31 days or more.

The compositions may be administered in a single daily dose, or the total daily dosage may be administered in divided doses of two, three, or four times daily.

VIII. Definitions

Unless defined otherwise, all technical and scientific terms used in this description have the same meaning as commonly understood by those skilled in the relevant art.

For convenience, the meaning of certain terms and phrases employed in the specification, examples, and appended claims are provided below. Other terms and phrases are defined throughout the specification.

The singular forms "a," "an," and "the" include plural reference unless the context clearly dictates otherwise.

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

As used herein, except where the context requires otherwise, the term "comprise" and variations of the term, such as "comprising," "comprises" and "comprised" are not intended to exclude other additives, components, integers or steps.

The phrases "biologically active" and "biological activity" are used to qualify or to denote, as the case may be, the effect(s) of a compound or composition on living matter. Thus, a material is biologically active or has biological activity if it has interaction with or effect on any cell tissue in a human or animal body, e.g., by reacting with protein, nucleic acid, or other molecules in a cell.

"Individual," "subject," "host," and "patient," terms used interchangeably in this description, refer to any mammalian subject for whom diagnosis, treatment, or therapy is desired. The individual, subject, host, or patient can be a human or a non-human animal. Thus, suitable subjects can include but are not limited to non-human primates, cattle, horses, dogs, cats, guinea pigs, rabbits, rats, and mice.

The terms "treatment," "treating," "treat," and the like refer to obtaining a desired pharmacological and/or physiologic effect in a patient. The effect can be prophylactic in terms of completely or partially preventing viral infection or a symptom thereof and/or the effect can be therapeutic in terms the viral infection. Alternatively or additionally, a desired treatment effect can be an increase of overall patient survival, progress-free survival, or a reduction of adverse effect.

The phrase "pharmaceutical grade" denotes a lacking of parental cell contamination, cell debris, free endotoxin and other pyrogens that is sufficient to meet regulatory requirements for human intravenous administration. See, e.g., "Guidance for Industry—Pyrogen and Endotoxins Testing," U.S. Food and Drug Administration (June 2012).

"Payload" in this description identifies or qualifies biologically active material that is to be loaded or that has been loaded into a minicell for delivery to a targeted host cell.

The term "substantially" generally refers to at least 90% similarity. In some embodiments, in the context of a first X-ray powder diffraction pattern being substantially as shown in a second X-ray powder diffraction pattern, "substantially" refers to ±0.2°. In some embodiments, in the context of a first differential scanning calorimetry thermogram being substantially as shown in a second differential scanning calorimetry thermogram, "substantially" refers to +0.4° C. In some embodiments, in the context of a first thermogravimetric analysis being substantially as shown in a second thermogravimetric analysis, "substantially" refers to ±0.4% weight. In some embodiments, "substantially purified" refers to at least 95% purity. This includes at least 96, 97, 98, or 99% purity. In further embodiments, "substantially purified" refers to about 95, 96, 97, 98, 99, 99.5, or 99.9% purity, including increments therein.

As used herein, "therapeutic activity" or "activity" may refer to an activity whose effect is consistent with a desirable therapeutic outcome in humans, or to desired effects in non-human mammals or in other species or organisms. Therapeutic activity may be measured in vivo or in vitro. For example, a desirable effect may be assayed in cell culture.

As used herein, the phrase "therapeutically effective amount" shall mean the drug dosage that provides the specific pharmacological response for which the drug is administered in a significant number of subjects in need of such treatment. It is emphasized that a therapeutically effective amount of an antigen that is administered to a particular subject in a particular instance will not always be effective in treating the viral infection described herein, even though such dosage is deemed to be a therapeutically effective amount by those of skill in the art.

The present technology, thus generally described, will be understood more readily by reference to the following examples, which are provided by way of illustration and are not intended to be limiting of the present technology.

EXAMPLES

Example 1

FIG. 1 depicts an exemplary composition, comprising a first intact, bacterial minicell comprising a plasmid encoding viral protein, which function to stimulate antibody responses to the viral proteins. Plasmid double-stranded DNA is recognized by intracellular nucleic acid sensors and triggers IFNα and IFNβ response. Also shown is a second intact, bacterially-derived minicell comprising an IFNγ stimulating compound, α-galactosyl ceramide.

Since the genomic sequence of the SARS-CoV-2 virus is known, a plasmid expressing all four of the SARS-CoV2 proteins expressed from a single bacterial expression promoter can be made. The plasmic then can be encapsulated in an intact bacterially-derived minicell (i.e., an EnGeneIC Nanocell Dream Vector (EDV™)). A second component would be an intact bacterially-derived minicell packaged with a glycolipid (α-galactosyl ceramide; EDVα-GC).

The product can be lyophilized. The intact bacterially-derived minicell based products are very stable and lyophilized vials with anti-cancer compounds and intact bacterially-derived minicell loaded with α-GC have already shown stability for more than 3 years when the vials are simply stored at 4° C. in a normal fridge at the hospital pharmacy. They can be shipped anywhere in the world via a courier, which has previously been demonstrated for US cancer trials using EDVs.

Patient dosing: When a patient is to be dosed, the vial can be reconstituted in 1 ml of sterile physiological saline and injected i.v. as a bolus injection.

The plasmid can be transformed into the intact bacterially-derived minicell producing strain and it would express the viral proteins in the bacterial cytoplasm. When the intact bacterially-derived minicell is produced during asymmetric bacterial division a lot of the protein is segregated into the intact bacterially-derived minicell cytoplasm. This has been demonstrated in in several studies where heterologous foreign proteins have been expressed in intact bacterially-derived minicell producing bacterial cells and the proteins segregate into the intact bacterially-derived minicell cytoplasm.

The expected results from plasmid-packaged intact bacterially-derived minicells is an antibody response to all 4 virus proteins, plus a Type I interferon response.

The injected intact bacterially-derived minicells would be rapidly engulfed by the cells of the immune system (macrophages, NK cells and dendritic cells) in the lymph nodes, liver and spleen. The intact bacterially-derived minicells normally enter the endosomes and are broken down in the lysosomes and the plasmid is released which escapes into the cytoplasm.

Cytosolic DNA sensors, which would recognize the plasmid DNA, are a class of pattern recognition receptors (PRRs), which induce the production of type I interferons (IFNα and IFNβ) and trigger the induction of a rapid and efficient innate immune response. It is well known that Type I interferons have a potent antiviral effect.

The viral proteins are released from the broken down intact bacterially-derived minicells in the lysosomes and undergo antigen processing and presentation via MHC Class II on to the cell surface. This triggers a potent antibody response to the viral antigenic epitopes. This further provokes a CD4+/CD8+ T cell response against virally infected cells and this should augment the anti-viral response.

The activation maturation and proliferation of fresh bone marrow derived monocytes along with the activation and proliferation of macrophages, dendritic cells, NK cells, B cells and T cells would be expected to overcome the observed lymphopenia in the elderly and immune-compromised SARS-CoV2 patients.

Expected results from α-galactosyl ceramide packaged intact bacterially-derived minicells —induction of IFN-γ response: EDV™$_{α-GC}$ are also engulfed by cells of the immune system (macrophages, NK cells and dendritic cells) in the lymph nodes, liver and spleen. The intact bacterially-derived minicells are broken down in the intracellular lysosomes and the α-GC is released which is picked up by lysosomally associated CD1d (MHC Class I like molecule which is involved in the presentation of foreign glycolipids) and transported to the cell surface. This α-GC/CD1d complex is recognized by the invariant T cell receptor on invariant NKT cells and this results in the rapid release of IFN-γ. IFN-γ is known to be a potent stimulator of a specific anti-viral immune response which would then be expected to augment the rejection of the viral infection.

The intact bacterially-derived minicell therapeutics have already been shown to be safe in human cancer patients where over 1,500 doses have been administered in over 140 patients with minimal to no side effects despite repeat dosing.

Example 2

The purpose of this example was to evaluate the impact on a human immune response of a cancer patient with a therapeutic composition comprising a bacterially-derived minicell-packaged+CD1d-recognized antigen (α-galactosyl ceramide).

Preparation of epidermal growth factor receptor (EGFR)-antibody targeted, PNU-packaged intact bacterially-derived minicells is described, for example, in WO 2020/021437. The intact bacterially-derived minicells administered to the subject included a combination bacterial minicell composition comprising an intact bacterially-derived minicell-packaged anticancer compound (PNU-159682) combined with an intact bacterially-derived minicell-packaged+CD1d-recognized antigen (α-galactosyl ceramide).

FIG. 2 shows peripheral blood mononuclear cells (PBMCs) from patient 1-CB04-1 (72 year old male) with end-stage hepatocellular carcinoma, showing an elevation in CD8+ cytotoxic T cells (FIG. 2A), NK cells (FIG. 2B), NKT cells (FIG. 2C) and iNKT cells (FIG. 2D) by cycle 2 and 3 following treatment with epidermal growth factor receptor (EGFR)-antibody targeted, PNU-packaged intact bacterially-derived minicells (i.e., EDV™)+α-galactosyl ceramide packaged intact bacterially-derived minicells (i.e., EDV™). "PNU" is PNU-159682, which is a morpholinyl anthracycline derivative. FIG. 2B shows the percent of leukocytes vs subsets of NK cells (C1D1, C1D9, C2D7, and C3D7). FIG. 2C shows the percent of T-cells vs subsets of NKT cells (C1D1, C1D9, C2D7, and C3D7). Finally, FIG. 2D shows the percent NKT cells vs subsets of iNKT cells (ClD1, C1D9, C2D7, and C3D7).

It is to be noted that the patient was elderly and severely immune-compromised.

TABLE 3

| Patient # | Age | Gender | Stage IV cancer |
|---|---|---|---|
| 1-CB04-1 | 72 | M | Hepatocellular Ca. |

X-axis = Cycle and dose number e.g. C2D7 = Cycle 2, dose 7

Groups of specific, differentiated T cells have an important role in controlling and shaping the immune response by providing a variety of immune-related functions. One of these functions is immune-mediated cell death, and it is carried out by T cells in several ways: CD8+ T cells, also known as "killer cells", are cytotoxic; this means that they are able to directly kill virus-infected cells as well as cancer cells. CD8+ T cells are also able to utilize small signalling proteins, known as cytokines, to recruit other cells when mounting an immune response.

The results detailed in FIGS. 2A-D demonstrate the positive effects on the immune system following administration of a combination bacterial minicell composition comprising an intact bacterially-derived minicells-packaged anticancer compound (e.g., PNU-159682) combined with an intact bacterially-derived minicell-packaged+CD1d-recognized antigen (α-galactosyl ceramide). In particular, FIG. 2A shows a graph of percent CD8+ T cells (y axis) vs T cell subsets for naïve (first 4 columns) and effector (last four columns). T cell subsets shown are C1D1, C1D9, C2D7, and C3D7.

Example 3

The purpose of this example was to evaluate the impact on a human immune response of a cancer patient with a therapeutic composition comprising a bacterially-derived minicell-packaged+CD1d-recognized antigen (α-galactosyl ceramide).

Similar to Example 2, the intact bacterially-derived minicells administered to the subject included a combination bacterial minicell composition comprising an intact bacterially-derived minicell-packaged anticancer compound (PNU-159682) combined with an intact bacterially-derived minicell-package+CD1d-recognized antigen (α-galactosyl ceramide).

TABLE 4

| Patient # | Age | Gender | Stage IV cancer |
|---|---|---|---|
| 1-CB10-1 | 45 | F | Colorectal ca + renal failure/on dialysis |

X-axis = Cycle and dose number e.g. C2D7 = Cycle 2, dose 7

FIG. 3 shows PBMCs from a 45 year-old female with end-stage colorectal cancer, demonstrating activation of key immune cells. The patient's CD8+ effector cytotoxic T cells (CD45RA+CCR7−) increased significantly by cycles 2 and 3. In particular, FIG. 3A shows a graph of the percent CD8+ T cells vs CD8+ memory T cell subsets, with the first 4 columns corresponding to the naive test results, followed by the second four columns corresponding to the effector test results. The patient's CD8+ effector cytotoxic T cells (CD45RA+CCR7−) increased significantly by cycles 2 and 3.

Similarly, FIG. 3B shows a graph of the percent leukocytes vs NK cell subsets (C1D1, C1D9, C2D7, and C3D7). The result show that the subject's PBMCs showed an increase in NK cells (FIG. 3B) by cycles 2 and 3. Finally, FIG. 3C shows IFNγ (pg/mL) vs IFNγ measured per dose. Interestingly, ELISA analysis of the patient's serum, 3 hrs post each intact bacterially-derived minicell dose, showed a spike in IFNγ (FIG. 3C), which would occur if the α-galactosyl ceramide were effectively presented by antigen presenting cells (APCs) to the iNKT cells, which would then trigger off the release of IFNγ, a critical mediator in fighting viral infections.

Example 4

The purpose of this example was to evaluate the impact on a human immune response of a cancer patient with a therapeutic composition comprising a bacterially-derived minicell-packaged+CD1d-recognized antigen (α-galactosyl ceramide).

Similar to Example 2, the intact bacterially-derived minicells administered to the subject included a combination bacterial minicell composition comprising an intact bacterially-derived minicell-packaged anticancer compound (PNU-159682) combined with an intact bacterially-derived minicell-packaged+CD1d-recognized antigen (α-galactosyl ceramide).

FIG. 4 shows the white blood cell counts (average of 9 patients) at pre-dose and 3 hrs post dose. 8 of the 9 patients were elderly and all were severely immune-compromised with Stage IV pancreatic cancer and all having failed all lines of conventional therapy. Yet, interestingly, 3 hrs post dose there was a significant increase in white blood cells (WBC) and this occurred at every dose after dose 2, suggesting that the early doses of intact bacterially-derived minicells recruit fresh monocytes from the bone marrow following activation signals from the macrophages, dendritic cells and NK cells and by dose 3 they are sufficiently activated and matured to result in proliferation.

TABLE 5

| Patient # | Age | Gender | Stage IV cancer |
|---|---|---|---|
| CB01 | 67 | M | Pancreatic Ca. |
| CB05 | 62 | M | Pancreatic Ca. |
| CB06 | 71 | M | Pancreatic Ca. |
| CB07 | 68 | M | Pancreatic Ca. |
| CB12 | 47 | M | Pancreatobiliary Ca. |
| CB14 | 65 | F | Pancreatic Ca. |
| CB15 | 70 | M | Pancreatic Ca. |
| CB16 | 70 | F | Pancreatic Ca. |
| CB22 | 72 | F | Pancreatic Ca. |

Figure 19B:
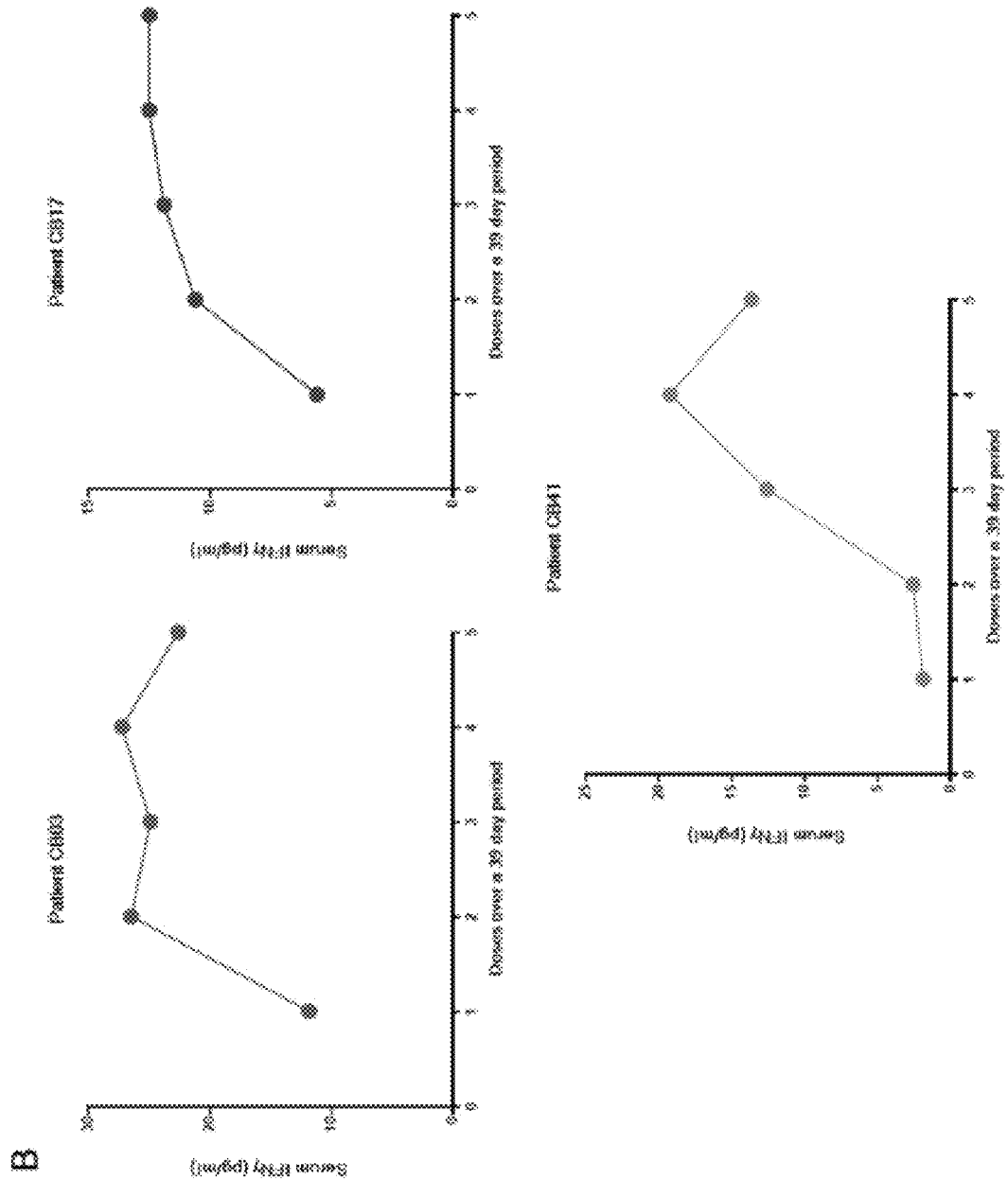
Figure 19C:
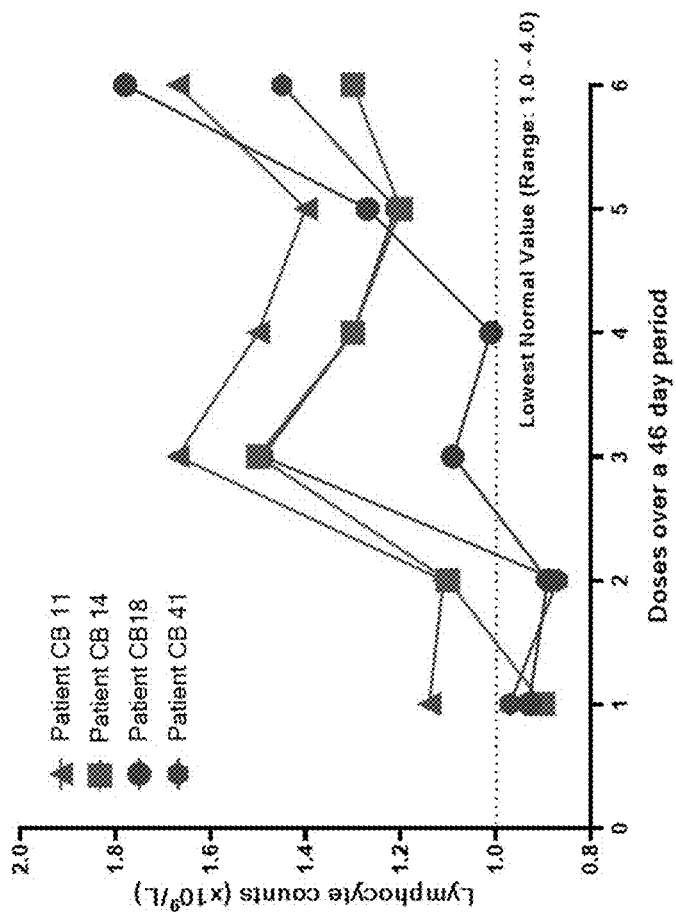

Every data point is an average value from 9 end-stage pancreatic cancer patients Similarly, FIGS. 19A-C show the results of administering a bacterial minicell comprising α-galactosylceramide (α-GalCer) to three pancreatic cancer patients (CB03, CB17, and CB41) over a 39 day period (FIGS. 19A and 19B), or 4 pancreatic cancer patients (CB11, CB14, CB18, and CB41) over a 46 day period (FIG. 19C). Measurement of serum IFN-α (pg/mL) (FIG. 19A) and serum IFN-γ (FIG. 19B) are shown on the Y axis of the graphs depicted in FIGS. 19A and 19B. The data shows that $EDV_{-aGc}$ elicits a Th1 response and increased lymphocyte levels in pancreatic cancer patients. More particularly, FIG. 19A shows a sustained increase in serum IFNα levels from all 3 patients following 2 doses of EDV-αGC, and FIG. 19B shows a sustained increase in serum IFNγ levels from all 3 patients following 2 doses of EDV-αGC. IFN levels were measured via ELISA from patients' blood serum samples taken throughout treatment cycles. Finally, FIG. 19C shows the results of measuring lymphocyte counts ($\times 10^9$/L) for four pancreatic cancer patients (CB 11, CB14, CB18, and CB41) over a 46 day period following 2 doses of $EDV_{-\alpha GC}$. The results depicted in FIG. 19C show a rise in lymphocyte counts to within normal range (1.0-4.0) in the four pancreatic cancer patients. Lymphocyte levels were measured from patient blood samples throughout treatment cycles, by pathology service.

The results, as detailed in FIGS. 4 and 19, are significant as proliferation of macrophages, dendritic cells and NK cells is critical to a successful immune defense of a viral infection.

Example 5

This example is directed to a study evaluating the feasibility of using bacterial minicells loaded with $EDV_{covid-\alpha GC}$ ($EDV_{Covid-\alpha GC}$) as a vaccine against SARS-CoV-2.

FIG. 5 shows a construct design for an $EDV_{-SARs-Cov-2}$ vaccine. The expression cassette was generated by placing the coding nucleotide sequence for SARS-Cov-2 (COVID-19) Spike protein (Genebank MN908947.3) on the 3'-end of a modified β-lactamase promoter, which has previously been used for expression in *Salmonella typhimurium* strains (Su et al., *Infection and Immunity,* 60(8):3345-3359 (1992)). The expression cassette was then inserted between the Kpn 5' and Sal I 3' sites of the M13 multiple cloning site of PUC57-Kan backbone plasmid to create P-Blac-Cov. FIGS. 10A and 10B.

α-GC and the spike protein, along with the plasmids encoding the spike protein DNA sequence, can be successfully incorporated into one single EDV (EDV$_{Covid-\alpha GC}$). The EDVs were then administered through subcutaneous (SC), intravenous (IV) and intra-muscular (IM) injections. It was found that administration through intra-muscular injections yielded the strongest initial interferon response 8 h post-injection as well as the highest spike protein specific IgG titres 1 week post-injection as compared to all other strategies tested.

EDV$_{covid}$-αGC and corresponding controls were then administered through intra-muscular injections and the incorporation of αGC in the EDVs resulted in a dramatic increase in IFNα, TNFα, IFNγ, IL12 and IL6 production 8 h post-treatment. This was accompanied by an increase in the amount of cytotoxic T-cells in the spleens of EDV$_{covid-\alpha GC}$ treated mice. These T-cells responded to the stimulation of the spike protein ex vivo and expressed CD69+ CD137+.

At 4 weeks post-initial treatment, mice injected with EDV$_{Covid-aGC}$ contained the highest amount of spike protein specific IgG and IgM as compared to all the controls tested. B-cells extracted from these mice were able to produce IgG and IgM ex vivo in response to spike protein stimulation. In addition, splenocytes from EDV$_{Covid-\alpha GC}$ treated mice contained the highest amount of anti-viral CD69+ CD137+ cytotoxic T-cells and ex vivo stimulation of these splenocytes using the spike protein yielded an increase in viral antigen specific CD69+ cytotoxic T cells. Moreover, the serum of EDV$_{Covid-\alpha GC}$ injected mice exhibited the strongest inhibition of spike protein binding to the hACE receptor in vitro, indicating the antibodies produced were neutralizing. Interestingly, the serum from mice that received any form of αGC also exhibited measurable but non-antigen-specific antiviral effect.

In summary, the incorporation of αGC into EDV$_{covid}$ is important for achieving maximum anti-SARS-CoV-2 spike protein efficacy. The results of this study indicate that I.M. administration of EDV$_{Covid-\alpha GC}$ is a viable strategy for combating the current Covid-19 pandemic.

Materials and Methods

Figure 10A:
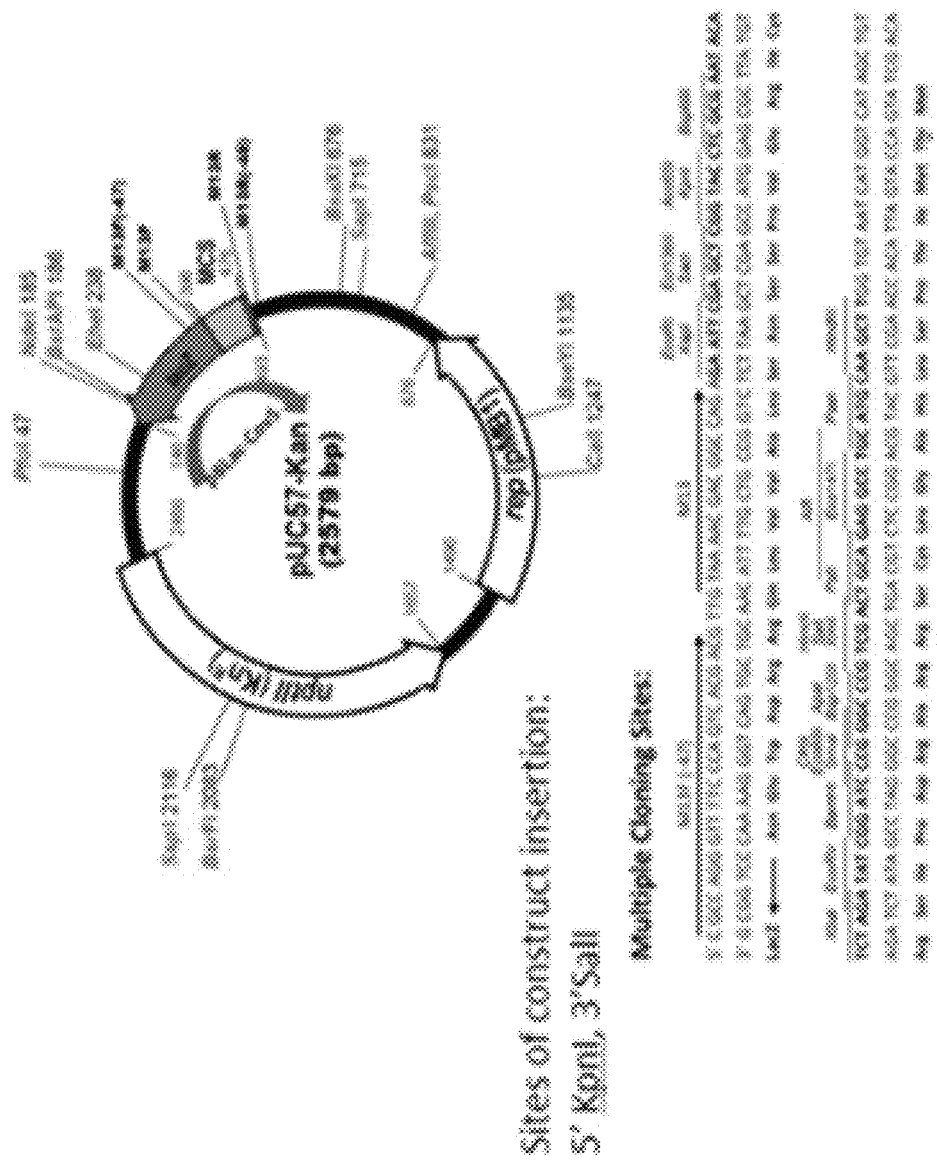
FIG. 10A shows a pUC57-Kan construct, with 5' Kpnl and 3'Sall sites of construct insertion, and FIG. 10A also discloses the first nucleotide sequence as SEQ ID NO: 1 and the amino acid sequence as SEQ ID NO: 2.
Figure 10B:
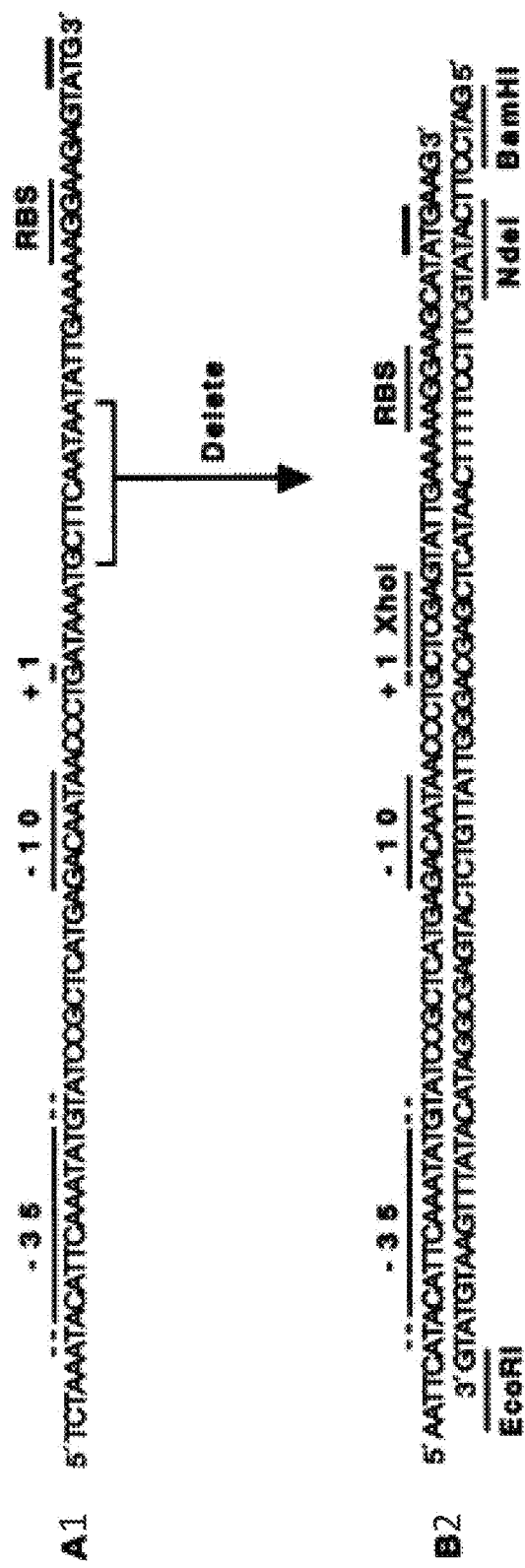
FIG. 10B shows in vitro synthesis of a synthetic modified-lactamase promoter. Nucleotide sequences of the native P-lactamase promoter (A1) and the synthetic, modified version (B2). The −35 and −10 regions, the +1 transcriptional start site, the ribosome binding site (RBS), and the ATG translation start codon are shown. The newly introduced EcoRI, XhoI, NdeI, and BamHI restriction enzyme sites are also indicated, and FIG. 10B also discloses SEQ ID NOS: 3-5, respectively, in order of appearance.

SARS-CoV-2 Spike protein bacterial expression plasmid design: The expression cassette was generated by placing the coding nucleotide sequence for SARS-Cov-2 (Covid-19) Spike protein (Genebank MN908947.3) on the 3'-end of a modified P-lactamase promoter, which has been previously tested for expression in *Salmonella typhimurium* strains (Su, Brahmbhatt et. al., *Infection and Immunity*, 60(8):3345-3359 (1992)). The expression cassette was then inserted between the Kpn 5' and Sal I 3' sites of the M13 multiple cloning site of PUC57-Kan backbone plasmid to create P-Blac-Cov2S. The control plasmid, P-Blac was created by removing the Cov2S sequence from the P-Blac-Cov2S (FIGS. 10A and 10B).

Cloning of P-Blac-Cov2S and P-Blac-Cov2S into *Salmonella Typhimurium* EDV producing strain and the subsequent incorporation of P-Lac-Cov2S and the spike protein into the EDVs: P-Blac-Cov2S and P-Blac-Cov2S were electroporated using a Gene Pulser Xcell™ (Bio-Rad, Hercules CA) into a chemically competent *Salmonella typhimurium* intermediate strain (4004), which lacks plasmid restriction mechanism, using settings 200 ohm, 25 Hz, 2.5 mV. Transformants were recovered in TSB medium for 1.5 hrs at 37° C. before plating on TSB agar plates containing 75 μg/ml kanamycin (#K4000, Sigma-Aldrich, St. Louis, Missouri). Isolates were picked into TSB broth with 75 μg/ml kanamycin and plasmid DNA extracted using the Qiagen miniprep kit as per manufacturer's instructions (#27104, Qiagen, Hilden, Germany). Subsequently, the extracted plasmid DNA from 4004 strain was electroporated as above into EnGeneIC Pty. Ltd. EDV producing *Salmonella typhimurium* strain (ENSm001). The bacteria that contained P-Blac-Cov2S would produce the encoded Covid2 spike protein, which alone with the plasmid DNA, would be incorporated into the EDVs to produce EDV$_{COVID}$. The EDVs containing P-Blac (EDV$_{CONT}$) would be used as a control.

To determine the plasmid content of EDV$_{COVID}$ and EDV$_{CONT}$, plasmids were extracted from 2×10$^9$ EDVs using a Qiaprep Spin miniprep kit (Qiagen) following the manufacturer's instructions. Empty EDV were treated the same was and used as controls. The quantity of DNA plasmids were then measured by absorption at 260 nm using a Biophotometer (Eppendorf). The copy-number of the plasmids were calculated using:

$$\text{Number of copies} = \frac{\text{amount} * 6.022 \times 10^{23}}{\text{length} * 1 \times 10^9 * 660}$$

Western Blot: Proteins from 2×10$^{10}$ EDV$_{COVID}$ were extracted using 100 μL B-PER™ (Thermo Fisher) bacterial protein extraction reagent supplemented with 10% (v/v) lysozyme (Sigma-Aldrich) and 1% (v/v) DNaseI (Qiagen). The extracted samples were then centrifuged at 12,000 g for 10 min and the supernatant was collected. The left-over pellet was also collected and resuspended in 100 μl PBS. 23 μl of the supernatant and pellet protein samples were co-incubated with 5 μl of loading buffer and 2 μl DTT (Sigma-Aldrich) at 80° C. for 20 min before the entire content of each sample was loaded onto a NuPAGE 4-12% Bis-Tris mini gel (Life Technologies) and run at 190 V for ~80 min. The sample was then transferred using an iBlot 2 machine and the membrane was blocked using Superblock blocking buffer (Thermo Fisher) and subsequently stained with 1:2000 Rabbit poly-clonal SARS-CoV2 spike antibody (also cross-reacts with the S1 subunit, Sino Biological, Beijin, China) and incubated overnight at 4° C. The membrane was then washed with PBST and incubated with HRP conjugated anti-rabbit secondary antibody (1:5000) (Abcam) for 1 h at room temperature. The blot was developed using Lumi-Light Western Blot substrate (Roche) and visualised using a Chemidoc MP (Biorad).

Alpha-galactosylceramide loading into EDV$_{COVID}$ and cell culture: α-galactosylceramide glycolipid adjuvant (α-GC) was loaded into EDV$_{COVID}$ to created EDV$_{COVID-\alpha GC}$.

JAWSII cells (ATCC) were treated with EDV$_{COVID-\alpha GC}$ in a 96-well Perfecta3D hanging drop plate (Sigma) at 1×10$^4$ EDV$_{COVID-\alpha GC}$ per cell. JAWSII cells treated with 4 μg/mL α-GC was used as a positive control. The cultures were then incubated for 24 h at 37° C. with 5% CO$_2$ and cells were collected and stained with a CD1d-αGC antibody (ThermoFisher) and analysed using a Gallios flow cytometer (Beckman). The results were analysed using Kaluza Analysis software (Beckman).

Animal studies: Female Balb/c mice, 6-7 weeks old were obtained from the Animal Resources Company in Western Australia. The mice were acclimatized for one week before the experiments commenced. The mice were injected with appropriate treatments through SC and IM injections and serum was collected 8 h, 1 week and 4 weeks post-injection through the tail vein and the spleen and bone marrows were collected.

Enzyme-linked immunosorbent assay: The levels of IL-12p40, IFN-γ, TNFα, IL-6, IL2, IFNα and IFNβ in the mouse serum were measured by standard sandwich enzyme-linked immunosorbent assay (ELISA) from R&D Systems according to manufacturer's instructions. The concentrations of the protein present were determined by calculating absorbance of the samples again standards curves constructed within the same assay using purified proteins.

For analysis of anti-RBD specific IgG and IgM antibodies, 96-well plates (Immulon 4 HBX; Thermo Fisher Scientific) were coated at 4° C. with 50 μl per well of a 2 μg/ml solution of anti-covid spike RBD protein (Genetex) suspended in PBS (GIBCO). On the following day, the coating protein solution was removed and the samples in each well were blocked using 100 μl per well of 3% non-fat milk prepared in PBS with 0.1% Tween 20 (PBST) at room temperature for 1 h. During this time, serial dilutions of mouse serum were prepared in 1% non-fat milk prepared in PBST. The blocking solution was then removed and 100 μl of each serial diluted serum sample was added to the plates and incubated for 2 h at room temperature. At the end of incubation period, the plates were washed three times with 250 μl per well of 0.1% PBST, before adding 100 μl of 1:3,000 dilution of goat anti-mouse IgG/IgM-horseradish peroxidase (HRP) conjugated secondary antibody (ThermoFisher) prepared in 0.1% PBST. The samples were incubated at room temperature for 1 h and then were again washed three times with 0.1% PBST. Once completely dry, the samples were visualised by incubating with TMD. The reactions were then terminated and the samples were read at 490 nm using a KC Junior plate reader (BioTek Instruments).

Antibody titre was determined using ELISA by generating 1:3 serial dilution of the treated mouse serum samples and is expressed as the inverse of the highest dilution with a positive result.

Statistical analysis: Student's T-tests and One-way ANOVA was conducted using Prism 8 (GraphPad). A P value of <0.05 is considered to be statistically significant.

Results

Figures 11A, 11B:
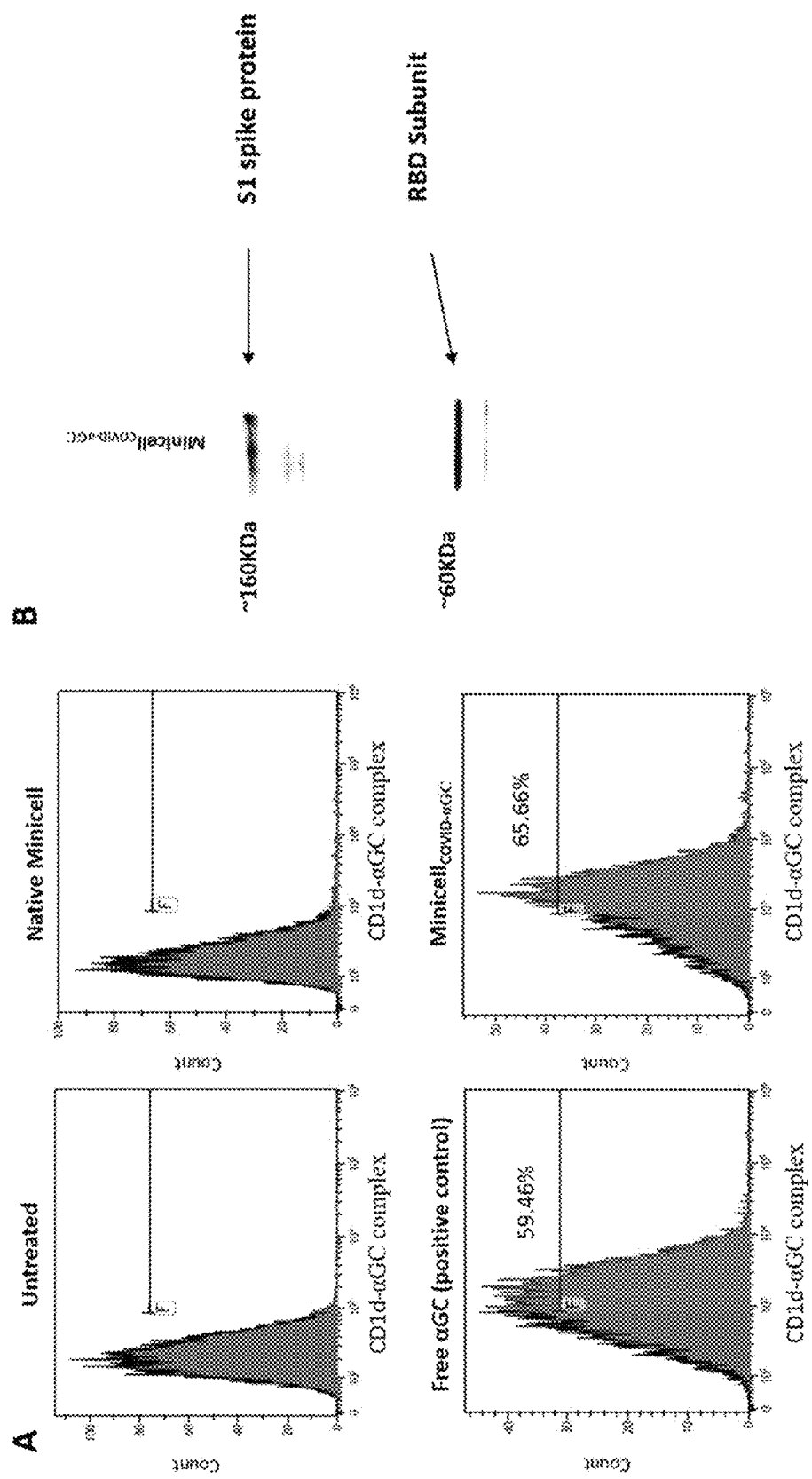
FIGS. 11A and 11B shows that treatment with JAWSII cells with EDV$_{Covid\text{-}αGC}$ resulted in the expression of αGC through CD1d ligand onto the surface of the cells. The level of expression was better than JAWSII cells treated with free αGC alone (FIG. 11A). Western blot analysis of EDV$_{Covid\text{-}αGC}$ showed that the spike protein is incorporated into the structure EDVs (FIG. 11B).

To achieve effective and efficient delivery of the vaccine with one single injection, αGC was co-loaded into $EDV_{covid}$ to create $EDV_{covid-aGc}$. The function of the co-loaded αGC was tested by examining its presentation on JAWSII cells via CD1d ligand following $EDV_{covid-aGc}$ treatment. FIG. 11A shows the results of mouse experiments, where four groups of mice were evaluated (Group 1=untreated; Group 2=EDVs with no payload; Group 3=administration of free αGC; and Group 4=administration of a bacterial minicell vaccine comprising a combination of SARS-CoV-2 Spike protein and αGC. It was found that a high percentage of JAWSII cells expressed CD1d-αGC following the treatment at a comparable or higher level than those that were treated with 3 μg/mL of free αGC (FIG. 11A). Thus, the data shown in FIG. 11A demonstrates that EDV™-COVID-α-GC was able to effectively deliver α-GC into murine bone marrow derived, JAWSII, cells and presented through CD1d-ligand to a similar efficiency as free α-GC.

Western blot analysis was conducted to ensure the spike protein incorporated into the EDVCovid-αGC was not affected by the secondary incorporation of αGC (FIG. 11B). In particular, FIG. 11B shows a Western blot analysis using a polyclonal antibody against the RBD and the S1 subunit, with the results demonstrating the presence of the spike protein within the EDV™-$_{COVID-\alpha GC}$. Incorporation of the bacterially expressed protein into EDV™s occurs during cell division and segregation of the cytoplasmic proteins.

The effect of different delivery methods for the $EDV_{Covid-\alpha GC}$ on groups of BALB/c mice was assessed in vivo. FIGS. 6A and 6B show the response in groups of Balb/c mice 1 week post dose of $EDV_{COVID-\alpha GC}$ ($2 \times 10^9$ day 1 first dose). The groups of mice were: Group 1=saline, SC administration; Group 2=EDV, SC administration (bacterial minicell with no payload); Group 3=$EDV_{control}$, SC administration (EDVs carrying the plasmid with no insert expressing the Spike protein i.e. plasmid backbone only); Group 4=$EDV_{Covid}$, SC administration (bacterial minicell comprising a SARS-CoV-2 spike protein); Group 5=$EDV_{Covid+\alpha GC}$, SC administration; and Group 6=$EDV_{Covid+\alpha GC}$, IM administration. Group 6 shows the most significant serum IgG titres (FIG. 6A), as well as the most significant total AUC for IgG (FIG. 6B), both measured at 1 week post dose.

FIGS. 7A-7E show the response in groups of Balb/c mice four weeks post I.M dose of $EDV_{COVID-\alpha GC}$ ($2 \times 10^9$ day 1 first dose; $1 \times 10^9$ day 21 second dose). The five groups of mice (n=6 per group) were: Group 1=saline; Group 2=EDV (bacterial minicell with no payload); Group 3=$EDV_{control}$ (EDVs carrying the plasmid with no insert expressing the Spike protein i.e. plasmid backbone only); Group 4=$EDV_{Covid}$ (bacterial minicell comprising a SARS-CoV-2 spike protein) and Group 5=$EDV_{Covid+\alpha GC}$. Mouse serum samples were collected and analysed via ELISA levels for serum-IFNα concentration (pg/mL) (FIG. 7A), serum IFNγ concentration (pg/mL) (FIG. 7B), serum IL12 concentration (pg/mL) (FIG. 7C), serum IL6 concentration (pg/mL) (FIG. 7D) and serum TNFα concentration (pg/mL) (FIG. 7E). It was found that $EDV_{Covid-\alpha GC}$ was vastly superior at inducing the production of all the cytokines tested in mice.

Figures 20A, 20B:
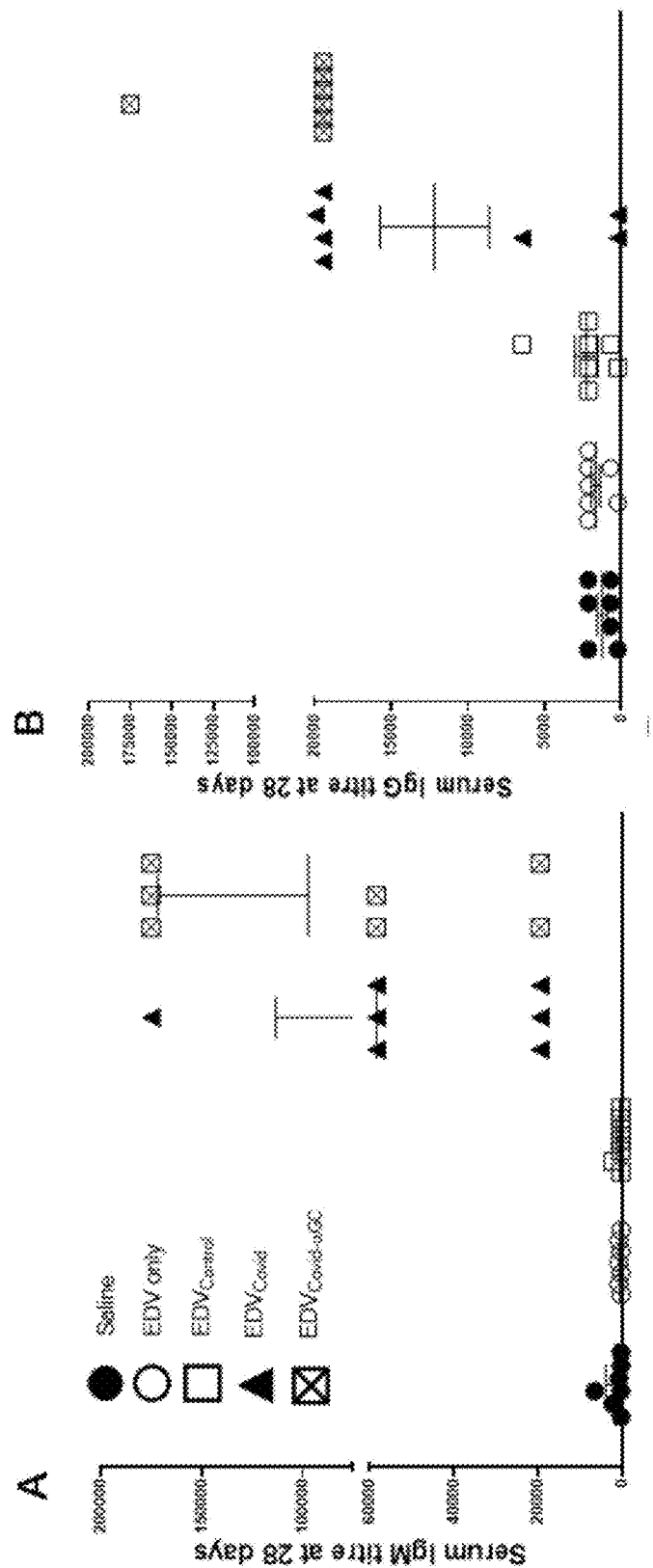
FIGS. 20A and 20B show the response in Balb/c mice (n=8 per group) four weeks post I.M dose of EDV-COVID-αGC ($2\times10^9$ day 1 first dose; $1\times10^9$ day 21 second dose). High levels of anti-S protein IgM (FIG. 20A) and IgG (FIG. 20B) antibody titers were detected in the serum of the mice immunized with EDV-COVID-α-GC at 28 days post-initial dose, with a booster administration at 21 days.
Figures 21A, 21B, 21C, 21D:
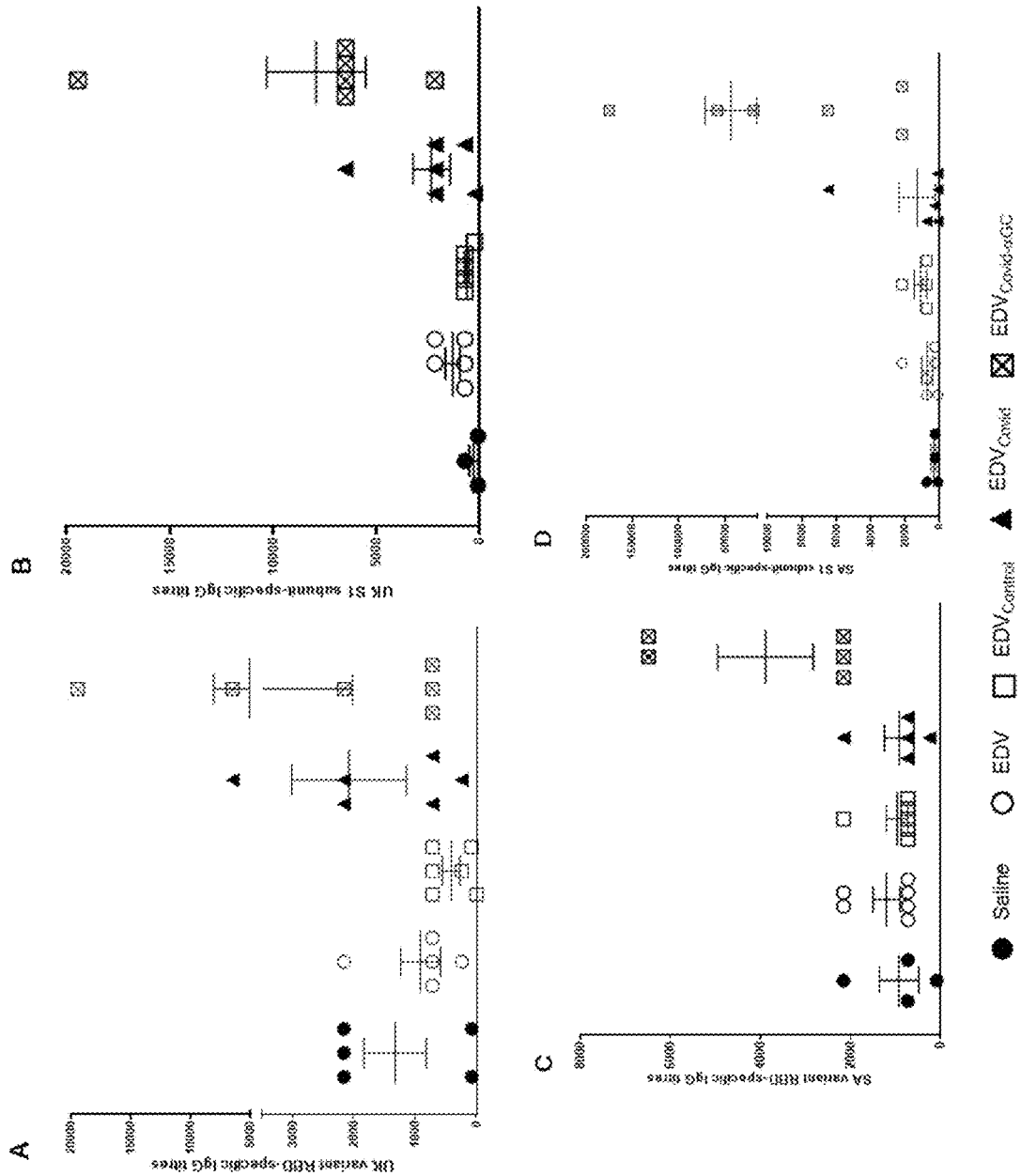
FIGS. 21A-21D shows the robustness of the immunity generated by EDV-COVID-α-GC by analyzing the specificity and cross-reactivity of the serum IgG from immunized mice against the RBD and S1 subunits of the UK (B.1.1.7) and South Africa (B.1.351) variants of the virus. The results showed that, while UK variant RBD-specific IgG was produced in some of the EDV-COVID-α-GC immunized mice (FIG. 21A), a much greater S1-specific IgG antibody titer was observed (FIG. 21B) indicating the binding of the S protein-specific antibody lands mainly outside of the RBD. A similar An exemplary viral infection to be treated or vaccinated against includes coronaviruses, including but not limited to the coronavirus SARS-CoV-2, infection which causes Coronavirus Disease 2019 (COVID-19). Thus, by way of example, this description describes the development of an intact, bacterially derived minicell-based therapeutic and/or vaccine against SARS-CoV-2 coronavirus infections in humans. In yet another aspect, encompassed is a composition comprising a combination of (a) an intact, bacterially-derived minicell comprising at least one viral antigen from SARS-CoV-2 and (b) an intact, bacterially-derived minicell comprising the CD1d-recognized antigen α-GalCer. In one aspect, the intact, bacterially-derived minicell comprising at least one viral antigen from SARS-CoV-2 can comprise all four of the constituent proteins of SARS-CoV-2, or antigenic fragments thereof, e.g., the spike (S) protein, nucleocapsid (N) protein, membrane (M) protein, and the envelope (E) protein.

High levels of anti-S protein IgM (FIG. 20A) and IgG (FIG. 20B) antibody titers were detected in the serum of the mice immunized with $EDV_{-COVID-\alpha-GC}$ at 28 days post-initial dose, with a booster administration at 21 day. The difference between the different methods of administration of $EDV_{Covid-\alpha GC}$ was further demonstrated when spike protein specific antibodies were analyzed at 1 week post-initial injection. High spike protein specific IgG titre was detected in the serum of $EDV_{Covid-\alpha GC}$ treated mice through I.M. injections compared that of through S.C. injections. It was concluded that due to the high levels of initial interferon response and subsequent high IgG titres, administration of $EDV_{Covid-\alpha GC}$ through I.M. injection was the preferred delivery strategy.

Figure 8A:
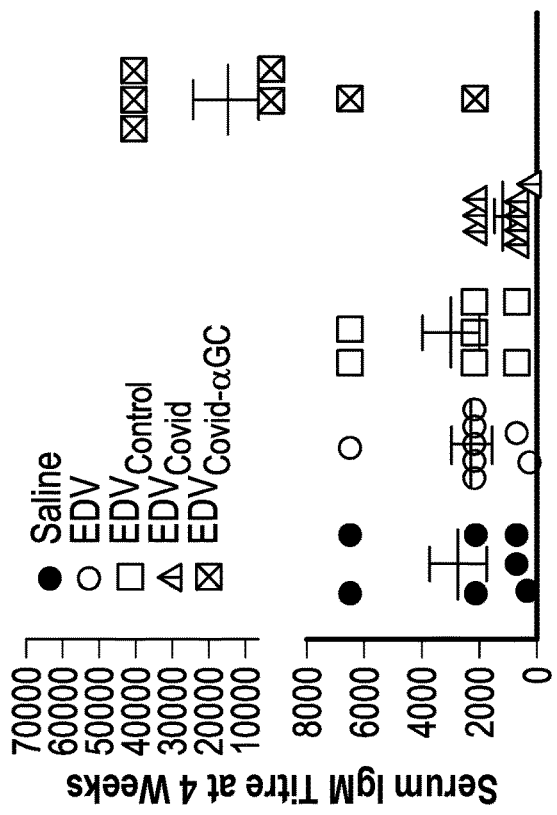
FIGS. 8A and 8B shows that mice injected with bacterial minicells loaded with Covid-αGC (EDV$_{Covid\text{-}αGC}$) had the highest levels of serum IgM (FIG. 8A) and IgG (FIG. 8B) at 4 weeks (boost on day 21) post-initial injection.
Figure 8B:
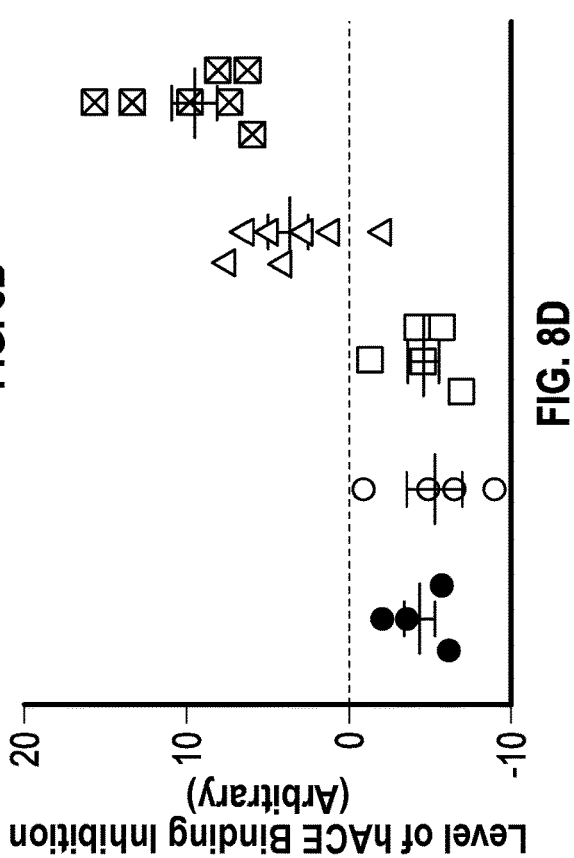
Figure 8C:
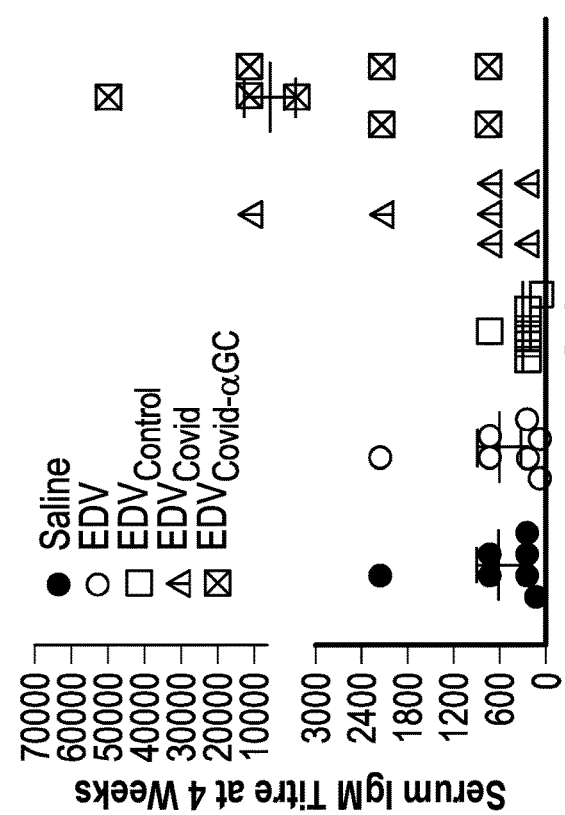
FIG. 8C shows an ELISA analysis demonstrating that bone-marrow derived B cells were able to produce spike protein specific IgG ex vivo when incubated with spike protein.
Figure 8D:
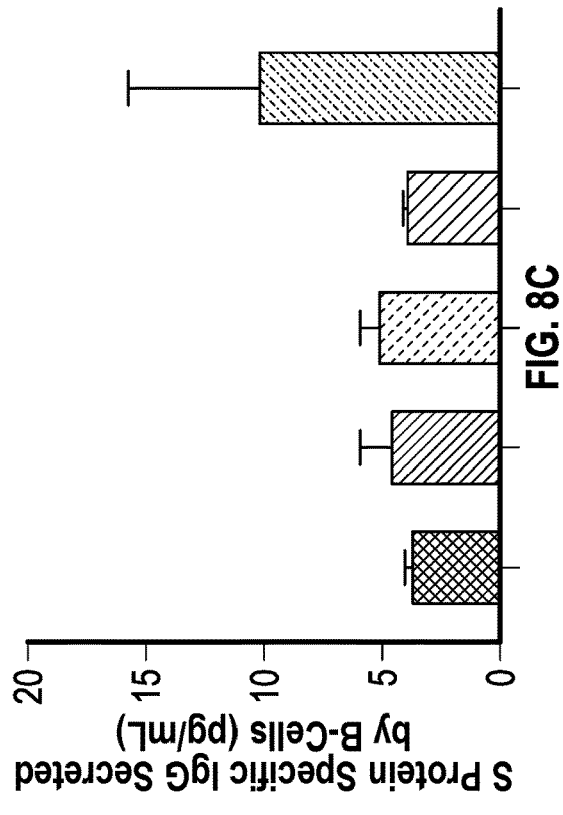
FIG. 8D shows a neutralising antibody analysis at 4 weeks post-initial dose.

FIGS. 8A-D show the results following isolation of B-cells from the mouse bone marrow at 28-day post-initial injection and co-incubation with the SARS-CoV-2 S protein ex vivo. FIGS. 8A and 8B show the serum IgM and IgG titres, respectively, at 4 weeks post injection, with the group administered $EDV_{Covid-\alpha GC}$ showing the highest titres. It was found that B-cells isolated from $EDV_{-COVID-\alpha-GC}$ immunized mice produced a significantly greater amount of S protein-specific IgG in response to the presence of S protein as compared to all other groups tested (FIG. 8C). FIG. 8D shows the results of a neutralizing antibody assay, which demonstrated that the serum of 100% of the mice immunized with EDV-COVID-α-GC resulted in SARS-CoV-2 RBD binding inhibition to hACE2 receptor. The cPASSTM SARS-Cov-2 Neutralizing Antibody Assay (FDA approved; Tan et al, *Nature Biotech*, 2020) for detection in various species was used to assess inhibition of RBD binding to hACE2 receptor. FIG. 8E shows an IgG subtype analysis of the $EDV_{Covid}$ and $EDV_{Covid-\alpha GC}$.

Figures 12A, 12B, 12C, 12D:
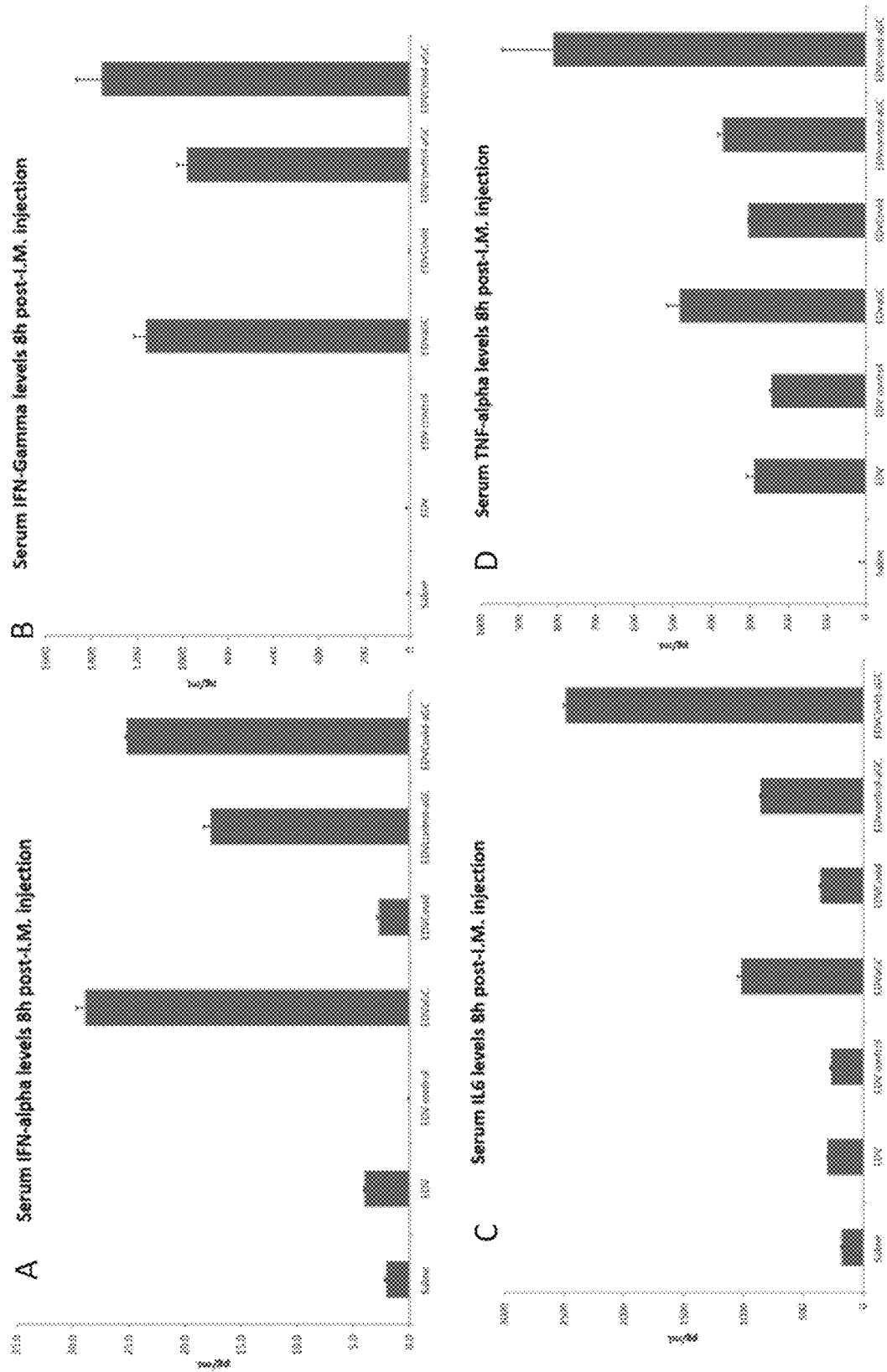

Detailed analysis of initial interferon response 8 hrs following I.M. injections of EDV, $EDV_{aGC}$, $EDV_{Control}$, $EDV_{Control-\alpha GC}$, $EDV_{Covid}$, $EDV_{Covid-\alpha GC}$ showed that the early interferon response in mice was predominantly induced by the administration of αGC carried by EDVs with or without an accompanying antigen-specific plasmid. See FIG. 12A (serum IFNα concentration); FIG. 12B (serum IFNγ concentration); FIG. 12C (IL6 serum concentration); FIG. 12D (serum TNFα, concentration); and FIG. 12E (IL12p40 serum concentration 8 h).

FACS analysis of mouse splenocytes at 1 week post-injection showed that there is an increase in CD3+ CD8+ cytotoxic T-cell number in the $EDV_{Covid-\alpha GC}$ injected mice as compared to the saline group (FIG. 13A). AIMS assay was conducted on the ex vivo splenocytes and it was found that there is an increase in viral antigen-specific CD69+ CD137+ population within the cytotoxic T-cell population when stimulated with the spike protein, at a higher level as compared to the PHA stimulated positive controls (FIG. 13B). In particular, the results depicted in FIG. 13 demonstrate that mice immunized with $EDV_{COVID-\alpha-GC}$ had the highest amount of antigen-specific memory CD137+ CD69+ cytotoxic T-cell at 4 weeks (1 boost at day 21) post-initial injection, e.g., there were significantly high number of CD137+ CD69+ population within the cytotoxic T-cell population in the $EDV_{Covid-aGC}$ treated mice as compared to all other treatment groups. CD137+ signalling is essential in the CD8+ T cell anti-viral response.

FIG. 9 shows the results of an ex-vivo AIMS Assay showing Spike antigen specific CD8+ T cell response. There is an increase in the CD69+/CD8+ T cell numbers following the stimulation with Covid Spike protein in the EDV-Covid and EDV-Covid-αGC groups but not in any other groups. PHA was used as a positive control. These results indicate that both plasmid and protein contained within EDVs creates a specific response. Thus, FACS analysis of ex vivo splenocytes from treated mice showed that $EDV_{Covid-\alpha GC}$ treatment resulted in an increase in CD69+ CD137+ cytotoxic T-cells as compared to all other treatment conditions (FIG. 9A). It was also observed that when the ex vivo spherocytes were stimulated with the spike protein, there was an increase in viral antigen specific CD69+ CD137−cells within the cytotoxic T-cell population at a similar rate as compared to the PHA stimulated positive controls from $EDV_{Covid-\alpha GC}$ and $EDV_{covid}$ treated mice (FIG. 9B). This was not observed in all the other treatment groups. It indicates that, unlike the anti-viral response triggered by $EDV_{Covid-\alpha GC}$ treatment, the anti-viral property of αGC may be broad spectrum and not antigen-specific.

Figures 14A, 14B, 14C:
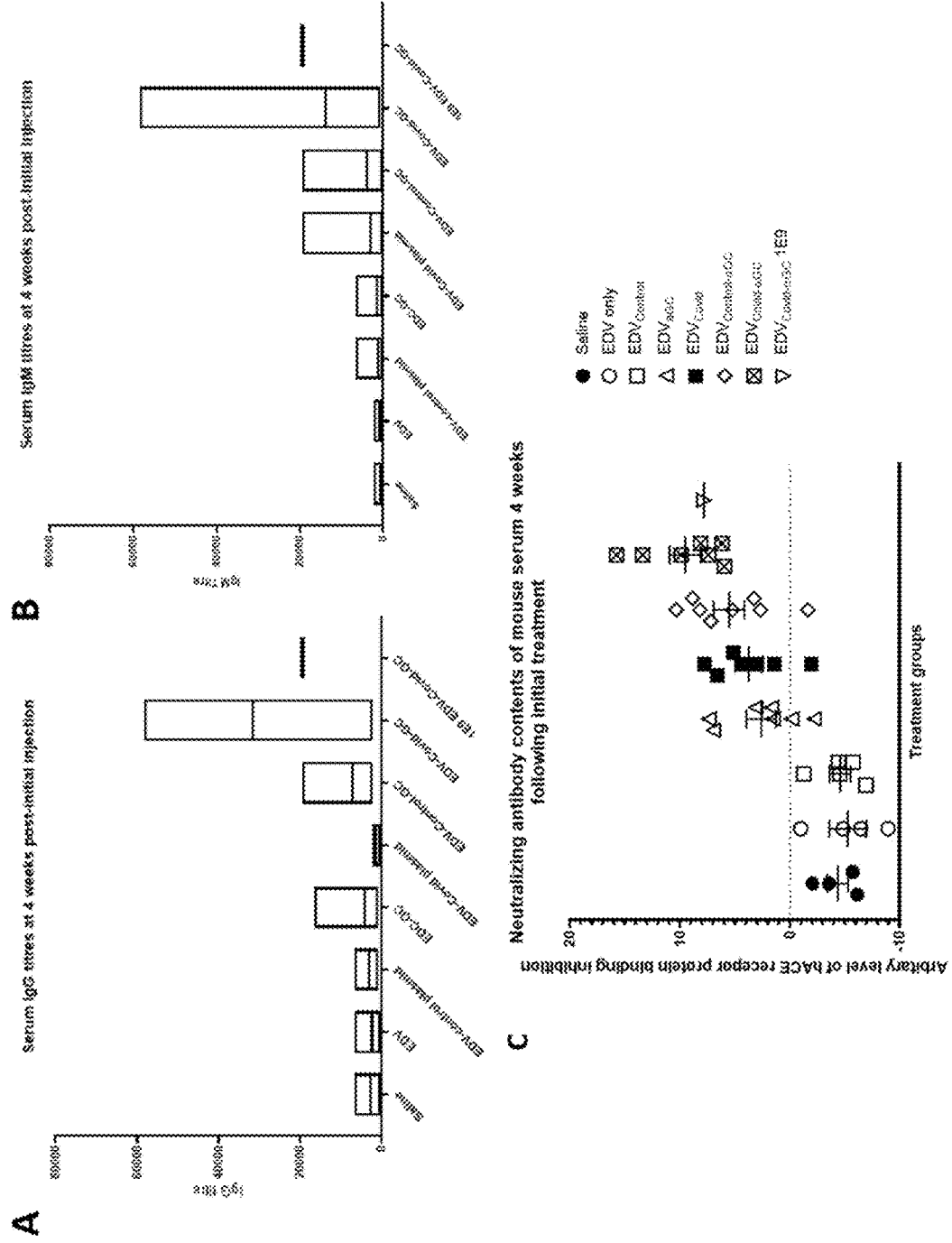
FIGS. 14A-14C shows that high levels of spike protein specific IgG were found in the serum of the mouse treated with EDV$_{Covid\text{-}αGC}$ 4 weeks post-initial injection (FIG. 14A); this was also found for spike protein specific IgM (FIG. 14B). Interestingly, while the serum of mice treated with EDV$_{Covid\text{-}αGC}$ exhibited the highest degree of inhibition of the binding of spike protein to hACE receptor protein, the treatment of containing EDV$_{aGC}$ also demonstrated ability to prevent spike protein binding (FIG. 14C).

At 4 weeks post-initial injection, the highest levels of spike protein specific IgG (FIG. 14A) and IgM (FIG. 14B) were observed in the serum of the mice that were treated with $EDV_{Covid-\alpha GC}$ administered through I.M. injections. Interestingly, it was also found that the serum of mice treated with $EDV_{Control-\alpha GC}$ also contained spike protein "specific" antibodies. This finding was confirmed by neutralizing antibody analysis. While the serum of mice treated with $EDV_{Covid-\alpha GC}$ contained the highest amount of neutralizing antibodies, serums of mice treated with $EDV_{Control}$-αGC, $EDV_{Covid}$ and EDV $_{\alpha GC}$ also resulted in measurable degree of spike protein to hACE receptor binding inhibition (FIG. 14C). It appeared that αGC alone has anti-viral properties in which the administration of the compound could result in the inhibition of viral binding to the cells in the body. On the other hand, injecting $EDV_{Covid}$ by itself without the addition of αGC was capable of producing neutralizing antibodies in the serum, albeit at much lower levels compared to that of treated with $EDV_{Covid-\alpha GC}$. This demonstrated the importance of incorporating αGC as an immuno-adjuvant in this system as a vital part of a functional vaccine.

Figure 15A:
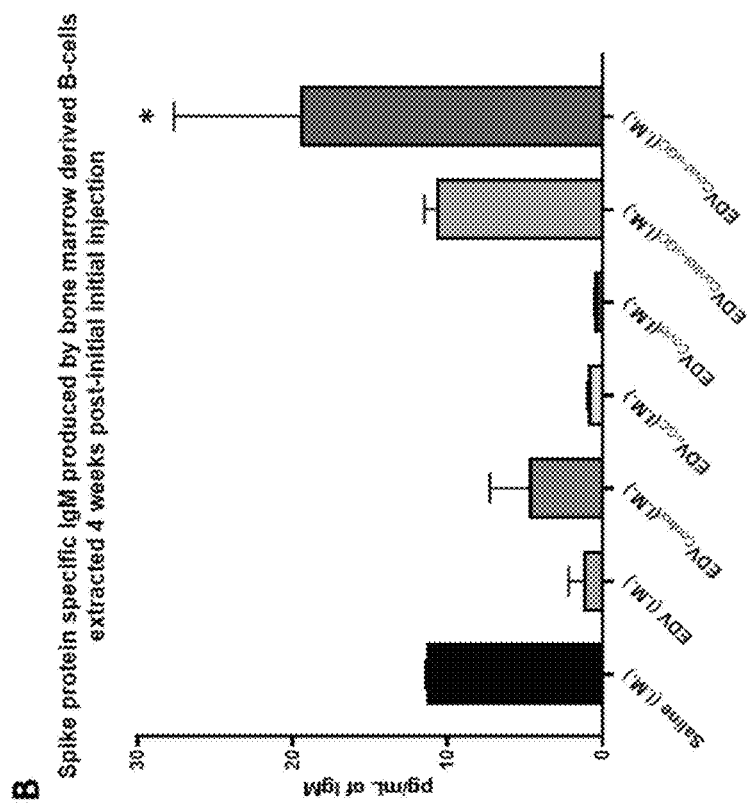
FIGS. 15A and 15B shows the results of an experiment where B-cells extracted from the bone marrow of EDV$_{Covid\text{-}αGC}$ treated mice at a 4 week time point secreted the highest level of spike protein specific IgG (FIG. 15A) and IgM (FIG. 15B) as detected by a modified version of ELISA.
Figure 15B:
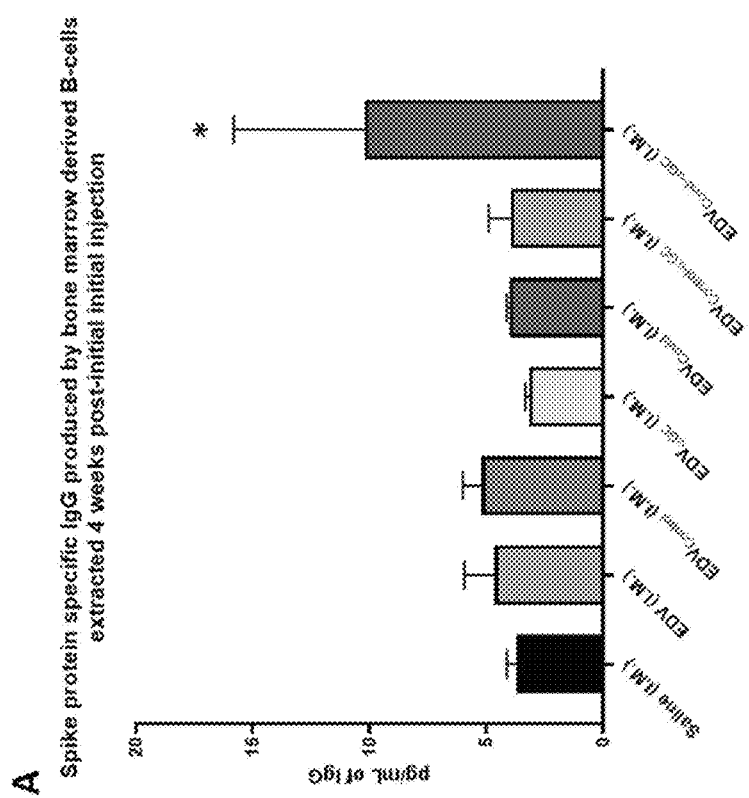

To further demonstrate the specificity of the antibody response, B-cells were extracted from the bone marrow of the treated mice at 4 weeks post-initial injection and stimulated with spike protein for 48 h in vitro. B cells from mice treated with $EDV_{Covid-\alpha GC}$ produced the highest level of spike protein specific IgG (FIG. 15A) and IgM (FIG. 15B) as compared to all other treatment groups.

Example 7

The purpose of this example is to describe preparation of a SARS-CoV-2 vaccine comprising an antigen of a SARS-CoV-2 vaccine variant.

Figure 16A:
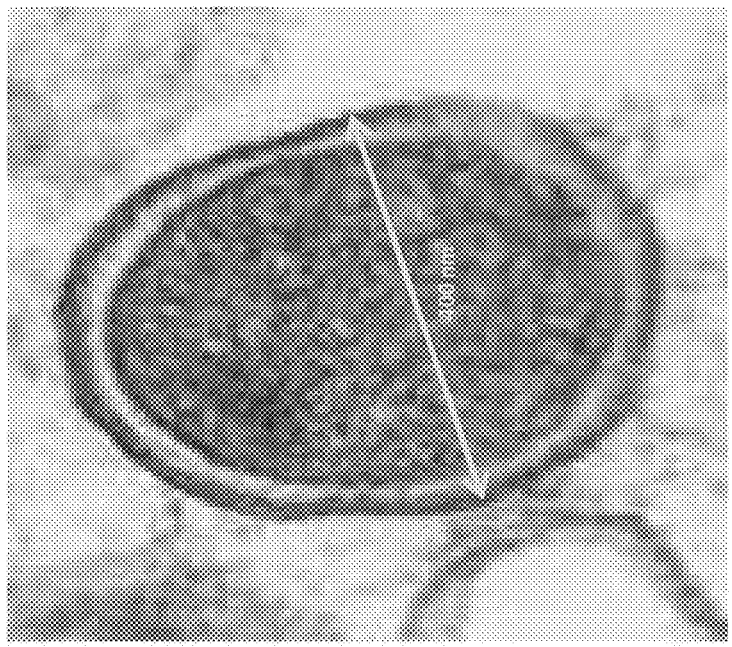
FIG. 16A depicts a scanning electron microscope image showing production of an EnGeneIC Dream Vector (EDV™) nanocell, i.e., an intact, bacterially derived minicell, from a safe bacterium *Salmonella typhimurium* strain.
Figure 16B:
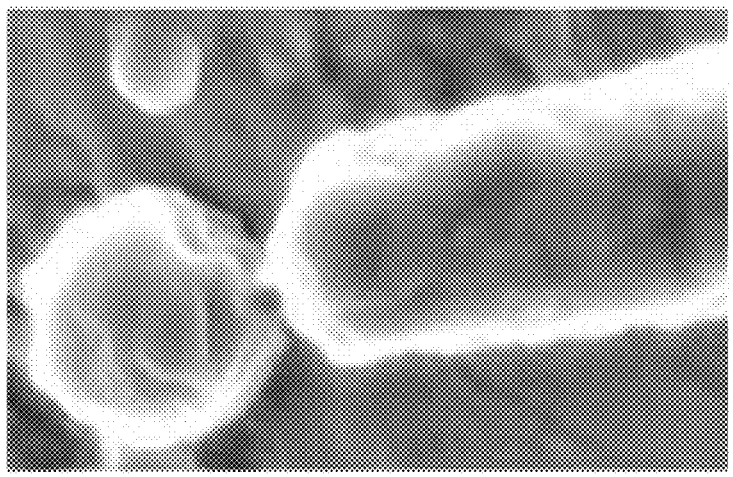
FIG. 16B depicts a transmission electron micrograph image showing the structure of an empty EDV bacterial nanocell, with a diameter of about 400 nm.

FIG. 16A depicts a scanning electron microscope image showing production of an EnGeneIC Dream Vector (EDV™) nanocell, i.e., an intact, bacterially derived minicell, from a safe bacterium *Salmonella typhimurium* strain, and FIG. 16B depicts a transmission electron micrograph image showing the structure of an empty EDV bacterial nanocell, with a diameter of about 400 nm. The vectors, or bacterial minicells, are used as carriers for SARS-CoV-2 variant antigens, SARS-CoV-2 antigens, and the adjuvants described herein.

Figures 17A, 17B:
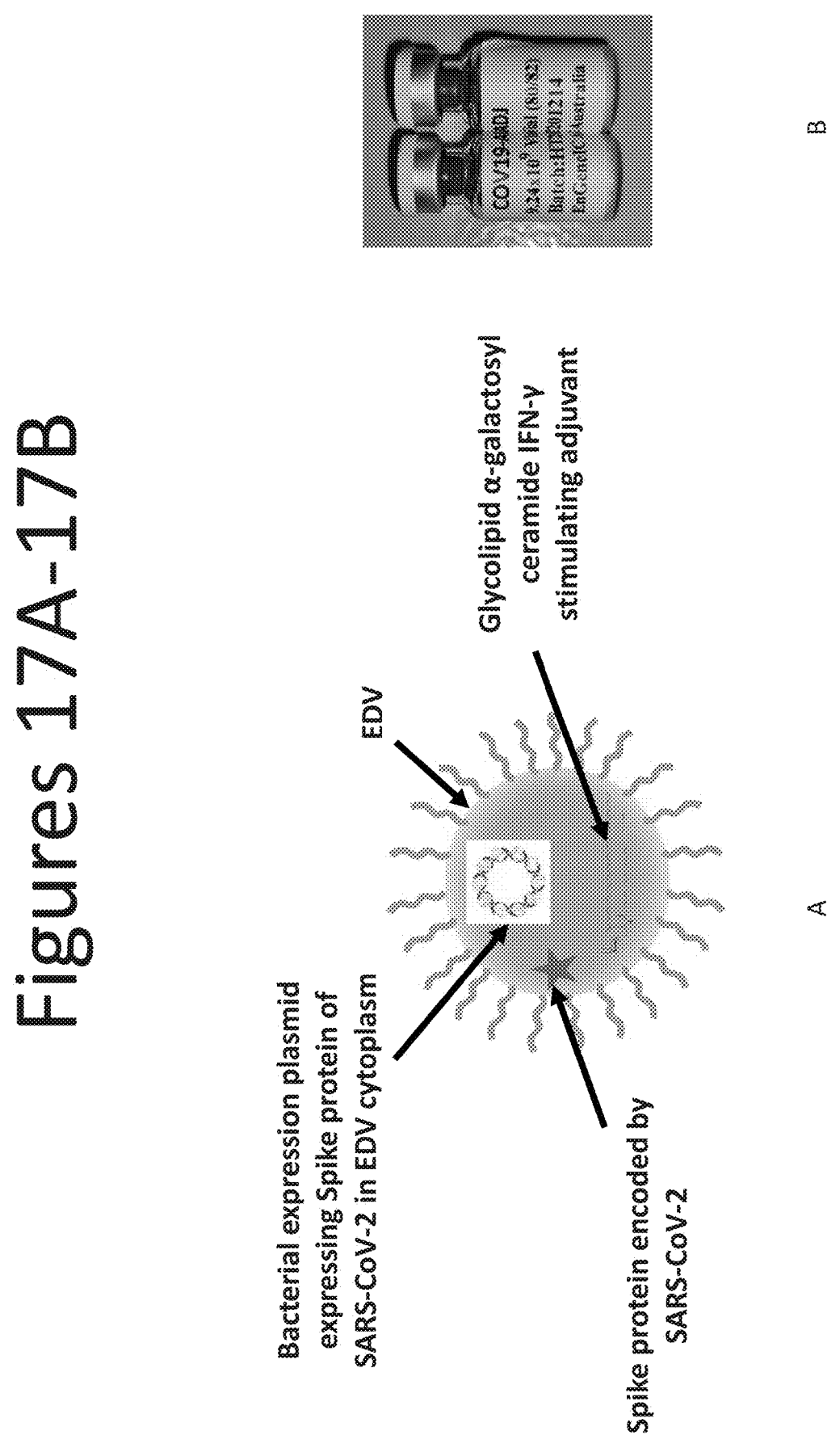

FIG. 17 is a graphical depiction of an EDV-COVID-19 vaccine composition, comprising a bacterial expression plasmid ("EDV"), wherein the EDV first expresses Spike protein of SARS-CoV-2 in the EDV cytoplasm and additionally carrys or is loaded with the CD1d-restricted iNKT cell antigen glycolipid α-galactosylceramide (α-GalCer) IFN-γ as an adjuvant or stimulating agent. Expressed Spike protein encoded by SARS-CoV-2 is designated by a star on FIG. 17A. FIG. 17B shows an exemplary vial containing lyophilized EDV-COVID-19 vaccine composition.

FIG. 18 is a graphical depiction of an EDV-COVID-19 vaccine composition, comprising an intact, bacterial mini-cell comprising an expression plasmid, wherein the bacterial minicell comprises (i) a plasmid expressing cloned Spike proteins from original SARS-CoV-2, SARS-CoV-2 delta variant, and SARS-CoV-2 Brazil variant, (ii) a gene expression promotor expressing all proteins as a single mRNA and separate proteins in the EDV cytoplasm, (iii) multiple Spike proteins, including Spike protein produced by SARS-CoV-2, Brazil variant Spike Protein, and delta variant Spike protein, and (iv) the CD1d-restricted iNKT cell antigen glycolipid α-galactosylceramide (α-GalCer) IFN-γ as an adjuvant or stimulating agent. Expressed Spike proteins encoded are designated by starts on FIG. 18. Upon administration to a subject in need, the vaccine composition functions to stimulate antibody responses to the viral proteins. Plasmid double-stranded DNA is recognized by intracellular nucleic acid sensors and triggers IFNα and IFNβ response.

The product can be lyophilized. The intact bacterially-derived minicell based products are very stable and lyophilized vials with anti-cancer compounds and intact bacterially-derived minicell loaded with α-GC have already shown stability for more than 3 years when the vials are simply stored at 4° C. in a normal fridge at the hospital pharmacy. They can be shipped anywhere in the world via a courier, which has previously been demonstrated for US cancer trials using EDVs (e.g., bacterial minicells).

Patient dosing: When a patient is to be dosed, the vial can be reconstituted in 1 ml of sterile physiological saline and injected i.v. as a bolus injection.

The plasmid encoding the SARS-CoV-2 viral and viral variant proteins can be transformed into the intact bacterially-derived minicell producing strain and it would express the viral proteins in the bacterial cytoplasm. When the intact bacterially-derived minicell is produced during asymmetric bacterial division a lot of the protein is segregated into the intact bacterially-derived minicell cytoplasm. This has been demonstrated in in several studies where heterologous foreign proteins have been expressed in intact bacterially-derived minicell producing bacterial cells and the proteins segregate into the intact bacterially-derived minicell cytoplasm.

The expected results from plasmid-packaged intact bacterially-derived minicells is an antibody response to all the virus proteins, plus a Type I interferon response.

The injected intact bacterially-derived minicells would be rapidly engulfed by the cells of the immune system (macrophages, NK cells and dendritic cells) in the lymph nodes, liver and spleen. The intact bacterially-derived minicells normally enter the endosomes and are broken down in the lysosomes and the plasmid is released which escapes into the cytoplasm.

Cytosolic DNA sensors, which would recognize the plasmid DNA, are a class of pattern recognition receptors (PRRs), which induce the production of type I interferons (IFNα and IFNβ) and trigger the induction of a rapid and efficient innate immune response. It is well known that Type I interferons have a potent antiviral effect.

The SARS-CoV-2 viral and viral variant proteins are released from the broken down intact bacterially-derived minicells in the lysosomes and undergo antigen processing and presentation via MHC Class II on to the cell surface. This triggers a potent antibody response to the viral antigenic epitopes. This further provokes a CD4+/CD8+ T cell response against virally infected cells and this should augment the anti-viral response.

The activation maturation and proliferation of fresh bone marrow derived monocytes along with the activation and proliferation of macrophages, dendritic cells, NK cells, B cells and T cells would be expected to overcome the observed lymphopenia in the elderly and immune-compromised SARS-CoV2 patients.

Expected results from α-galactosyl ceramide packaged intact bacterially-derived minicells —induction of IFN-γ response: EDV™α-GC are also engulfed by cells of the immune system (macrophages, NK cells and dendritic cells) in the lymph nodes, liver and spleen. The intact bacterially-derived minicells are broken down in the intracellular lysosomes and the α-GC is released which is picked up by lysosomally associated CD1d (MHC Class I like molecule which is involved in the presentation of foreign glycolipids) and transported to the cell surface. This α-GC/CD1d complex is recognized by the invariant T cell receptor on invariant NKT cells and this results in the rapid release of IFN-γ. IFN-γ is known to be a potent stimulator of a specific anti-viral immune response which would then be expected to augment the rejection of the viral infection.

The intact bacterially-derived minicell therapeutics have already been shown to be safe in human cancer patients where over 1,500 doses have been administered in over 140 patients with minimal to no side effects despite repeat dosing.

Example 8

The purpose of this example was to demonstrate immunity generated against a SARS-CoV-2 variant using a vaccine composition described herein.

Two SARS-CoV-2 variants of concern are the UK (B.1.1.7) variant and the South Africa (B.1.351) variant. The UK (B.1.1.7) variant, also known as the Alpha SARS-CoV-2 variant, has been reported to have a rate of transmission 71% higher than other variants (*BMJ*, "Covid-19: What have we learned about the new variant in the UK?" Dec. 23, 2020). One report noted that the UK variant seemingly achieved dominance by outcompeting an existing population of circulating variants, which is strongly suggestive of natural selection of a virus that is more transmissible at a population level (Lauring et al., "Genetic Variants of SARS-CoV-2-What do They Mean?" *JAMA,* 325(6):529-531 (Feb. 9, 2021)). The South Africa (B.1.351) variant is associated with increased transmissibility, a higher viral load, and is defined by an unusually large number of mutations. (www.thermofisher.com/blog/ask-a-scientist/what-you-need-to-know-about-the-501y-v2-b-1-351-south-african-variant-of-sars-cov-2/, accessed on Jul. 16, 2021).

FIGS. 21A-21D show the robustness of the immunity generated by $EDV_{-COVID-\alpha-GC}$ by analyzing the specificity and cross-reactivity of the serum IgG from immunized mice against the RBD and S1 subunits of the UK (B.1.1.7) and South Africa (B.1.351) variants of the virus.

The results showed that, while UK variant RBD-specific IgG was produced in some of the $EDV\text{-}_{COVID-\alpha-GC}$ immunized mice (FIG. 21A), a much greater S1-specific IgG antibody titer was observed (FIG. 21B), indicating the binding of the S protein-specific antibody lands mainly outside of the RBD. A similar trend was observed for the SA variant (FIGS. 21C and D).

This data demonstrates the surprising broad effectiveness of the vaccine compositions of the disclosure against SARS-CoV-2 variants.

Example 9

The purpose of this example was to demonstrate immunity generated against a SARS-CoV-2 variant using a vaccine composition described herein.

Five groups of mice were administered a COVID variant vaccine as described herein and various controls. The five groups of mice (n=6 per group; ELISA samples run in triplicate) were: Group 1=saline; Group 2=EDV (bacterial minicell with no payload); Group 3=$EDV_{control}$(EDVs carrying the plasmid with no insert expressing the Spike protein i.e. plasmid backbone only); Group 4=$EDV_{Covid}$ (bacterial minicell comprising the plasmid and the encoded SARS-CoV-2 Spike protein) and Group 5=$EDV_{Covid+\alpha GC}$.

FIGS. 24A-D show the results of IgG titers following I.M. administration of $3\times10^9$ EDVs to the five different groups of mice on days 1 and 21, with serum analysis at day 28. The results shown in FIGS. 24A-D, detailing S1 subunit-specific IgG titers at day 28, demonstrate that serum IgG titers obtained from mice treated with $EDV_{-COVID-GC}$ binds strongly to all four mutant virus Spike proteins: (1) SARS-CoV-2 variant Alpha (B.1.1.7.UK) (FIG. 24A); (2) SARS-CoV-2 variant Beta (B.1.351. SA) (FIG. 24B); (3) SARS-CoV-2 variant Delta (B.1.617.2 India) (FIG. 24C); and (4) SARS-CoV-2 variant Gamma (P.1 Brazil) (FIG. 24D).

This data demonstrates the surprising broad effectiveness of the vaccine compositions of the disclosure against SARS-CoV-2 variants.

Example 10

The purpose of this example is to describe a clinical trial that is proposed to be conducted using a COVID-19 vaccine as described herein.

The clinical trial in healthy volunteers will comprise injecting intramuscularly $8 \times 10^9$ $EDV_{COVID\text{-}\alpha GC}$ on days Regla-Nava, J. A. et al. Severe acute respiratory syndrome coronaviruses with mutations in the E protein are attenuated and promising vaccine candidates. *J. Virol.* 89, 3870-3887 (2015).

Schoggins J W, Wilson S J, Panis M, et al. A diverse range of gene products are effectors of the type I interferon antiviral response. *Nature.* 2011; 472(7344):481-485.

Shang W, Yang Y, Rao Y, and Rao X. The outbreak of SARS-CoV-2 pneumonia calls for viral Vaccines npj Vaccines (2020) 5:18.

Sheahan et al., "Successful vaccination strategies that protect aged mice from lethal challenge from influenza virus and heterologous severe acute respiratory syndrome coronavirus," *J Virol.* 2011; 85(1):217-230.

Su, Brahmbhatt et. al., *Infection and Immunity,* 60(8):3345-3359 (1992).

Wu, F. et al. A new coronavirus associated with human respiratory disease in China. Nature. (2020).

Yue & Wu, "Progress and perspectives in developing polymeric vectors for in vitro gene delivery," *Biomater. Sci.,* 1:152-170 (2013).

Zaki A M, van Boheemen S, Bestebroer™, et al. Isolation of a novel coronavirus from a man with pneumonia in Saudi Arabia. *N Engl J Med.* 2012; 367(19):1814-1820.

---

What is claimed is:

1. A composition comprising:
   (a) a vector comprising:
      (i) a plasmid that encodes at least one coronavirus antigen protein, and
      (ii) the at least one coronavirus antigen protein encoded by the plasmid; and
   (b) a vector comprising α-galactosylceramide (α-Gal-Cer); and
   (c) at least one pharmaceutically acceptable carrier,
   wherein at least one of vector (a) and vector (b) is an intact, bacterially-derived minicell or killed bacterial cell.

2. The composition of claim 1, wherein:
   (a) vector (a) is a first intact, bacterially derived minicell or killed bacterial cell, and vector (b) is a second intact, bacterially derived minicell or killed bacterial cell; or
   (b) vector (a) and vector (b) are the same intact, bacterially derived minicell or killed bacterial cell, comprising the α-GaCer, the plasmid that encodes at least one coronavirus antigen protein, and the at least one coronavirus antigen protein encoded by the plasmid; or
   (c) one of vector (a) and vector (b) is not an intact, bacterially derived minicell or killed bacterial cell and the other of vector (a) and vector (b) is an intact, bacterially derived minicell or killed bacterial cell.

3. The composition of claim 1, wherein the coronavirus antigen comprises or characterizes a virus selected from the group consisting of an Alphacoronavirus; a Colacovirus such as Bat coronavirus CDPHE15; a Decacovirus such as Bat coronavirus HKU10 or Rhinolophus ferrumequinum alphacoronavirus HuB-2013; a Duvinacovirus such as Human coronavirus 229E; a Luchacovirus such as Lucheng Rn rat coronavirus; a Minacovirus such as a Ferret coronavirus or Mink coronavirus 1; a Minunacovirus such as Miniopterus bat coronavirus 1 or Miniopterus bat coronavirus HKU8; a Myotacovirus such as Myotis ricketti alphacoronavirus Sax-2011; a nyctacovirus such as Nyctalus velutinus alphacoronavirus SC-2013; a Pedacovirus such as Porcine epidemic diarrhea virus or Scotophilus bat coronavirus 512; a Rhinacovirus such as Rhinolophus bat coronavirus HKU2; a Setracovirus such as Human coronavirus NL63 or NL63-related bat coronavirus strain BtKYNL63-9b; a Tegacovirus such as Alphacoronavirus 1; a Betacoronavirus; a Embecovirus such as Betacoronavirus 1, Human coronavirus OC43, China Rattus coronavirus HKU24, Human coronavirus HKU1 or Murine coronavirus; a Hibecovirus such as Bat Hp-betacoronavirus Zhejiang2013; a Merbecovirus such as Hedgehog coronavirus 1, Middle East respiratory syndrome-related coronavirus (MERS-CoV), Pipistrellus bat coronavirus HKU5 or Tylonycteris bat coronavirus HKU4; a Nobecovirus such as Rousettus bat coronavirus GCCDC1 or Rousettus bat coronavirus HKU9, a Sarbecovirus such as a Severe acute respiratory syndrome-related coronavirus, Severe acute respiratory syndrome coronavirus (SARS-CoV) or Severe acute respiratory syndrome coronavirus 2 (SARS-CoV-2, COVID-19); a Deltacoronavirus; an Andecovirus such as Wigeon coronavirus HKU20; a Buldecovirus such as Bulbul coronavirus HKU11, Porcine coronavirus HKU15, Munia coronavirus HKU13 or White-eye coronavirus HKU16; a Herdecovirus such as Night heron coronavirus HKU19; a Moordecovirus such as Common moorhen coronavirus HKU21; a Gammacoronavirus; a Cegacovirus such as Beluga whale coronavirus SW1; and an Igacovirus such as Avian coronavirus.

4. The composition of claim 1, wherein the coronavirus antigen protein:
   (a) is encoded by a polynucleotide comprising the sequence of SARS-CoV-2, or a polynucleotide having at least 80% sequence identity to the polynucleotide comprising the sequence of SARS-CoV-2; and/or
   (b) comprises or is characteristic of human coronavirus 229E, human coronavirus OC43, SARS-CoV, HCoV NL63, HKU1, MERS-CoV, or SARS-CoV-2; and/or
   (c) comprises or is characteristic of SARS-CoV-2.

5. The composition of claim 1, wherein the coronavirus antigen is from a SARS-CoV-2 variant.

6. The composition of claim 5, wherein the SARS-CoV-2 variant is selected from the group consisting of:
(a) UK SARS-CoV-2 variant (B.1.1.7/VOC-202012/01);
(b) B.1.1.7 with E484K variant;
(c) B.1.617.2 (Delta) variant;
(d) B.1.617 variant;
(e) B.1.617.1 (Kappa) variant;
(f) B.1.617.3 variant;
(g) South Africa B.1.351 (Beta) variant;
(h) P.1 (Gamma) variant;
(i) B.1.525 (Eta) variant;
(j) B.1.526 (Iota) variant;
(k) Lambda (lineage C.37) variant;
(l) Epsilon (lineage B.1.429) variant;
(m) Epsilon (lineage B.1.427) variant;
(n) Epsilon (lineage CAL.20C) variant;
(o) Zeta (lineage P.2) variant;
(p) Theta (lineage P.3) variant;
(q) R.1 variant;
(r) Lineage B.1.1.207 variant;
(s) Lineage B.1.620 variant;
(t) a SARS-CoV-2 variant comprising a L452R Spike Protein Substitution;
(u) a SARS-CoV-2 variant comprising a E484K Spike Protein Substitution;
(v) a SARS-CoV-2 variant comprising a K417N Spike Protein Substitution;
(w) a SARS-CoV-2 variant comprising a E484K Spike Protein Substitution;
(x) a SARS-CoV-2 variant comprising a N501Y Spike Protein Substitution;
(y) a SARS-CoV-2 variant comprising a K417T Spike Protein Substitution;
(z) a SARS-CoV-2 variant comprising a E484K Spike Protein Substitution;
(aa) a SARS-CoV-2 variant comprising a N501Y Spike Protein Substitution;
(bb) SARs-CoV-2 variants having one or more of the following missense mutations: N440, L452R, S477G/N, E484Q, E484K, N501Y, D614G, P681H, P681R, and A701V; and
(cc) any combination of the above variants, substitutions, and/or mutations.

7. The composition of claim 5, wherein the vector (a) additionally comprises at least one coronavirus antigen from a SARS-CoV-2 strain.

8. The composition of claim 7, wherein the SARS-CoV-2 strain is selected from the group consisting of the L strain, the S strain, the V strain, the G strain, the GR strain, and the GH strain.

9. The composition of claim 7, wherein the coronavirus antigen protein is encoded by a polynucleotide comprising the sequence of SARS-CoV-2, or a polynucleotide having at least 80% sequence identity to the polynucleotide comprising the sequence of SARS-CoV-2.

10. The composition of claim 1, wherein the plasmid:
(a) encodes at least one of spike (S) protein, nucieocapsid (N) protein, membrane (M) protein, and envelope (E) protein of SARS-CoV-2 or a SARS-CoV-2 variant; and/or
(b) encodes the spike (S) protein, nucleocapsid (N) protein, membrane (M) protein, and the envelope (E) protein; and/or
(c) encodes the spike (S) protein of SARS-CoV-2 or a SARS-CoV-2 variant; and/or
(d) the receptor binding domain (RBD) of a Spike protein of SARS-CoV-2 or a SARS-CoV-2 variant.

11. The composition of claim 1, wherein the composition is formulated for oral administration, injection, nasal administration, pulmonary administration, or topical administration.

12. A vaccine composition comprising at least one intact, bacterially-derived minicell or killed bacterial cell, and comprised within the minicell or cell:
(a) a plasmid encoding a Spike protein from one or more of SARS-CoV-2 variant Alpha (B.1.1.7.UK), SARS-CoV-2 variant Beta (B.1.351. SA), SARS-CoV-2 variant Delta (B.1.617.2 India), and/or SARS-CoV-2 variant Gamma (P.1 Brazil); and
(b) α-galactosvlceramide (α-GalCer).

13. The vaccine composition of claim 12, wherein:
(a) the plasmid and the α-GalCer are comprised within a single minicell; and/or
(b) the plasmid encodes the Spike protein from each of SARS-CoV-2 variant Alpha (B.1.1.7.UK), SARS-CoV-2 variant Beta (B.1.351. SA), SARS-CoV-2 variant Delta (B.1.617.2 India), and SARS-CoV-2 variant Gamma (P.1 Brazil).

14. A method of treating and/or vaccinating against a viral infection, comprising administering to a subject in need a composition according to claim 1.

15. A method of treating and/or vaccinating against a viral infection, comprising administering to a subject in need a composition according to claim 5.

16. A method of treating and/or vaccinating against a viral infection, comprising administering to a subject in need a composition according to claim 12.

17. The method of claim 14, wherein the subject:
(a) is suffering from or at risk of developing lymphopenia; and/or
(b) is deemed at risk for severe illness and/or serious complications from the viral infection; and/or
(c) is about age 50 or older, about age 55 or older, about age 60 or older, or about age 65 or older; and/or
(d) suffers from one or more pre-existing conditions selected from the group consisting of diabetes, asthma, a respiratory disorder, high blood pressure, and heart disease;
and/or
(e) is immunocompromised; and/or
(f) is immunocompromised due to AIDS, cancer, a cancer treatment, hepatitis, an auto-immune disease, steroid receiving, immunosenescence, or any combination thereof.

18. The method of claim 14, wherein administration:
(a) increases the chance of survival following exposure to a coronavirus; and/or
(b) reduces the risk of transmission of coronavirus; and/or
(c) increases the chance of survival following exposure to a coronavirus by about 10%, about 20%, about 30%, about 40%, about 50%, about 60%, about 70%, about 80%, about 90%, or about 100%, as measured using any clinically recognized technique; and/or
(d) reduces the risk of transmission of coronavirus by about 10%, about 20%, about 30%, about 40%, about 50%, about 60%, about 70%, about 80%, about 90%, or about 100%, as measured using any clinically recognized technique.

19. The method of claim 14, wherein administering is via any pharmaceutically acceptable method.

20. The method of claim 14, wherein the subject:
(a) is exposed to or is anticipated to be exposed to an individual who is contagious for a coronavirus, and optionally wherein the individual who is contagious for a coronavirus has one or more symptoms selected from the group consisting of fever, cough, shortness of breath, diarrhea, sneezing, runny nose, and sore throat; and/or
(b) is a healthcare worker, aged 60 years or older, frequent traveler, military personnel, caregiver, or a subject with a preexisting condition that results in increased risk of mortality with infection.

21. The method of claim 14, further comprising administering one or more antiviral drugs.

22. The method of claim 21, wherein the one or more antiviral drugs are selected from the group consisting of chloroquine, darunavir, galidesivir, interferon beta, lopinavir, ritonavir, remdesivir, and triazavirin.

23. The method of claim 14, wherein the α-GalCer induces a Th1 cytokine response in the subject, and optionally wherein the cytokine comprises IFNγ.

24. The method of claim 14, wherein:
(a) a first minicell comprising the α-GalCer and a second minicell comprising the plasmid encoding at least one viral antigen are administered to the subject simultaneously; and/or
(b) a first minicell comprising the α-GalCer and a second minicell comprising the plasmid encoding at least one viral antigen are administered to the subject sequentially; and/or
(c) a first minicell comprising the α-GalCer and second minicells comprising the plasmid encoding at least one viral antigen are administered to the subject repeatedly; and/or
(d) a first minicell comprising the α-GalCer and second minicells comprising the plasmid encoding at least one viral antigen are administered to the subject at least once a week, twice a week, three times per week, or four times per week.

25. The composition of claim 2, wherein vector (a) and vector (b) are the same intact, bacterially derived minicell or killed bacterial cell, comprising the α-GalCer, the plasmid that encodes at least one coronavirus antigen protein, and the at least one coronavirus antigen protein encoded by the plasmid, wherein at least some of the coronavirus antigen protein is present in the membrane of the intact bacterially derived minicell or killed bacterial cell.

* * * * *